US009931787B2

United States Patent
Harrington et al.

(10) Patent No.: US 9,931,787 B2
(45) Date of Patent: Apr. 3, 2018

(54) CRIMPING POLYMER SCAFFOLDS

(71) Applicant: Abbott Cardiovascular Systems Inc., Santa Clara, CA (US)

(72) Inventors: Joel Harrington, Redwood City, CA (US); Jill McCoy, Sunnyvale, CA (US)

(73) Assignee: ABBOTT CARDIOVASCULAR SYSTEMS INC., Santa Clara, CA (US)

( * ) Notice: Subject to any disclaimer, the term of this patent is extended or adjusted under 35 U.S.C. 154(b) by 154 days.

(21) Appl. No.: 14/857,635

(22) Filed: Sep. 17, 2015

(65) Prior Publication Data

US 2016/0081824 A1   Mar. 24, 2016

Related U.S. Application Data

(60) Provisional application No. 62/052,399, filed on Sep. 18, 2014.

(51) Int. Cl.
| | |
|---|---|
| A61F 2/91 | (2013.01) |
| B23P 11/02 | (2006.01) |
| B29C 65/56 | (2006.01) |
| B23K 26/38 | (2014.01) |
| B23K 26/00 | (2014.01) |
| A61F 2/915 | (2013.01) |
| A61F 2/962 | (2013.01) |
| A61F 2/958 | (2013.01) |
| A61F 2/95 | (2013.01) |

(52) U.S. Cl.
CPC ............ B29C 65/56 (2013.01); A61F 2/915 (2013.01); B23K 26/0093 (2013.01); B23K 26/38 (2013.01); B23P 11/025 (2013.01); *A61F 2/91* (2013.01); *A61F 2/958* (2013.01); *A61F 2/962* (2013.01); *A61F 2002/91575* (2013.01); *A61F 2002/9522* (2013.01); *A61F 2210/0004* (2013.01); *A61F 2240/001* (2013.01); *Y10T 29/49865* (2015.01); *Y10T 29/49913* (2015.01); *Y10T 29/49929* (2015.01)

(58) Field of Classification Search
CPC ............ B23P 11/025; Y10T 29/49929; Y10T 29/49913; A61F 2/91; A61F 2/962; A61F 2/958; A61F 2/915

See application file for complete search history.

(56) References Cited

U.S. PATENT DOCUMENTS

| | | | |
|---|---|---|---|
| 5,702,656 A | 12/1997 | Sarver et al. | |
| 7,297,758 B2 | 11/2007 | Gale et al. | |
| 7,731,740 B2 | 6/2010 | LaFont et al. | |
| 7,761,968 B2 * | 7/2010 | Huang | A61F 2/90 29/447 |
| 8,539,663 B2 * | 9/2013 | Wang | A61F 2/95 29/505 |

(Continued)

OTHER PUBLICATIONS

Bartos, J. et al "Study of the influence of physical ageing and rejuvenation on macroradical reactivity in polycarbonate," Polymer, Jan. 13, 1992, vol. 33, No. 16, pp. 3536-3539.

(Continued)

*Primary Examiner* — Jermie Cozart
(74) *Attorney, Agent, or Firm* — Squire Patton Boggs (US) LLP

(57) ABSTRACT

A polymer scaffold is crimped to a balloon while the polymer material is in a thermodynamically unstable state, or a transient state including crimping shortly after a tube or scaffold processing step that imparts memory to the material, or shortly after rejuvenation of the scaffold.

27 Claims, 18 Drawing Sheets

(56) References Cited

U.S. PATENT DOCUMENTS

| | | |
|---|---|---|
| 2010/0004735 A1 | 1/2010 | Yang et al. |
| 2010/0323093 A1 | 12/2010 | Chen et al. |
| 2011/0066222 A1 | 3/2011 | Wang et al. |
| 2011/0190871 A1 | 8/2011 | Trollsas et al. |
| 2012/0042501 A1 | 2/2012 | Wang et al. |
| 2013/0025110 A1* | 1/2013 | Stankus .......... A61F 2/958 29/505 |
| 2013/0071549 A1 | 3/2013 | Chen et al. |
| 2013/0255853 A1 | 10/2013 | Wang et al. |
| 2014/0114399 A1 | 4/2014 | Hossainy et al. |

OTHER PUBLICATIONS

Cheng, Shiwang et al. "Crazing and strain localization of polycarbonate glass in creep," Polymer, Apr. 22, 2013, vol. 54, pp. 3363-3369.

Hay, James N. "The physical ageing of amorphous and crystalline polymers," Pure & Appl. Chem., 1995, vol. 67, No. 11, pp. 1855-1858.

Lee, Hau-Nan and Ediger, M.D. "Mechanical Rejuvenation in Poly (methacrylate) Glasses? Molecular Mobility after Deformation," Macromolecules, Jun. 8, 2010, vol. 43, pp. 5863-5873.

McKenna, Gregory B. "On the Physics Required for Prediction of Long Term Performance of Polymers and Their Composites," Journal of Research of the National Institute of Standards and Technology, Mar.-Apr. 1994, vol. 99, No. 2, pp. 169-189.

McKenna, Gregory, "Mechanical rejuvenation in polymer glasses: fact or fallacy," Journal of Physics: Condensed Matter, 2003, vol. 15, pp. S737-S763, downloaded from IOPscience, Jan. 31, 2010.

Struik, L.C.E. "Physical Aging in Plastics and Other Glassy Materials," Polymer Engineering and Science, Mar. 1977, vol. 17, No. 13, pp. 165-173.

\* cited by examiner

CRIMPING POLYMER SCAFFOLDS

This application claims priority to U.S. Provisional Application No. 62/052,399, filed Sep. 18, 2014, the entire contents of which, including all Appendices are herein incorporated by reference.

BACKGROUND OF THE INVENTION

Field of the Invention

The present invention relates to bioresorbable scaffolds; more particularly, this invention relates to bioresorbable scaffolds for treating vessels of the body.

Description of the State of the Art

Radially expandable endoprostheses are artificial devices adapted to be implanted in an anatomical lumen. An "anatomical lumen" refers to a cavity, duct, of a tubular organ such as a blood vessel, urinary tract, and bile duct. Stents are examples of endoprostheses that are generally cylindrical in shape and function to hold open and sometimes expand a segment of an anatomical lumen. Stents are often used in the treatment of atherosclerotic stenosis in blood vessels. "Stenosis" refers to a narrowing or constriction of the diameter of a bodily passage or orifice. In such treatments, stents reinforce the walls of the blood vessel and prevent restenosis following angioplasty in the vascular system. "Restenosis" refers to the reoccurrence of stenosis in a blood vessel or heart valve after it has been treated (as by balloon angioplasty, stenting, or valvuloplasty) with apparent success.

The treatment of a diseased site or lesion with a stent involves both delivery and deployment of the stent. "Delivery" refers to introducing and transporting the stent through an anatomical lumen to a desired treatment site, such as a lesion. "Deployment" corresponds to expansion of the stent within the lumen at the treatment region. Delivery and deployment of a stent are accomplished by positioning the stent about one end of a catheter, inserting the end of the catheter through the skin into an anatomical lumen, advancing the catheter in the anatomical lumen to a desired treatment location, expanding the stent at the treatment location, and removing the catheter from the lumen.

The following terminology is used. When reference is made to a "stent", this term will refer to a permanent structure, usually comprised of a metal or metal alloy, generally speaking, while a scaffold will refer to a structure comprising a bioresorbable polymer and capable of radially supporting a vessel for a limited period of time, e.g., 3, 6 or 12 months following implantation. It is understood, however, that the art sometimes uses the term "stent" when referring to either type of structure.

Scaffolds and stents traditionally fall into two general categories—balloon expanded and self-expanding. The later type expands (at least partially) to a deployed or expanded state within a vessel when a radial restraint is removed, while the former relies on an externally-applied force to configure it from a crimped or stowed state to the deployed or expanded state.

Self-expanding stents are designed to expand significantly when a radial restraint is removed such that a balloon is often not needed to deploy the stent. Self-expanding stents do not undergo, or undergo relatively no plastic or inelastic deformation when stowed in a sheath or placed on a balloon. Balloon expanded stents or scaffolds, by contrast, undergo a significant plastic or inelastic deformation when both crimped and later deployed by a balloon.

In the case of a balloon expandable stent, the stent is mounted about a balloon portion of a balloon catheter. The stent is compressed or crimped onto the balloon. Crimping may be achieved by use of an iris-type or other form of crimper, such as the crimping machine disclosed and illustrated in US 2012/0042501. A significant amount of plastic or inelastic deformation occurs both when the balloon expandable stent or scaffold is crimped and later deployed by a balloon. At the treatment site within the lumen, the stent is expanded by inflating the balloon.

The stent must be able to satisfy a number of basic, functional requirements. The stent must be capable of radial compressive forces imposed on the stent as it supports the walls of a vessel. Therefore, a stent must possess adequate radial strength. After deployment, the stent must adequately maintain its size and shape throughout its service life despite the various forces that may come to bear on it. In particular, the stent must adequately maintain a vessel at a prescribed diameter for a desired treatment time despite these forces. The treatment time may correspond to the time required for the vessel walls to remodel, after which the stent is no longer necessary for the vessel to maintain a desired diameter.

The present application adopts the definitions of radial strength and radial stiffness set forth in US2014/0114399. Radial strength, which is the ability of a stent to resist radial compressive forces, relates to a stent's radial yield strength around a circumferential direction of the stent. A stent's "radial yield strength" or "radial strength" (for purposes of this application) may be understood as the compressive loading, which if exceeded, creates a yield stress condition resulting in the stent diameter not returning to its unloaded diameter, i.e., there is irrecoverable deformation of the stent. When the radial yield strength is exceeded the stent is expected to yield more severely and only a minimal force is required to cause major deformation. A radial "stiffness" refers to the amount net radial inward force (i.e., uniform radial inward pressure over the entire abluminal scaffold surface×the abluminal surface area) required to reversibly decrease a scaffold diameter by a certain amount. The slope of the curve from a force-deflection plot will be called the "absolute stiffness" or K. The units are N/mm and the stiffness is expressed for the linearly elastic range of response to the radial force. Thus, for a scaffold deployed to 6.5 mm and having a linear elastic range for radial compression between 6.5 mm and 5.5 mm and a radial stiffness of 20 N/mm, a net inward radial inward force of 10 N is needed to decrease the scaffold diameter from 6.5 mm to 6.0 mm. After the radial force is removed, the scaffold returns to the 6.5 mm diameter.

The radial strength of the scaffold upon deployment can be high enough to provide mechanical support to a vessel after expanding the vessel to an increased diameter, such as a post-dilation or expanded diameter, or prevent or reduce a decrease in the diameter of the vessel. The radial strength of the scaffold may refer to a radial strength when expanded from the crimped state to a deployed state in water, saline, simulated body fluid, or bodily fluid at 37° C. The radial strength may be at least the value required to support a vessel at a reference vessel diameter, which is the healthy diameter of a vessel at an implant site. The radial strength is at least 350 mm Hg, at least 500 mm Hg, at least 650 mm Hg, at least 800 mm Hg, at least 1000 mm Hg, 400 to 600 mm Hg, 500 to 1200 mm Hg, 700 to 900 mm Hg, or 800 to 1300 mm Hg.

A commonly used type of peripheral stent is the self-expanding stent made from super-elastic material, such as Nitinol. This type of material is known for its ability to return to its original configuration after severe deformation, such as a crushing load or longitudinal bending. However, this variety of self-expanding stents have undesired qualities; most notably, the high resiliency of super-elastic material produces what is commonly referred to as a "chronic outward force" (COF) on the blood vessel supported by the stent. It is believed that a COF exerted on a blood vessel by a self-expending stent is a main contributor to high degrees of restenosis of lesions treated by the self-expanding stent. It has been shown that not even an anti-proliferative drug delivered from drug eluting self-expandable stents can mitigate the restenosis caused by the stent's COF. Stents that are plastically deformed by a balloon to support a vessel do not suffer from this drawback. Indeed, balloon expanded stents, in contrast to self-expanding stents made from a super-elastic material, have the desirable quality of being deployable to the desired diameter for supporting the vessel without exerting residual outward forces on the vessel.

A balloon-expanded polymer scaffold, such as that described in US 2010/0004735 is made from a biodegradable, bioabsorbable, bioresorbable, or bioerodible polymer. The terms biodegradable, bioabsorbable, bioresorbable, biosoluble or bioerodible refer to the property of a material or stent to degrade, absorb, resorb, or erode away from an implant site. The polymer scaffold described in US 2010/0004735, for example, as opposed to a metal stent, is intended to remain in the body for only a limited period of time. In many treatment applications, the presence of a stent in a body may be necessary for a limited period of time until its intended function of, for example, maintaining vascular patency and/or drug delivery is accomplished. Moreover, it has been shown that biodegradable scaffolds allow for improved healing of the anatomical lumen as compared to metal stents, which may lead to a reduced incidence of late stage thrombosis. In these cases, there is a desire to treat a vessel using a polymer scaffold, in particular a bioabsorable or bioresorbable polymer scaffold, as opposed to a metal stent, so that the prosthesis's presence in the vessel is for a limited duration. However, there are numerous challenges to overcome when developing a polymeric scaffold.

Polymer material considered for use as a polymeric scaffold, e.g. poly(L-lactide) ("PLLA"), poly(L-lactide-co-glycolide) ("PLGA"), poly(D-lactide-co-glycolide) or poly(L-lactide-co-D-lactide) ("PLLA-co-PDLA") with less than 10% D-lactide, and PLLD/PDLA stereo complex, may be described, through comparison with a metallic material used to form a stent, in some of the following ways. A suitable polymer has a low strength to volume ratio, which means more material is needed to provide an equivalent mechanical property to that of a metal. Therefore, struts must be made thicker and wider to have the required strength for a stent to support lumen walls at a desired radius. The scaffold made from such polymers also tends to be brittle or have limited fracture toughness. The anisotropic and rate-dependent inelastic properties (i.e., strength/stiffness of the material varies depending upon the rate at which the material is deformed, in addition to the temperature, degree of hydration, thermal history) inherent in the material, only compound this complexity in working with a polymer, particularly, bioresorbable polymer such as PLLA or PLGA.

Scaffolds used to treat coronary vessels experience, for the most part, a primarily radial loading. However, scaffolds intended for peripheral vessels experience a quite different loading, to such an extent that the traditional measure of a stent's fitness for use, i.e., its radial strength/stiffness, is not an accurate measure of whether the scaffold will have sufficient strength to provide mechanical support within the peripheral vessel for the duration needed. This is because a peripheral scaffold is placed in a significantly different environment from a coronary scaffold. The vessel size is larger. And there is much more movement of the vessel, with motions in different directions, especially when located close to an articulating joint. As such, a scaffold intended for a peripheral vessel will need to be able to sustain more complex loading, including a combination of axial, bending, torsional and radial loading. These and related challenges facing peripherally implanted scaffolds are discussed in US2011/0190871 and US2014/0114399.

The ageing process that occurs in polymers is well known. U.S. Pat. No. 7,297,758 describes changes in a polymer material in terms of a concept known as "densification." It has been previously proposed that when a material is exposed to mechanical strain the effects of ageing can be removed in a polymer. See Lee, Hau-Nan & Ediger, M. D., *Mechanical Rejuvenation in Poly (methyl methacrylate) Glasses? Molecular Mobility after Deformation*, Macromolecules 2010, 43, 5863-5873 (pub. Jun. 8, 2010).

A continued need exists for improving the mechanical properties of polymer scaffolds crimped to balloons, for both coronary and peripheral applications.

SUMMARY OF THE INVENTION

A process for improving the mechanical properties of scaffolds that are crimped to a balloon according to the invention includes doing mechanical work on, or adding heat to a polymer tube or scaffold to reverse or erase at least some portion of physical ageing that has occurred in the material; more specifically, a portion of physical ageing is removed sufficient to enable the tube or scaffold to more easily sustain high strains when the scaffold is crimped to a balloon, as demonstrated by noticeable reductions in cracking, crazing, void formation as compared to the same scaffold without a reduction in ageing. The invention also contemplates crimping a scaffold to a balloon shortly after making the scaffold, or storing the scaffold at a reduced temperature until the time of crimping.

Physical ageing of a polymer, and specifically a polymer scaffold, refers to changes in transient physical and thermodynamic properties of the polymer of the scaffold with time. Physical ageing is of particular relevance for amorphous and semi-crystalline polymers that include amorphous regions that have glass transition temperatures ($T_g$) above their normal storage temperature, which is typically ambient or room temperature, i.e., from about 15° C. to about 35° C., or more narrowly, 20° C. to about 30° C., 25° C., or about 30° C. At temperatures below Tg semi-crystalline and amorphous polymers are not in thermodynamic equilibrium and physical properties, such as specific volume, enthalpy and entropy which are greater than the equilibrium values decrease towards the equilibrium values at rates which decrease with the degree of undercooling below the Tg.

Physical ageing can make the scaffold brittle (or more brittle) and more susceptible to fracture when the scaffold is plastically deformed during crimping. The changes in physical properties that occur during physical ageing include an increase in density, increase in modulus, decrease in compliance, increase in stiffness, and a decrease in ultimate strength. The physical ageing process is also associated with enthalpy relaxation (a decrease in enthalpy) and can be characterized with differential scanning calorimetry (DSC)

by the excess endothermic relaxation peak (excess enthalpy) that occurs near Tg. Therefore, one can measure the extent of the physical ageing by characterizing the excess enthalpy using DSC. Excess enthalpy is analyzed from the extra peak area above the base thermogram of a non-aged (or second heated) sample near glass transition temperature.

The inventors believe that the scaffold crimping process results in significant losses of radial strength of a polymer scaffold due to damage from deformation that occurs during crimping. The damage occurs in the crests of the scaffold that undergo high deformation during crimping and deployment. The embrittlement of the scaffold caused by physical ageing results in more damage during deployment and hence the lower radial strength and expansion capability.

Physical ageing of a semi-crystalline polymer tube/scaffold may be explained as—relaxation of enthalpic and/or free volume interactions between molecular configurations that existed at the time when heat was added, or work was done on the material (e.g., during and shortly after blow molding an extruded tube). Long-chain polymer forms are usually thermodynamically unstable due to chain entanglement. The material moves over time towards more thermodynamic stability, which results in a concomitant relaxation of enthalpic interactions and/or free volume between regions, thereby limiting the ability of polymer chains to move freely relative to one another. Stated somewhat differently, after a period of time has elapsed a semi-crystalline polymer tube/scaffold becomes more brittle (due to stronger enthalpic interactions and/or loss of free volume between regions), thus limiting the material's ability to accommodate everywhere (especially at crowns) the enforced strains associated with crimping or balloon expansion from a crimped state.

According to the disclosure, several embodiments of processes are contemplated for avoiding the crimping of an aged polymer scaffold to a balloon. It is an object of the invention to crimp a polymer scaffold to the balloon prior to any significant ageing of the material. Generally speaking, this may be accomplished by employing one or more, or any combination of three techniques: crimping shortly after an earlier processing that made the scaffold, erasing age effects in the polymer material before crimping by heating and/or doing work on the material, or freezing the scaffold shortly after it is made, e.g., shortly after the scaffold was formed from a tube that was radially deformed at an elevated temperature above the glass transition temperature for the polymer.

According to some embodiments a scaffold is maintained at a low temperature between a first and second process. The lowered temperature effectively "freezes" the material to inhibit or slow-down ageing The first process raises the material temperature above the glass transition temperature and/or radially deforms the scaffold beyond a yield strain (blow-molding of an extruded tube is one example of the first process). The second process is crimping. For these embodiments a longer period of time may elapse from the end of the first process stage and beginning of the second process stage. The second process may be characterized as imposing forces on the scaffold that results in strain regions beyond the yield strain of the material. Thus a second process that imparts no more than an elastic strain on the material is not a second process.

According to one embodiment rejuvenation by mechanical strain applies a radial-outward pressure to a scaffold ring resulting in a yield condition at the ring's crests. More specifically, it is found that effective rejuvenation can occur for a strain in the material at the crest of between about 5 to 20% beyond the point where yield begins to occur (i.e., the crest begins to plastically deform, or does not revert back to its undeformed shape when the radially-outward pressure force is withdrawn). It will be appreciated that the yield strain point at a crest may be predicted as a function of radial pressure using Finite Element Modeling (FEM) or by a locating the transition from elastic to plastic deformation from a force vs. radial deflection curve for the scaffold.

According to some embodiments rejuvenation by mechanical strain includes, one or more, or any combination of the following features: apply a radially outward pressure to a scaffold resulting in an about 5 to 7%, 5 to 10% or about 10 to 15% increase in the scaffold diameter; during rejuvenation the scaffold has a temperature below Tg for the scaffold material, or between about Tg and 5, 10, 15, 20 or 25 degrees below Tg for the scaffold material; after radial expansion the scaffold diameter is held at the expanded diameter for an about 1 to 5 second dwell, or 10 to 30 second dwell before the radial constraint is withdrawn; the rejuvenation is done within a crimp head or shortly before placing the scaffold within a crimp head; and/or the rejuvenation occurs prior to any diameter reduction within the crimp head, or after a first or second diameter reduction within a crimp head; and/or rejuvenation is performed using a balloon catheter that is the same as the balloon catheter to which the scaffold is crimped; or there is a first catheter for rejuvenation and a second catheter to which the scaffold is crimped and the balloon of the first catheter has a higher nominal diameter than the balloon of the second catheter.

According to some embodiments rejuvenation by heating includes raising the scaffold temperature above Tg as part of a coating process, which includes one or more or any combination of the following features: rejuvenation when a coating is applied, or during a solvent removal step; a forced-air drying of a coating where the air has a temperature above Tg for the scaffold backbone material (e.g., the material of a tube form which the scaffold was made); and/or a baking step after coating where the oven temperature is above Tg for the scaffold backbone material. Examples of apparatus and/or processes for coating and removing solvent by heating the scaffold (either after or during coating) are provided in US20130071549, specifically any of the coating apparatus and/or processes described at paragraphs [0042]-[0049], [0061]-[0069] and FIGS. 1A, 1B, 2, 3 and 9 of US20130071549.

According to some embodiments there is a medical device comprising a scaffold crimped to a balloon, a method for crimping, a method for making or fabricating, a process for making, a method for treating, or a method for assembly of the medical device comprising one or more, or any combination of the following things (1) through (43):

(1) the scaffold is made from a polymer composition having a processing memory comprising biaxially orientated polymer chains;
(2) the balloon nominal diameter is at least about two-times the outer diameter of the crimped scaffold;
(3) the scaffold wall thickness is less than about 150 microns, about 100 microns, about 120 microns, less than about 100 microns, between about 88 and 100 microns, between about 100 and 120 microns, or between about 80 and 100 microns;
(4) an aspect ratio (AR) of strut width to wall thickness of a strut of the scaffold is between about 1.5 and 1.9, 1.5 to 1.8, 1 to 1.5, 1 to 2.2 or 1.4 to 2.2;
(5) a strut width of 0.007 to 0.0075 in (180 to 190 microns);

(6) 3 links orientated parallel to a longitudinal axis and forming Y-crowns and W-crowns;
(7) 6 or 7 rings;
(8) W-shaped, symmetric closed-cells (where the symmetry refers to the links that connect one W-shaped cell to adjacent cells) and/or W-V-shaped asymmetric closed-cells (where the asymmetry refers to the links that connect one W-V-shaped cell to adjacent cells);
(9) The polymer composition is PLLA, high molecular weight PLLA, or a blend of PLLA and poly(L-lactide-co-caprolactone) copolymer, referred to as PLLA/PCL where the percentage of PLLA and PCL, PLLA/PCL: 95/5, 90/10, 97/3; and/or
(10) The radial strength of the scaffold at deployment (inflated, expanded or post-dilation diameters in 37 Deg. saline or water) is at least 350 mm Hg, at least 500 mm Hg, at least 650 mm Hg, at least 800 mm Hg, at least 1000 mm Hg, 400 to 600 mm Hg, 500 to 1200 mm Hg, 700 to 900 mm Hg, or 800 to 1300 mm Hg.
(11) A coating process as described in US20130071549; specifically, any of the coating apparatus and/or processes described at paragraphs [0042]-[0049], [0061]-[0069] and FIGS. 1A, 1B, 2, 3 and 9 of US20130071549.
(12) A crimping process as described in any of US20130255853; specifically any of the crimping processes and apparatus for crimping described at paragraphs [0068]-[0073], [0077]-[0099], [0111]-[0126], [0131]-[0146] and FIGS. 1A, 1B, 4A. 4B, 5A, 5B, 8A, 8B of US20130255853.
(13) A blow molding or stent-forming process as described in US20110066222, specifically any of the processes described at paragraphs [0040], [0044]-[0062], [0064]-[0073] and FIGS. 2, and 3A-3D.
(14) A method of fabricating a polymer stent comprising: providing a biodegradable polymer scaffold comprising a polymer, the scaffold having an expanded configuration and a crimped configuration for delivery in a vascular lumen; thermally treating the scaffold to reverse physical aging of the scaffold; and crimping the scaffold to the crimped configuration having reversed physical aging or shortly after thermally treating
(15) The method of (14) having one or more, or any combination of the following items a)-ee):
a) the provided scaffold comprises induced biaxial orientation of the polymer chains and the thermally treated scaffold includes at least some of the induced biaxial orientation;
b) the thermal treatment reduces damage due to crimping at the crest regions of the scaffold;
c) reversed physical aging comprises a modification selected from the group consisting of decreased density of the scaffold polymer, increased elongation at break of the scaffold polymer, decreased modulus of the scaffold polymer, increased radial strength of the scaffold, increase expansion capability of the scaffold, reduced damage to the scaffold at crimping, and any combination thereof;
d) the thermal treatment is above a glass transition temperature (Tg) and below a melting temperature (Tm) of the polymer in the expanded configuration;
e) the provided scaffold comprises a crystallinity of at least 20%;
f) the thermal treatment is performed after forming the scaffold from a tube and before coating the scaffold;
g) the thermal treatment is performed during a coating step of the scaffold;
h) the thermal treatment is performed after coating the scaffold;
i) freezing the scaffold after the thermal treatment to prevent the physical aging;
j) the scaffold is crimped from 60 sec to 60 min after the thermal treatment;
k) the scaffold is crimped from 60 sec to 60 min after the thermal treatment;
l) the thermal treatment is at a temperature from Tg to (Tg+Tm)/2;
m) the thermal treatment does not increase a crystallinity of the scaffold;
n) the thermal treatment increases a crystallinity of the scaffold by 0.6 to 2%;
o) the scaffold has a crystallinity between 20 and 50%;
p) a time of the thermal treatment is 60 sec to 60 min;
q) the time of the thermal treatment is 8 to 60 min;
r) the thermal treatment is performed in an inert atmosphere;
s) the thermal treatment is performed in a vacuum oven;
t) the scaffold is disposed on a rod during the treatment and the scaffold is heated electrically or by passage of a heat transfer fluid through the scaffold;
u) the treatment comprises heating steps to dry coating composition applied to the scaffold between repeated coating composition application steps, wherein a temperature of the heating steps is 80° C. to 620° C.;
v) the scaffold is crimped less than 60 min after coating the scaffold;
w) the thermal treatment is performed with the scaffold disposed within a crimper prior to crimping to the crimped configuration, wherein the crimper is configured to heat the scaffold;
x) the thermal treatment is performed with the scaffold disposed within a crimper prior to crimping and the scaffold is heated by heated air passing through a crimper bore in which the scaffold is disposed;
y) the thermal treatment is performed with the scaffold disposed within a crimper prior to crimping and the scaffold is heated by a crimper having jaws;
z) the thermal treatment is performed with the scaffold disposed within a crimper prior to crimping, the crimper having jaws that are hollow that contain a recirculating heat transfer fluid;
aa) the thermal treatment comprises moving the scaffold through a tunnel or conveyor oven;
bb) the thermal treatment comprises heating the scaffold in a microwave oven containing air or an inert gas;
cc) the thermal treatment comprises heating the scaffold using RF induction heating;
dd) the thermal treatment comprises heating the scaffold with an infrared lamp; and/or
ee) shortly after the thermal treatment, storing the scaffold at a temperature of 4° C. or less, further comprising removing the scaffold from the container, allowing the scaffold to equilibrate to ambient temperature, and crimping the equilibrated scaffold to the crimped configuration.
(16) A method of fabricating a polymer stent comprising: providing a biodegradable polymer scaffold comprising a polymer, wherein the scaffold comprises induced biaxial orientation of the polymer chains, the scaffold having an expanded configuration and a crimped configuration for delivery in a vascular lumen; thermally treating the scaffold to reverse physical aging of the scaffold, and crimping the scaffold to the crimped configuration having reversed physical aging or shortly after thermally treating

(17) The method of (16) having one or more, or any combination of the following items a)-d):
   a) the thermally treated scaffold includes at least some of the induced biaxial orientation;
   b) the thermal treatment reduces damage due to crimping at the crest regions of the scaffold;
   c) the thermal treatment is above a glass transition temperature (Tg) and below a melting temperature (Tm) of the polymer in the expanded configuration; and/or
   d) reversal of physical aging comprises a modification of the scaffold selected from the group consisting of decrease density of the scaffold polymer, increase elongation at break of the scaffold polymer, decrease modulus of the scaffold polymer, increase radial strength of the scaffold, increase expansion capability of the scaffold, reduced damage to the scaffold at crimping, and any combination thereof.

(18) A method of fabricating a polymer stent comprising: providing a biodegradable polymer scaffold comprising a polymer, the scaffold having an expanded configuration and a crimped configuration for delivery in a vascular lumen; thermally treating the scaffold above a glass transition temperature (Tg) and below a melting temperature (Tm) of the polymer to reverse physical aging of the scaffold; optionally freezing the scaffold shortly after thermally treating; and crimping the scaffold to the crimped configuration shortly after the thermal treatment or shortly after thawing the frozen scaffold.

(19) The method of (18) having one or more, or any combination of the following items (a)-(d):
   a) the provided scaffold comprises induced biaxial orientation of the polymer chains and the thermally treated scaffold includes at least some of the induced biaxial orientation;
   b) the thermal treatment time is 6 to 65 min;
   c) the thermal treatment modifies the scaffold, the modification selected from the group consisting of decrease density of the scaffold polymer, increase elongation at break of the scaffold polymer, decrease modulus of the scaffold polymer, increase radial strength of the scaffold, increase expandability of the scaffold, reduced damage to the scaffold at crimping, and any combination thereof; and/or
   d) the thermal processing reduces damage due to crimping at the crest regions of the scaffold.

(20) A method of fabricating a polymer stent comprising: processing a bioresorbable polymer to form a radially expandable scaffold, the processing comprising increasing a temperature of the polymer above a glass transition temperature (Tg) and below a melting temperature (Tm) followed by reducing the temperature below the Tg, the scaffold having an expanded configuration and a crimped configuration for delivery in a vascular lumen; thermally treating the scaffold to reverse physical aging of the scaffold, and crimping the scaffold to the crimped configuration having reversed physical aging or shortly after thermally treating

(21) The method of (20) having one or more, or any combination of the following items (a)-(e):
   a) the thermal treatment does not erase memory of the processing;
   b) the processing comprises inducing biaxial orientation of the polymer chains and the thermally treated scaffold includes at least some of the induced biaxial orientation;
   c) the thermal treatment reduces damage due to crimping at the crest regions of the scaffold;
   d) following forming of the scaffold, physical aging of the scaffold causes modification selected from the group consisting of increased density of the scaffold polymer, decreased elongation at break of the scaffold polymer, increased modulus of the scaffold polymer, decrease in expandability of the scaffold, decrease in radial strength of the scaffold, and any combination thereof; and/or
   e) the thermal treatment modifies the scaffold, the modification selected from the group consisting of decrease density of the scaffold polymer, increase elongation at break of the scaffold polymer, decrease modulus of the scaffold polymer, increase radial strength of the scaffold, increase expandability of the scaffold, reduced damage to the scaffold at crimping, and any combination thereof.

(22) A method of fabricating a polymer stent comprising: processing a bioresorbable polymer to form a radially expandable scaffold, the scaffold having an expanded configuration and a crimped configuration for delivery in a vascular lumen, the processing comprising increasing a temperature of the polymer above a glass transition temperature (Tg) and below a melting temperature (Tm) followed by reducing the temperature below the Tg, thermally treating the scaffold to reverse physical aging, the thermal treatment being above a glass transition temperature (Tg) and below a melting temperature (Tm) of the polymer; and optionally freezing the scaffold shortly after thermally treating; and crimping the scaffold to the crimped configuration shortly after the thermal treatment or shortly after thawing the frozen scaffold.

(23) The method of (22) having one or more, or any combination of the following items (a)-(d):
   a) the thermal treatment does not erase memory of the processing;
   b) the processing comprises inducing a biaxial orientation of the polymer chains and the thermally treated scaffold includes at least some of the induced biaxial orientation;
   c) the thermal treatment reduces damage due to crimping at the crest regions of the scaffold; and/or
   d) the thermal treatment modifies the scaffold, the modification selected from the group consisting of decreased density of scaffold polymer, increased elongation at break of the scaffold polymer, decreased modulus of the scaffold polymer, increased radial strength of the scaffold, increased expansion capability of the scaffold, reduced damage to the scaffold at crimping, and any combination thereof.

(24) A method of fabricating a polymer stent comprising: providing a biodegradable polymer scaffold comprising a polymer, the scaffold having an expanded configuration and a crimped configuration for delivery in a vascular lumen; treating the scaffold with a solvent to reverse physical aging of the scaffold; and crimping the scaffold to the crimped configuration having reversed physical aging or shortly after solvent treating.

(25) The method of (24) having one or more, or any combination of the following items (a)-(f):

a) the provided scaffold comprises induced biaxial orientation of the polymer chains and the solvent treated scaffold includes at least some of the induced biaxial orientation;
b) the treatment comprises placing the scaffold disposed on a mandrel in a chamber filled with solvent vapor;
c) the treatment is performed at ambient temperature;
d) the solvent is selected from the group consisting of acetonitrile, dimethylsulfoxide (DMSO), chloroform, acetone, water (buffered saline), xylene, methanol, ethanol, 6-propanol, tetrahydrofuran, 6-butanone, dimethylformamide, dimethylacetamide, cyclohexanone, ethyl acetate, methylethylketone, propylene glycol monomethylether, isopropanol, isopropanol admixed with water, N-methylpyrrolidinone, toluene, and any combinations thereof;
e) the treatment comprises removing solvent from the scaffold prior to crimping; and/or
f) the solvent treatment modifies the scaffold, the modification selected from the group consisting of decreased density of scaffold polymer, increased elongation at break of the scaffold polymer, decreased modulus of the scaffold polymer, increased radial strength of the scaffold, increased expansion capability of the scaffold, reduced damage to the scaffold at crimping, and any combination thereof.

(26) A method of fabricating a polymer stent comprising: processing a bioresorbable polymer to form a radially expandable scaffold, the processing comprising increasing a temperature of the polymer above a glass transition temperature (Tg) and below a melting temperature (Tm) followed by reducing the temperature below the Tg, the scaffold having an expanded configuration and a crimped configuration for delivery in a vascular lumen; solvent treating the scaffold to reverse physical aging of the scaffold, and crimping the scaffold to the crimped configuration having reversed physical aging or shortly after thermally treating

(27) The method of (26) having one or more, or any combination of the following items (a)-(f):
a) the solvent treatment does not erase memory of the processing;
b) the processing comprises inducing a biaxial orientation of the polymer chains and the thermally treated scaffold includes at least some of the induced biaxial orientation;
c) the solvent treatment reduces damage due to crimping at the crest regions of the scaffold;
d) following forming of the scaffold, physical aging of the scaffold causes modification selected from the group consisting of increased density of the scaffold polymer, decreased elongation at break of the scaffold polymer, increased modulus of the scaffold polymer, decrease in expandability of the scaffold, decrease in radial strength of the scaffold, and any combination thereof;
e) the solvent treatment modifies the scaffold, the modification selected from the group consisting of decrease density of the scaffold polymer, increase elongation at break of the scaffold polymer, decrease modulus of the scaffold polymer, increase radial strength of the scaffold, increase expansion capability of the scaffold, reduced damage to the scaffold at crimping, and any combination thereof; and/or
f) the treatment comprises removing solvent from the scaffold prior to crimping.

(28) A method for making a medical device, comprising: providing a tube made from a material comprising a polymer composition having a glass transition temperature (Tg), the tube being formed by, or modified by a forming process, wherein the forming process includes the step of at least one of raising the temperature of the tube to about, or greater than about Tg or radially straining the material beyond a yield strain for the material; making a scaffold from the tube formed by, or modified by the forming process; and crimping the scaffold to a balloon shortly after the tube is formed by, or modified by the forming process.

(29) The method of (28) having one or more, or any combination of the following items a)-j):
a) further comprising: reducing the temperature of the tube and/or scaffold to about 50, 60, 80, 100, 50 to 150, or about 50 to 80 degrees below Tg; and crimping the thawed scaffold to a balloon;
b) further comprising: rejuvenating the scaffold before crimping.
c) wherein the rejuvenating the scaffold includes at least one of raising the scaffold temperature to above about Tg or radially expanding the scaffold to induce a strain in the material beyond the yield strain of the material;
d) wherein the rejuvenating the scaffold includes radially expanding the scaffold diameter by about 5 to 7%, about 5 to 10%, or about 10 to 15% relative to a pre-crimp scaffold diameter or a partially crimped scaffold diameter;
e) wherein the scaffold diameter is reduced in diameter, followed by the radially expanding the scaffold diameter and the scaffold diameter;
f) wherein the rejuvenation takes place within a crimp head of a crimping mechanism;
g) wherein the crimping step comprises rejuvenating the scaffold, wherein the scaffold diameter is increased after being partially crimped;
h) wherein the rejuvenation includes inducing a strain beyond a yield, wherein a crest of a scaffold ring has a highest yield strain of about 5 to 20% beyond the strain where yield occurs for the scaffold crest when the scaffold is radially expanded;
i) wherein the scaffold temperature is about Tg, or about 30, 20, 15 or 5 Deg. C. less than Tg when the scaffold diameter is increased; and/or
j) wherein the crimping includes one or more of, or any combination of:
apply a radially outward pressure to a scaffold resulting in an about 5 to 7%, 5 to 10% or about 10 to 15% increase in the scaffold diameter; during rejuvenation the scaffold has a temperature below Tg for the scaffold material, or between about Tg and 5, 10, 15, 20 or 25 degrees below Tg for the scaffold material; after radial expansion the scaffold diameter is held at the expanded diameter for an about 1 to 5 second dwell, or 10 to 30 second dwell before a radial constraint is withdrawn; the rejuvenation is done within a crimp head or shortly before placing the scaffold within a crimp head; rejuvenation occurs prior to any diameter reduction within the crimp head, or after a first or second diameter reduction within a crimp head; and/or rejuvenation is performed using a balloon catheter that is the same as the balloon catheter to which the scaffold is crimped, and/or there is a first catheter for rejuvenation and a second catheter to which the scaffold is crimped and the balloon of the first catheter has a higher nominal diameter than the balloon of the second catheter.
- (30) A wall thickness of the tube or scaffold at crimping is less than about 150 microns, about 100 microns, about 120 microns, less than about 100 microns, between about 88 and 100 microns, between about 100 and 120 microns, or between about 80 and 100 microns.
- (31) An aspect ratio (AR) of strut width to wall thickness of a strut of the scaffold is between about 1.5 and 1.9, 1.5 to 1.8, 1 to 1.5, 1 to 2.2 or 1.4 to 2.2.
- (32) The tube is substantially or completely a blend of polylactide (PLA) and a PLA and polycaprolactone (PCL) random copolymer (20% PCL) and the blended PLA-PCL combination has between about 1% to 5% by weight PCL; or the tube comprises substantially high molecular weight PLLA.
- (33) The scaffold has rings interconnected by struts, and the scaffold pattern is one of rings with 6 or 7 crests and 3 links connecting adjacent rings, and the scaffold pattern has one of symmetric W-cells or a combination of symmetric W-calls and asymmetric W-V cells.
- (34) The forming process induces a biaxial orientation of polymer chains to increase a radial strength in the tube.
- (35) A method for making a medical device, comprising: providing a tube made from a material comprising a polymer composition having a glass transition temperature (Tg), the tube being formed by, or modified by a forming process, wherein the forming process includes the step of at least one of raising the temperature of the tube to about, or greater than about Tg or radially straining the material beyond a yield strain for the material; making a scaffold from the tube formed by, or modified by the forming process; shortly after making the scaffold, reducing the temperature of the scaffold to about 50, 60, 80, 100, 50 to 150, or about 50 to 80 degrees below Tg; thawing the scaffold; and crimping the scaffold to a balloon shortly after thawing the scaffold.
- (36) A method for crimping, comprising: providing a scaffolding comprising a polymer having a glass transition temperature (Tg); and placing the scaffold within a crimping device and while the scaffold is within the crimping device performing the steps of: raising the temperature of the scaffold to between about 10 to 20 degrees above Tg, followed by lowering the scaffold temperature to between about Tg and 15 degrees below Tg; and while the scaffold has the lowered temperature crimping the scaffold from a first diameter to a second diameter.
- (37) The method of (36) having one or more, or any combination of the following items a)-c):
  - a) wherein the scaffold has biaxially orientated polymer chains during crimping and after raising the temperature of the scaffold to between about 10 to 20 degrees above Tg;
  - b) The method of Claim 3-3a, further including the step of erasing ageing in the scaffold comprising the step of raising the temperature of the scaffold to between about 10 to 20 degrees above Tg and maintaining the temperature for between about less than 10 or 20 minutes or between about 5 and 10 minutes; and/or
  - c) The method of Claim 3-3b, wherein the crimping includes inflating the balloon when the scaffold diameter is being reduced in size.
- (38) A method for coating, comprising the steps of: applying a coating comprising a solvent to a scaffold made from a polymer tube, wherein the tube polymer has a glass transition temperature (Tg); and removing the solvent, including the step of raising the temperature of the scaffold to above Tg.
- (39) The method of (38) having one or more, or any combination of the following items a)-d):
  - a) wherein the removing a solvent includes the step of applying forced air drying to remove the solvent, wherein the forced air has a temperature above Tg;
  - b) wherein the removing a solvent includes the step of placing the scaffold within a closed space having a temperature above Tg;
  - c) wherein the temperature is between about 10 to 20 degrees above Tg; and/or
  - d) further including the step of erasing ageing in the scaffold comprising the step of raising the temperature of the scaffold to between about 10 to 20 degrees above Tg and maintaining the temperature for between about less than 10 or 20 minutes or between about 5 and 10 minutes.
- (40) A method for making a medical device, comprising: providing a tube made from a material comprising a polymer composition; radially strengthening the tube by inducing a biaxial orientation of polymer chains in the tube; cutting a scaffold from the tube while the tube has the biaxial orientation of polymer chains; erasing ageing in the scaffold; and after erasing ageing, crimping the scaffold to a balloon.
- (41) The method of (40) having one or more, or any combination of the following items a)-f):
  - a) wherein the polymer composition has a glass transition temperature (Tg) and the erasing ageing includes the step of raising the scaffold temperature to between about 10 and 20 degrees above Tg;
  - b) wherein the erasing ageing includes the step of raising the scaffold temperature above Tg for a duration of not more than 5, 10 or 20 minutes;
  - c) wherein the scaffold is crimped to the balloon between about 30 minutes, 1 hour, 5 hours, not more than 8 hours or not more than 24 hours after the erasing ageing;
  - d) further including the step of coating the scaffold with a drug-polymer composition after erasing ageing and before crimping the scaffold to the balloon;
  - e) wherein the erasing ageing takes place within a crimp head; and/or
  - f) wherein the radially strengthening the tube includes one or more of blow-molding above Tg, die drawing above Tg.
- (42) A method of fabricating a polymer stent comprising: providing a biodegradable polymer scaffold comprising a polymer, the scaffold having an expanded configuration and a crimped configuration for delivery in a vascular lumen; thermally treating the scaffold to reverse physical aging of the scaffold; and crimping the scaffold to the crimped configuration having reversed physical aging or shortly after thermally treating.
- (43) The method of (42) having one or more, or any combination of the following items a)-b):
  - a) wherein the provided scaffold comprises induced biaxial orientation of the polymer chains and the thermally treated scaffold includes at least some of the induced biaxial orientation; and/or
  - b) wherein the thermal treatment reduces damage due to crimping at the crest regions of the scaffold.

INCORPORATION BY REFERENCE

All publications and patent applications mentioned in the present specification are herein incorporated by reference to the same extent as if each individual publication or patent application was specifically and individually indicated to be incorporated by reference. To the extent there are any inconsistent usages of words and/or phrases between an incorporated publication or patent and the present specification, these words and/or phrases will have a meaning that is consistent with the manner in which they are used in the present specification.

DETAILED DESCRIPTION

Figure 1:
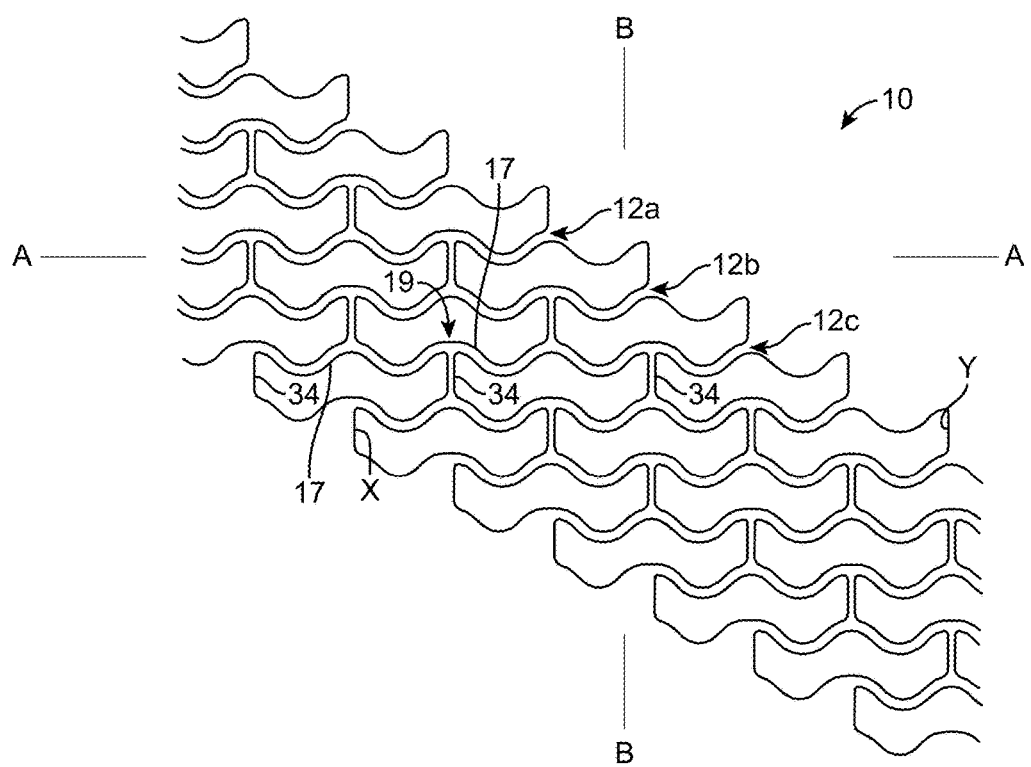
FIG. 1 describes a pattern for a scaffold crimped to a balloon. The scaffold is illustrated as a pattern. Each ring has 6 crowns and rings are connected to adjacent rings by 3 links. Each link is separated by 120 degrees. The drawing is a planar view showing the repeating pattern. An end of the stent is shown on the left. The rings 12 circumscribe a bore or the stent. To help with visualizing the tubular structure described by this pattern, note the link "x" is the same strut as link "y".

For purposes of this disclosure, the following terms and definitions apply:

The terms "about" or "approximately" mean 30%, 20%, 15%, 10%, 5%, 4%, 3%, 2%, 1.5%, 1% between 1-2%, 1-3%, 1-5%, or 0.5%-5% less or more than, less than, or more than a stated value, a range or each endpoint of a stated range, or a one-sigma, two-sigma, three-sigma variation from a stated mean or expected value (Gaussian distribution). For example, d1 about d2 means d1 is 30%, 20%, 15%, 10%, 5%, 4%, 3%, 2%, 1.5%, 1%, 0% or between 1-2%, 1-3%, 1-5%, or 0.5%-5% different from d2. If d1 is a mean value, then d2 is about d1 means d2 is within a one-sigma, two-sigma, or three-sigma variance from d1.

It is understood that any numerical value, range, or either range endpoint (including, e.g., "approximately none", "about none", "about all", etc.) preceded by the word "about," "substantially" or "approximately" in this disclosure also describes or discloses the same numerical value, range, or either range endpoint not preceded by the word "about," "substantially" or "approximately."

"Amorphous" or "substantially amorphous" means no greater than, or less than 5% crystallinity, or not more than 1%, 2% or 4% crystallinity.

The "degree of crystallinity" may be expressed in terms of, $w_c$ (mass fraction), $\varphi_c$ (volume fraction) and refers to mass fraction or volume fraction of crystalline phase in a sample of polymer. The mass-fraction and the volume-fraction degrees of crystallinity are related by the equation, $w_c = \varphi_c \, \rho/\rho_c$, where $\rho$ and $\rho_c$ are the mass concentrations (mass densities) of the entire sample and of the crystalline phase, respectively. The degree of crystallinity can be determined by several experimental techniques. Among the most commonly used are: (i) x-ray diffraction, (ii) calorimetry (DSC), (iii) mass density measurements, (iv) infrared spectroscopy (IR), (v) solid-state NMR spectroscopy, and (vi) vapor permeability. Unless stated otherwise, throughout this description a degree of crystallinity given for a polymer is expressed as a percentage (%) of crystallinity and expressed as a mass or volume fraction. Unless stated otherwise throughout this description a degree of crystallinity given for a polymer composition is expressed as a percentage (%) of crystallinity and expressed as a mass fraction.

Measurements of crystallinity may also be determined from a modified method of differential scanning calorimetry (DSC), e.g., over a temperature range of 30 Deg. C. to 150 Deg. C., with modulation amplitude of 0.5° C. and heat rate of 6° C./minute and duration of 1 minute. Curves for reversible and irreversible heat flow were obtained. Normalized enthalpies of cold crystallization and re-crystallization may be calculated from exotherms visible on an irreversible heat flow curve, while normalized enthalpy of melting is obtained from integration of an endotherm on a reversible heat flow curve. For example, percentage crystallinity may be calculated using EQ. 1:

$$\% \text{ Crystallinity} = (\Delta h1 - (\Delta h2 + \Delta h3))/(\Delta h4) \qquad \text{EQ. 1.}$$

Where
$\Delta h1$ is the enthalpy of melting;
$\Delta h2$ is the enthalpy of cold crystallization;
$\Delta h3$ is the enthalpy of recrystallization; and
$\Delta h4$ is the enthalpy of fusion for 100% crystalline material A "stent" means a permanent, durable or non-degrading structure, usually comprised of a non-degrading metal or metal alloy structure, generally speaking, while a "scaffold" means a temporary structure comprising a bioresorbable or biodegradable polymer, metal or combination thereof and capable of radially supporting a vessel for a limited period of time, e.g., 3, 6 or 12 months following implantation. It is understood, however, that the art sometimes uses the term "stent" when referring to either type of structure.

"Inflated diameter" or "expanded diameter" refers to the diameter the scaffold attains when its supporting balloon is inflated to expand the scaffold from its crimped configuration to implant the scaffold within a vessel. The inflated diameter may refer to a post-dilation balloon diameter which is beyond the nominal balloon diameter, e.g., a 6.5 mm balloon has about a 7.4 mm post-dilation diameter, or a 6.0 mm balloon has about a 6.5 mm post-dilation diameter. The nominal to post dilation ratios for a balloon may range from 1.05 to 1.15 (i.e., a post-dilation diameter may be 5% to 15% greater than a nominal inflated balloon diameter). The scaffold diameter, after attaining an inflated diameter by balloon pressure, will to some degree decrease in diameter due to recoil effects related primarily to, any or all of, the manner in which the scaffold was fabricated and processed, the scaffold material and the scaffold design.

"Post-dilation diameter" (PDD) of a scaffold refers to the diameter of the scaffold after being increased to its expanded diameter and the balloon removed from the patient's vasculature. The PDD accounts for the effects of recoil. For example, an acute PDD refers to the scaffold diameter that accounts for an acute recoil in the scaffold.

A "pre-crimp diameter" means an OD of a tube, or the scaffold before it is crimped to a balloon. Similarly, a "crimped diameter" means the OD of the scaffold when crimped to a balloon. The "pre-crimp diameter" can be 2, 2.5, 3.0 times greater than the crimped diameter and about 0.9, 1.0, 1.1, 1.3 and about 1-1.5 times higher than an expanded diameter or post-dilation diameter. Crimping, for purposes of this disclosure, means a diameter reduction of a scaffold characterized by a significant plastic deformation, i.e., more than 10%, or more than 50% of the diameter reduction is attributed to plastic deformation, such as at a crown in the case of a stent or scaffold that has an undulating ring pattern, e.g., FIG. 1. When the scaffold is deployed or expanded by the balloon, the inflated balloon plastically deforms the scaffold from its crimped diameter. Methods for crimping scaffolds made according to the disclosure are described in US20130255853.

"Recoil" means the response of a material following the plastic/inelastic deformation of the material. When the scaffold is radially deformed well beyond its elastic range and the external pressure (e.g., a balloon pressure on the luminal surface) is removed the scaffold diameter will tend to revert back to its earlier state before the external pressure was applied. Thus, when a scaffold is radially expanded by applied balloon pressure and the balloon removed, the scaffold will tend to return towards the smaller diameter it had, i.e., crimped diameter, before balloon pressure was applied. A scaffold that has recoil of 10% within ½ hour following implantation and an expanded diameter of 6 mm has an acute post-dilation diameter of 5.4 mm. The recoil effect for balloon-expanded scaffolds can occur over a long period of time. Post-implant inspection of scaffolds shows that recoil can increase over a period of about one week following implantation. Unless stated otherwise, when reference is made to "recoil" it is meant to mean recoil along a radial direction (as opposed to axial or along longitudinal direction) of the scaffold.

"Acute Recoil" is defined as the percentage decrease in scaffold diameter within the first about ½ hour following implantation within a vessel.

The "glass transition temperature," Tg, is the temperature at which the amorphous domains of a polymer change from a brittle vitreous state to a solid deformable or ductile state at atmospheric pressure. In other words, the Tg corresponds to the temperature where the onset of segmental motion in the chains of the polymer occurs. When an amorphous or semi-crystalline polymer is exposed to an increasing temperature, the coefficient of expansion and the heat capacity of the polymer both increase as the temperature is raised, indicating increased molecular motion. As the temperature is increased, the heat capacity increases. The increasing heat capacity corresponds to an increase in heat dissipation through movement. Tg of a given polymer can be dependent on the heating rate and can be influenced by the thermal history of the polymer as well as its degree of crystallinity. Furthermore, the chemical structure of the polymer heavily influences the glass transition by affecting mobility. The Tg can be determined as the approximate midpoint of a temperature range over which the glass transition takes place. [ASTM D883-90]. The most frequently used definition of Tg uses the energy release on heating in differential scanning calorimetry (DSC). As used herein, the Tg refers to a glass transition temperature as measured by differential scanning calorimetry (DSC) at a 20° C./min heating rate. Unless stated otherwise, values for "Tg" refer to an upper limit for Tg (E.g., for poly(L-lactide) and the Tg when the material is dry. Poly(L-lactide) has a glass transition temperature range of between about 55 to 60 Deg. C. "Tg" for poly(L-lactide), for purposes of this disclosure, Tg is 60 Deg. C), or up to 65 Deg. C. for a strain hardened tube. The glass transition temperature is a function of chain flexibility. The glass transition occurs when there is enough vibrational (thermal) energy in the system to create sufficient free-volume to permit sequences of 6-10 main-chain carbons to move together as a unit. At this point, the mechanical behavior of the polymer changes from rigid and brittle to tough and leathery.

The "melting temperature" (Tm) is the temperature at which a material changes from solid to liquid state. In polymers, Tm is the peak temperature at which a semicrystalline phase melts into an amorphous state. Such a melting process usually takes place within a relative narrow range (<20° C.), thus it is acceptable to report Tm as a single value.

A "Solid Phase Process" or "Solid Phase Processing" means a process for strain-hardening a material using a die, where the plastic deformation of the material occurs at temperatures close to, and above the Tg of the material. "Close to, and above the Tg of the material" means the temperature of the material worked, and/or the die have temperatures of between about 10 to 30 Deg. C. above the upper limit of Tg, about 15 to 25 Deg. C. above the upper limit of Tg, about 10 to 20 Deg. C. above the upper limit of Tg, or about 15 to 20 Deg. C. above the upper limit of Tg.

"Molecular weight" refers to either number average molecular weight (Mn) or weight average molecular weight (Mw). References to molecular weight (MW) herein refer to either Mn or Mw, unless otherwise specified. The Mn may be as measured by GPC-RI Gel Permeation Chromatography with refractive index detection relative to polystyrene standards. Suitable mobile phase solvents are acetone, tetrahydrofuran, chloroform, 1,1,1-trichloroethane, 2,2,2-trifluoroethanol, and hexafluoro-2-propanol.

"Stress" refers to force per unit area, as in the force acting through a small area within a plane within a subject material. Stress can be divided into components, normal and parallel to the plane, called normal stress and shear stress, respectively. Tensile stress, for example, is a normal component of stress that leads to expansion (increase in length) of the subject material. In addition, compressive stress is a normal component of stress resulting in compaction (decrease in length) of the subject material.

"Strain" refers to the amount of expansion or compression that occurs in a material at a given stress or load. Strain may be expressed as a fraction or percentage of the original length, i.e., the change in length divided by the original length. Strain, therefore, is positive for expansion and negative for compression.

"Modulus" may be defined as the ratio of a component of stress or force per unit area applied to a material divided by the strain along an axis of applied force that result from the applied force. For example, a material has both a tensile and a compressive modulus.

"Toughness", or "fracture toughness" is the amount of energy absorbed prior to fracture, or equivalently, the amount of work required to fracture a material. One measure of toughness is the area under a stress-strain curve from zero strain to the strain at fracture. The stress is proportional to the tensile force on the material and the strain is proportional to its length. The area under the curve then is proportional to the integral of the force over the distance the polymer stretches before breaking. This integral is the work (energy) required to break the sample. The toughness is a measure of the energy a sample can absorb before it breaks. There is a difference between toughness and strength. A material that is strong, but not tough is said to be brittle. Brittle materials are strong, but cannot deform very much before breaking.

As used herein, the terms "axial" and "longitudinal" are used interchangeably and refer to a direction, orientation, or line that is parallel or substantially parallel to the central axis of a stent or the central axis of a tubular construct. The term "circumferential" refers to the direction along a circumference of the stent or tubular construct. The term "radial" refers to a direction, orientation, or line that is perpendicular or substantially perpendicular to the central axis of the stent or the central axis of a tubular construct and is sometimes used to describe a circumferential property, i.e. radial strength.

The term "crush recovery" is used to describe how the scaffold recovers from a pinch or crush load, while the term "crush resistance" is used to describe the force required to cause a permanent deformation of a scaffold. A scaffold or stent that does not possess good crush recovery does not substantially return to its original diameter following removal of a crushing force. A scaffold or stent having a desired radial force can have an unacceptable crush recovery. And a scaffold or stent having a desired crush recovery can have an unacceptable radial force. Crush recovery and crush resistance aspects of scaffolds are described in greater detail in US20110190871. Crush recovery may be expressed with reference to the un-deformed diameter of the scaffold, e.g., an applied 25% crush and resulting 80% recovery means the scaffold when crushed (or pinched) by a magnitude equal to 25% of the scaffold's un-deformed diameter recovers up to only 80% of its un-deformed diameter after the crushing or pinching force is removed.

An expansion capability of a scaffold refers generally to the ability of or degree a scaffold can be expanded without failure. The degree may be quantified by the maximum diameter that the scaffold may be deformed or expanded without failure or the diameter at which the scaffold fails. The expansion capability may be inferred from a "Max Expansion" value (EQ. 1, infra) or a post-dilation-to-fracture test.

A "Ring test" (or "Ring Tension test") evaluates the capacity of a scaffold to sustain tension forces up until a point of total failure in one or more struts, typically a ring strut. The Ring test is sometimes thought of as an indicator of the dilation capacity of a scaffold. An alternative test for measuring the fitness of a scaffold ring is called a post-dilation-to-fracture test. This test directly measures a maximum expanded diameter of a scaffold up until failure using balloons. According to the post-dilation-to-fracture test a scaffold is expanded on progressively larger balloons while watching for the first fracture, usually of a ring. The recorded test output for the post-dilation-to-fracture test is then the expanded inner-diameter of the rings just prior to the first ring fracture.

The Ring test also seeks to evaluate the fitness of a scaffold to sustain high radial loads. The Ring test apparatus, however, applies an altogether different type of loading on the scaffold than the post-dilation-to-fracture test. Rather than expanding the scaffold using outwardly-directed radial pressure, e.g., an expanding balloon, the Ring test instead uses a pair of cylindrical or semi-cylindrical pins or mandrels disposed within the scaffold to load the scaffold. The mandrels are pulled apart, thereby deforming the scaffold from a circular cross-section to an oval-shaped cross-section as the scaffold deforms. The incremental relative displacement between the mandrels is measured as the mandrels are pulled apart. The point at which an oval-shaped ring (indeed, the ring is deformed into a shape resembling more a rectangle with semicircular ends) fails is thought of as equivalent or analogous to a maximum diameter that the ring can sustain when subjected to a radial-outward load. The equation relating the displacement of the mandrels relative to one-another and the point of failure for the equivalent outer diameter ("Max Expansion") is given below, $$\text{Max Expansion} = (2/\pi) * [(1/2)Cp + D + 2f + g + (x-s)] \quad \text{EQ. 1}$$

Where
Cp is the measured circumference of a mandrel
D is the diameter of a mandrel
f is the scaffold wall thickness
x is the extension distance at failure g is the initial distance between the mandrels (scaffold unloaded)

s is the extension distance of one recorded data step.

If one wishes to calculate the maximum expansion inner, rather than outer diameter (EQ. 1), subtract $(4/\pi)*f$ from the Max Expansion value or omit the "f" term (wall thickness) from EQ. 1. Ring tests conducted on scaffolds used an Instron® Materials Testing Apparatus (Model 5543 or 5544). The test procedure for a scaffold included the following steps. The scaffold is received crimped to a balloon of a balloon catheter. The scaffold is deployed on the balloon to the rated burst pressure in water at body temperature. After deployment, the scaffold is loaded on to the two mandrels, mounted on the materials testing machine and submerged in a water bath heated to body temp. The scaffold is then deformed by pulling one of the mandrels away from the other mandrel until a strut fracture is detected. The rate of displacement of one mandrel relative to the other mandrel is 0.1 in/min, which is deemed equivalent to a balloon inflation rate of 2 atm/5 sec.

A "radial strength test" measures the radial compressive pressure required to exceed the radial strength of the scaffold. Radial strength tests were conducted on scaffolds using an MSI RX550 Radial Force Tester. Using this machine the scaffold is compressed circumferentially to a specified end diameter and compression dies within the tester record the radial force/pressure as a function of diameter. The rate of compression is 0.02 mm/sec. The scaffold is received crimped to a balloon of a balloon catheter. The scaffold is deployed on the balloon to the rated burst pressure in water at body temperature. The scaffold is compressed in air at body temperature. The radial yield strength is found from a computed modulus vs. diameter curve, which is calculated and reported as the radial stiffness. The radial strength is then reported as the maximum pressure (e.g., in millimeters of Mercury, abbreviated as "mm Hg") between the start of compression and where a 0.1 mm offset to the modulus intersects the pressure vs. diameter curve.

"Shortly," for purposes of this disclosure, includes less than about 24 hours, between about 0 and 8 hours, about 0 to 10 minutes, about 0 to 20 minutes and less than about 1 hour, 10 to 30 seconds, 1 to 10 minutes, 10 min to 1 hr, 1 to 8 hr, 8 hr to 12 hr, and 12 hr to 1 day. The word "shortly" is used to refer to the approximate time period elapsed between when a tube or scaffold is placed into a thermodynamic non-equilibrium state or transient state and when the scaffold is crimped to a balloon. For example, a thermal or mechanical treatment to rejuvenate the scaffold takes place shortly before crimping according to the embodiments; or crimping takes place shortly after a scaffold or tube processing step that imparts a desired material memory prior to crimping. Thus, according to some embodiments crimping takes place within a day of a forming process or thermal treatment, which raised the scaffold temperature to about Tg or above Tg, and/or imposed a mechanical strain beyond a yield strain. This period reflects test results showing a consistent loss/improvement in radial strength and/or Max Expansion capability of scaffolds crimped within one day vs. more than one day from a forming process, e.g., a blow-molding of an extruded tube above the glass transition temperature for the polymer.

Scaffold Damage Due to Crimping

Balloon-expanded scaffolds are subjected to significant plastic deformation during manufacture when crimped down to a delivery diameter to achieve the desired crossing-profile. The scaffold is again subjected to significant plastic deformation when deployed or expanded from the delivery diameter to the expanded, inflated or post-dilation diameter. Polymers used to make polymer scaffolds may be susceptible to fracture at the conditions of crimping and deployment. As a result, vascular scaffolds are susceptible to damage due to fracture mechanisms during manufacture (particularly during crimping), deployment, and use. Damage, e.g., at crowns for scaffolds having undulating rings, caused by the crimping process decreases the radial strength of the scaffold at the inflated, expanded or post-dilatation diameters. Thus, fracture resistance of the scaffold at crimping is crucial to the ultimate performance of the scaffold at deployment. Improving the fracture toughness or ductility of a scaffold (while not negatively affecting the scaffold's radial strength) pre-crimping is important in order to reduce material-level damage during crimping and in vitro/in vivo deployment of a bioresorbable scaffold.

In the case of scaffolds that have undulating rings interconnected by links, crests or bends in the scaffold are subjected to significant deformation or material strain during crimping and deployment. During crimping, the outer portion of a crest is subjected to high tensile strain and the inner portion is subjected to high compressive strain. During expansion or deployment, the reverse is the case. The inventors have observed significant material level damage at the crests in crimped scaffolds. The damage is can be highly localized and particularly severe, for example, at the inner crest on the inner and outer surfaces of the strut and the side wall surfaces of the strut.

The damage observed using techniques such as scanning electron microscopy (SEM), polarized light microscopy, and small angle X-ray scattering (SAXS) includes crazing and fracture or micro-cracks. Crazing is a precursor to cracks and includes two separated surfaces spanned by many small fibrils with diameters in the range of 5-30 nm.

There is a continuing need to develop new processing methods for scaffolds that improve the resistance to fracture while retaining a relatively high radial strength. The reduced damage allows achievement of a sufficiently high radial strength with a reduced strut thickness, wall thickness and/or cross-section.

Tube Processing Prior to Crimping

According to the disclosure and described in greater detail below, three types of processes are contemplated for avoiding the crimping of an aged polymer scaffold to a balloon: just-in-time, freezing, and rejuvenation. Prior to crimping the polymer scaffold is formed by a process (hereinafter "forming process") that raises the polymer temperature to, or above its glass transition temperature and/or subjects the material to a mechanical strain beyond its yield strain. Examples of forming processes include extrusion of a polymer tube, biaxial stretching of a polymer sheet that is later formed into a tube, blow-molding an extruded polymer tube and necking or strain hardening by die drawing. Combinations of these processes are also contemplated and within the scope of a "forming process" according to the disclosure. For example, a scaffold may be laser cut from an extruded tube that was first blow-molded then die drawn to improve its radial strength properties.

During and shortly after the forming process the material is in a thermodynamically unstable state where molecular structures comprising polymer chains are able to move relatively easily relative to one another. After a period of time has elapsed, e.g., 24 hours later, the material has moved to a more thermodynamically stable state as a relaxation of enthalpic interactions has taken place, and/or the free volume between molecular regions decreases, thereby limiting the ability of polymer chains to move freely relative to one another. This ageing, as such, makes it less possible for the material to everywhere sustain the high strains associated with crimping.

Stated from a somewhat different perspective, ageing can make a material stronger and stiffer, but also more brittle or less ductile, which means the scaffold when crimped is less capable of sustaining high strains. Or the material's elongation at break during crimping is less than it would have been if crimping occurred before ageing. As a result, structural integrity is lost as micro-fractures/voids form in the material when the scaffold is crimped. These micro-fractures (or cracks) and voids can propagate into larger cracks/voids when the scaffold is expanded by the balloon. As a consequence, a scaffold's radial strength at deployment is generally significantly reduced from its radial strength prior to crimping (Indeed, the radial strength of a scaffold deployed from a crimped state can be reduced by up at two times that of the scaffold prior to crimping).

Just-in-Time Processing

According to some embodiments the scaffold is crimped to a balloon shortly after one of the forming processes has taken place. The word "shortly" is defined supra.

Rejuvenation/Erase Ageing

According to some embodiments a scaffold is thermally treated, mechanically strained, or solvent treated to induce a rejuvenation or erasure of ageing in a polymer shortly before crimping the scaffold to a balloon. Rejuvenation erases or reverses changes in physical properties caused by physical ageing by returning the polymer to a less aged or even an unaged state. Physical ageing causes the polymer to move toward a thermodynamic equilibrium state, while rejuvenation moves the material away from thermodynamic equilibrium. Therefore, rejuvenation may modify properties of a polymer in a direction opposite to that caused by physical ageing. For example, rejuvenation may decrease density (increase specific volume) of the polymer, increase elongation at break of the polymer, decrease modulus of the polymer, increase enthalpy, or any combination thereof. The inventors have found that rejuvenation may also modify scaffold properties such as increase radial strength of the scaffold, fatigue life where stress concentrates in the structure during typical loading, increase expansion capability of the scaffold, reduce damage to the scaffold at crimping, or any combination thereof.

According to some embodiments, rejuvenation is desired for reversal or erasure of physical ageing of a polymer that was previously processed. Rejuvenation is not however intended to remove, reverse, or erase memory of the previous processing steps. Therefore, rejuvenation also does not educate or impart memory to a scaffold or tube. Memory may refer to transient polymer chain structure and transient polymer properties provided by previous processing steps. This includes processing steps that radially strengthen a tube from which a scaffold is formed by inducing a biaxial orientation of polymer chains in the tube as described herein.

For example, a scaffold is laser cut from a blow-molded tube. Just before crimping a rejuvenation process is performed to erase or undo ageing that may have occurred since the time of the forming process. This rejuvenation process, initiated at the time of, during, or shortly before crimping, may be combined with one or both of the freezing or just-in-time embodiments as needed or desired. For example, within a 24-48 hour period, a scaffold is made by a forming process, frozen after it has been laser cut and coated with a polymer-drug combination, thawed, then heated and/or radial expanded just prior to, or during crimping.

It will be appreciated that embodiments where a scaffold is frozen shortly after the forming process (freezing embodiment) or where crimping is done shortly after the forming process (just-in-time embodiment) can introduce several complications relating to the concurrent implementation of several distinct processing steps associated with the manufacture a drug-eluting polymer scaffold following a forming process. For instance, it will be appreciated that a scaffold process may include the following steps, several of which require separate environments/conditions for scaffold processing:

a) Biaxial expansion of the extruded polymer tube, e.g., by blow-molding;
b) Laser cutting of the scaffold pattern from the polymer tube;
c) Cleaning and Inspection of the scaffold cut from the tube;
d) Coating the scaffold with a polymer or drug-polymer composition; and
e) Crimping.

Step a) above is the forming process. Thus, without adding an additional processing step while also avoiding any significant ageing from the time of step a) until step e) (crimping), one needs to perform steps b), c) and d) shortly after the forming process. Freezing the scaffold, e.g., immediately after inspecting and cleaning the cut scaffold (step c)), may make it more feasible to accomplish all processing steps while avoiding material ageing; nonetheless, proceeding in this fashion does not obviate all of the potential difficulties associated maintaining a non-equilibrium state within the material, i.e., preventing the material from ageing. Typically at least a day goes by between cutting and cleaning the scaffold and coating. In some embodiments the scaffold temperature is reduced (e.g., from ambient temperature to about −20 Deg. C.) in order to reduce the rate of ageing. Then a later time, e.g., within a few days, or a week of freezing.

Thermal Rejuvenation

Thermal rejuvenation (including thermal treatment of a bioresorbable scaffold above Tg, but below melting temperature (Tm) of the polymer scaffold) prior to a crimping process may reverse or remove the physical ageing of a polymeric scaffold, which may reduce crimping damage (e.g., at the crests of a scaffold). As a consequence, radial strength, expansion capability, and/or fatigue life are improved.

The inventors have surprisingly found that thermal treatment of the scaffold prior to crimping can improve the scaffold performance in terms of radial strength, maximum expansion capability, or both. The inventors have demonstrated that thermal treatment of a scaffold prior to crimping reduces the radial strength loss due to deformation during crimping. It is hypothesized that exposing the scaffold to a temperature higher than its glass transition temperature for a short period of time rejuvenates the polymer chains, thus making the polymer more malleable to crimp deformation, yet without a concomitant reduction in radial strength or stiffness. The thermal treatment at least in part reverses or reduces the effects of physical ageing. As a result, there is reduced damage to the scaffold as the scaffold is crimped. When the thermally treated scaffold is deployed it has a higher radial strength in the deployed state due to the reduced damage occurring during crimping. Non-exclusive examples of such heat treatment are discussed below.

The effects of physical ageing on material properties of the scaffold polymer can include decrease in specific volume (increase in density), increased stiffness, increased strength, decreased toughness, and decrease in elongation at break. Properties such as entropy, enthalpy, and rate of segmental dynamics of a polymer chains all decrease as the sample ages.

Changes in scaffold properties caused by physical ageing can be at least partially reversed by heating above a polymer's glass transition temperature Tg and without removing the memory of prior processing steps, e.g., prior induced biaxial orientation of polymer chains. The thermal treatment may, therefore, rejuvenate the scaffold towards or to an unaged state. In particular, the thermal treatment may result in any one of, or a combination of effects on the scaffold polymer: increase in specific volume (decrease in density), a decrease in modulus, decrease in strength, an increase in fracture toughness, and an increase in elongation at break. In general, the thermal treatment process changes transient properties that are reversible under specified conditions and time frame.

The rejuvenated scaffold may further have improved scaffold properties as compared to the aged scaffold. In particular, the radial strength, radial stiffness, fatigue life, and/or expansion capability may be increased by the thermal treatment. In some cases, the radial strength may be increased and the expansion capability may be decreased. In such cases, the reduced crimping damage due to the rejuvenation process may be sufficient to increase radial strength at deployment, however, insufficient to increase maximum expansion capability due to damage resulting from expansion of the scaffold to failure.

As compared to the aged scaffold, the radial strength may be increased by 5 to 10%, 10 to 20%, 20 to 30%, or greater than 30%. The expansion capability may be increased by 5 to 10%, 10 to 20%, 20 to 30%, or greater than 30%. Alternatively, the expansion capability may decrease by 1 to 5%, 5 to 10%, or by greater than 10%.

Since the properties modified by the thermal treatment are transient, it is believed that after thermal processing physical at ambient conditions may reverse the effects of the thermal processing over time. Therefore, the time period or delay between thermal treatment and crimping should be short enough that all or at least some of the rejuvenated properties are preserved. The degree of improvement of scaffold properties of radial strength and/or expansion capability may be a function of the time period between rejuvenation and crimping. In particular, a radial strength increase may decrease as the time period between rejuvenation and crimping increases.

The primary process parameters of the thermal treatment process are the temperature and the treatment time. The temperature is the temperature of exposure to the scaffold or the scaffold temperature. The treatment time is the time of the temperature exposure or time the scaffold is at the treatment temperature. At the end of the treatment time the temperature exposure or the temperature is reduced to ambient temperature or below ambient temperature. According to some embodiments the scaffold temperature is then not raised above Tg before crimping. The treatment temperature is sufficiently above Tg of the scaffold polymer to cause reversal of physical ageing or rejuvenation as described. Additionally, the treatment time is sufficient to cause reversal of physical ageing or rejuvenation sufficient to produce improved mechanical properties in the scaffold upon deployment form the balloon. The treatment temperature and treatment time may be adjusted to obtain a desired degree of rejuvenation, for example, a desired degree in changes to the scaffold. In some cases the amount of rejuvenation that takes place may be understood as being principally a function of the amount of energy put into the scaffold, or the heat transfer, which is determined by a combination of the treatment temperature and time, or the rate at which the scaffold absorbs heat. For example, the higher the temperature the lower the treatment time required and the longer the treatment time the lower the temperature may result in about the same amount of rejuvenation.

As indicated above, thermal treatment according to the invention does not remove or erase all memory of previous processing steps so the thermal treatment is performed in a manner that preserves or maintains at least some of, e.g., an induced biaxial orientation and resulting increased radial strength. Thus, the treatment time and temperature are selected so as not to erase memory of such processing steps, such as an induced polymer chain orientation.

Thermal treatment may include exposing a scaffold to a treatment temperature in a temperature range from Tg to below the Tm of the scaffold polymer for a selected treatment time. More narrowly, the treatment temperature may be between about 10° C. above its Tg and (Tg+Tm)/2. More narrowly, the temperature range is about Tg to Tg+10° C., Tg to Tg+20° C., Tg to Tg+30° C., Tg to Tg+40° C., Tg+10° to Tg+20° C., Tg+10° to Tg+30° C., Tg+20° to Tg+30° C., Tg+20° to Tg+40° C., or greater than about Tg+30° C., but less than Tm.

For a scaffold polymer composition including greater than 90 wt % or 95% PLLA or lactide monomer content (i.e., lactide-based polymer), the treatment temperature may be about 60 to 80° C., 65 to 70° C., 70 to 75° C., 75 to 80° C., 85 to 90° C., 60 to 90° C., 60 to 90° C., or 60 to 100° C., provided that material memory is not erased. Thermal treatment may have a temperature ramp. Specifically, there may be a rapid increase in temperature of the scaffold from a lower temperature to the target thermal treatment temperature. For example, the heating rate may be 1-3° C./sec, 3-5° C./sec, 5-10° C./sec, or greater than 10° C./sec. Moreover, the temperature cannot be too low since this may result in accelerated physical aging.

The thermal treatment time may be about 10 s to 60 min, 10 s to 1 min, 1 to 5 min, 5 to 15 min, 15 to 30 min, 30 to 45 min, or 45 to 60 min, or greater than about 60 min, provided that material memory is not erased.

The scaffold may have no or minimal change in diameter during the thermal treatment. The scaffold diameter may be maintained at a fixed diameter during the thermal processing. For example, the scaffold may be disposed over a mandrel that prevents a reduction in diameter during the thermal processing. There may be no external force, such as radially inward or radially outward, applied to the scaffold sufficient to change the diameter of scaffold during thermal treatment. For example, the scaffold may not be expanded or contracted during thermal treatment.

The thermal treatment may be performed with a variety of methods. These methods include heating in an oven, microwave oven, electrical heating with a wire disposed through the scaffold lumen, passing a heated heat transfer fluid through lumen of scaffold, blowing a heating gas from a nozzle while the scaffold is disposed on a mandrel, radiofrequency (RF) induction, and infrared heating (e.g., infrared lamp). The scaffold heating in the oven may be in air, inert gas such as nitrogen or argon, or vacuum.

The scaffold may be thermally treated at various points in the manufacturing process: after laser cutting and before coating, during the coating, after coating and before crimping, or any combination thereof. The manufacturing process may also include other manufacturing steps between laser cutting and coating, laser cutting and crimping, and coating and crimping. For example, radiopaque markers may be installed after laser cutting and before coating. Additionally, there may be no coating step so that an uncoated scaffold is crimped after laser cutting or some processing step performed after laser cutting.

Freezing to Delay Ageing

As an alternative to crimping shortly after thermal treatment, the scaffold may be frozen to prevent or reduce physical ageing and loss of rejuvenation. The temperature of frozen storage may be less than 0° C., 0 to −4° C., −4 to −10° C., −10 to −20° C., or less than −20° C. After any freezing step, the scaffold may be stored for a period of time. This step then allows manufacturing to have a variable work in process time. For example, a frozen scaffold may be stored 1 day to 1 week, 1 to 2 weeks, 2 weeks to 1 month, or greater than a month.

When crimping of the scaffold is to be performed after the frozen storage, the frozen scaffolds may be removed from the freezer, allowed to equilibrate (thaw) to ambient temperature and then crimped immediately shortly after equilibration. The time between equilibration or after removal from the freezer to ambient temperature and crimping may be 10 s to 1 min, 1 to 10 min, 10 min to 1 hr, 1 to 8 hr, 8 hr to 12 hr, or 12 hr to 1 day. The thawed scaffold may have no or minimal loss of rejuvenation after thawing to room temperature. The time between thawing and crimping can be less than 8 hr, 1 to 8 hr, 1 to 3 hr, 3 to 5 hr, or 5 to 8 hr.

Several alternatives when freezing and thawing is employed to preserve rejuvenation include, but is not limited to: (1) the scaffold may be thermally treated prior to coating, frozen, thawed, coated, and then shortly after crimped; (2) the scaffold is thermally treated prior to coating, frozen, thawed, coated, frozen, again, thawed, and then shortly after crimped; (3) the scaffold is thermally treated prior to coating, frozen, thawed, coated, frozen again, thawed, and then shortly after crimped; (4) the scaffold is thermally treated during coating, frozen, thawed, and then shortly after crimped; and (5) the scaffold is thermally treated after coating, frozen, thawed, and then shortly after crimped.

Drug Sensitivity/Coating

Therapeutic agents or drugs may susceptible to degradation when exposed sufficiently high temperatures. For example, drugs may suffer from chemical degradation above temperature between 80 to 100° C. In particular, some drugs may be subject to oxidative degradation. Therefore, the thermal treatment may be integrated into a stent fabrication process in a way that reduces or eliminates the risk of drug degradation.

For example, thermal treatment after drug coating may be performed in a vacuum or inert gas environment. These environments may avoid potential oxidative drug degradation due to heat. Another approach is to perform the heat treatment in a vacuum oven to prevent oxidative drug degradation.

Another way to avoid drug oxidation is to perform thermal treatment of a scaffold prior to forming a drug coating. Shortly or immediately after the heat treatment, drug coat process is performed, followed shortly thereafter by the crimping process. Alternatively, as described above, the scaffold can be frozen after the thermal treatment, stored, thawed, coated, and then crimped.

As discussed, thermal treatment can be performed during or as part of the coating process. Specifically, a heat treatment step may be incorporated into the coating process as part of a solvent removal step. In general, a coating on a stent may be formed by applying or depositing a coating composition including polymer dissolved in a solvent on the stent substrate, body, or scaffolding. The coating composition can optionally also include a therapeutic agent or drug or other substance, for example, a radiopaque agent. A coating composition can be applied to a scaffold by various methods, such as, dip coating, brushing, or spraying. In particular, spray coating a stent typically involves mounting or disposing a stent on a support, followed by spraying a coating composition from a nozzle onto the mounted stent. Solvent is removed from the deposited coating composition to form the coating. There typically is some residual solvent remaining in the coating after the solvent removal or solvent removal steps.

Solvent removal can be performed through a thermal treatment that includes heating or exposing a coated stent to a temperature above room temperature. The thermal treatment can be performed at a temperature and time sufficient to both remove solvent and reverse physical ageing effects of the scaffold substrate. The coating thermal treatment temperature can in any of the temperature ranges disclosed above. For example, the thermal treatment temperature can be 80 to 120° C., or more narrowly, 80 to 90° C., 80 to 90° C., 90 to 100° C., 100 to 110° C., and 110 to 120° C.

In order to provide uniform solvent removal, a coating of a target coating thickness (or mass) is preferably formed with two or more cycles or passes of a coating composition application, such as spraying. After each cycle or pass, a solvent removal or drying step is performed. The solvent removal step after each pass is referred to as interpass drying. A cycle or pass refers to the application of a coating composition without an intervening solvent removal step, such as blowing air or ambient or an inert gas that is at the treatment temperature on the stent. In spraying, a cycle or pass can include directing the spray plume over the length of a stent one or more times. After each coating composition application pass, the application of coating composition on the substrate is stopped, which is followed by interpass solvent removal. Such a process is described in US 2010/0323093.

In the present case, the interpass drying can be performed to both remove solvent and reverse physical ageing effects of the scaffold substrate. Some or all of the interpass drying steps can be performed at a time and temperature to reverse physical ageing. An interpass thermal treatment includes heating to or exposure of the scaffold to a treatment temperature for treatment time of 5 to 10 s, 10 to 15 s, 15 to 30 s, 30 to 60 s, 60 s to 2 min, or 2 to 5 min.

At the end of the interpass coating process, the scaffold may be subjected to no further solvent removal step, such as a baking step. Alternatively, at the end of the interpass coating process, the solvent may be subjected to a baking step in an oven in a vacuum, air, or inert gas environment. The thermal treatment time of the baking step may be 30 to 60 s, 60 s to 2 min, or 2 to 5 min at a treatment temperature of any of the temperature ranges disclosed.

Shortly or immediately after coating, the scaffold is crimped on the balloon catheter. Alternatively, the scaffold may be frozen immediately after coating and thawed later for crimping.

The thermal treatment of a scaffold may be performed with the scaffold positioned in a crimping apparatus. The scaffold is disposed within the bore of the crimping machine. In one embodiment, the thermal treatment may be performed by passing heated air or inert gas through the bore which may be turned on or off. In another embodiment, the crimper has jaws that define the bore which can rapidly vary in temperature to thermally treat the scaffold positioned therein. This may be accomplished with jaws that are hollow and contain a recirculating heat transfer fluid. The total volume of fluid in the circuit is small so that it may be thermally cycled rapidly. The jaws may also be heated electrically with a heating element.

Thermal treatment may also be performed before, or after, coating using a tunnel or conveyor oven. The conveyer may move the scaffolds through in a continuous fashion through the tunnel over oven. Thermal treatment time can be controlled by the conveyer speed. For example, for an oven or tunnel of length L and a conveyer speed C, the treatment time is L/C.

Solvent Rejuvenation

As an alternative to thermal treatment, physical ageing reversal and stress-strain relaxation of the scaffold can also be achieved by treatment of the scaffold with a solvent. When the scaffold solvent absorbs solvent, the solvent plasticizes the polymer. The solvent effectively lowering the Tg of the polymer which allows greater freedom of movement of the chains analogous to the effect of thermal treatment.

The solvent treatment may include exposing the scaffold to a liquid solvent by soaking, spraying, dipping, or brushing. The solvent treatment may also include solvent vapor exposure. The solvent vapor treatment may include disposing a scaffold on a mandrel which can be placed in a room temperature chamber filled with solvent vapor. The scaffold may be exposed to solvent liquid or vapor for 1 min to 12 hr, 12 hr to 1 day, or more narrowly, 1 to 5 min, 5 to 30 min 30 min to 1 hr, 1 hr to 5 hr, or 5 to 12 hr, or greater than 1 day.

After the solvent exposure, the solvent may then be removed from the scaffold by exposing the scaffold to a temperature above ambient. For example, the scaffold can be baked in an oven at a mild temperature for a suitable duration of time (e.g., 30 min to 4 hr) or by the application of warm air. The mild temperature may be 5° C. above ambient to Tg-5° C. For a lactide-based scaffold polymer the solvent removal temperature may be 40 to 50° C.

The scaffold may then be crimped shortly or immediately after solvent removal. Alternatively, the scaffold may be frozen immediately after solvent removal and thawed at later time and crimped immediately.

Examples of solvents include, but are not limited to, dimethylsulfoxide (DMSO), chloroform, acetone, water (buffered saline), xylene, methanol, ethanol, 1-propanol, tetrahydrofuran, 1-butanone, dimethylformamide, dimethylacetamide, cyclohexanone, ethyl acetate, methylethylketone, propylene glycol monomethylether, isopropanol, isopropanol admixed with water, N-methylpyrrolidinone, toluene, and any combination thereof.

A "solvent" for a given polymer can be defined as a substance capable of dissolving or dispersing the polymer or capable of at least partially dissolving or dispersing the polymer to form a uniformly dispersed mixture at the molecular- or ionic-size level. The solvent should be capable of dissolving at least 0.1 mg of the polymer in I ml of the solvent, and more narrowly 0.5 mg in 1 ml at ambient temperature and ambient pressure. A solvent for the solvent treatment may be capable of swelling, but not dissolving the polymer.

Forming Process and Scaffold

Scaffolds for TEST A and B were all made using the same processes and from the same material. Extruded tubes of about 100% Poly(L-lactide) (PLLA) and molecular weight of greater-than or equal to 66 kDa were biaxially expanded by a blow molding process. The parameters used for blow-molding for TEST A and B scaffolds are described in US20110066222, specifically within the processes described at paragraphs [0040], [0044]-[0062], [0064]-[0073] and FIGS. 2, and 3A-3D. A Summary of the parameters set forth therein are provided below in TABLE 1.

TABLE 1

| Parameters used in blow molding process (US20110066222) |
| --- |
| Tubing biaxially expanded inside of a heated mold. Tube heated to about 70 to 110 deg C. during expansion Ambient air cooling |

Thus, for TEST A, B and C the forming process is blow-molding where a polymer tube subjected to a temperature above Tg and biaxial strain beyond the yield strain of the material. The biaxially expanded tube size was 3.5 mm (outer diameter), with a wall thickness of 100 to 120 microns.

Scaffold Pattern

Following blow molding the expanded tubes were laser cut to form a scaffold pattern as illustrated in FIG. 1. The scaffold 10 has a pattern of rings 12a, 12b, 12c, etc. Each pair of adjacent rings 12 are inter-connected by three link struts 34. The links 34 are separated by 120 degrees and extend parallel to a longitudinal or bore axis of the scaffold 10. A ring 12 has struts 17 arranged to form an undulating pattern of 6 crests/troughs. Each link forms a Y-crown and W-crown and the pattern may be described as forming W-shaped, symmetric closed-cells (where the symmetry refers to the links that connect one W-shaped cell to adjacent cells). The wall thickness was between 100 and 120 microns. The scaffold 10 had a strut thickness of 0.007 to 0.0075 in (180 to 190 microns). The aspect ratio (AR) of strut to wall thickness for the scaffold was 1.5 to 1.9 or 1.5 to 1.8.

Figure 5A:
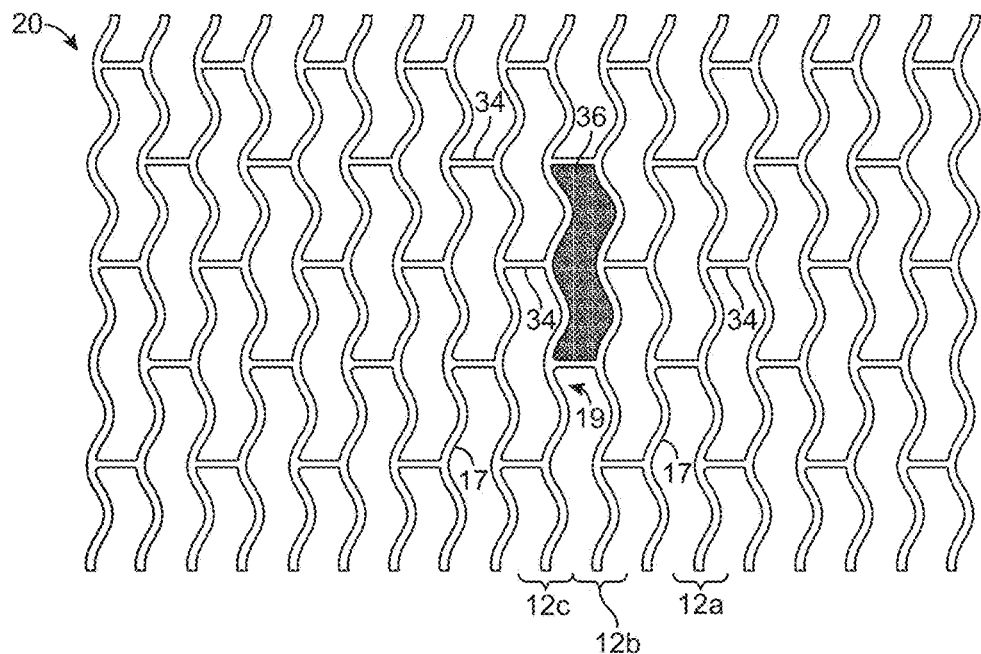
FIGS. 5A and 5B show other patterns for scaffolds that were evaluated during tests.
Figure 5B:
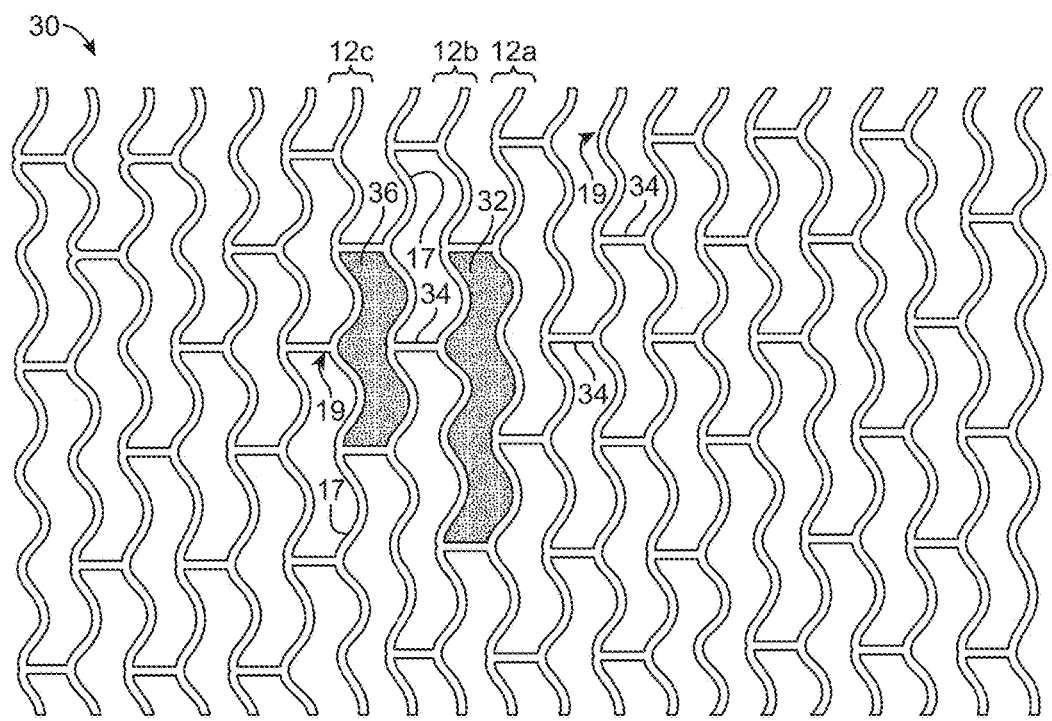

Referring to FIGS. 5A-5B there are shown two scaffold patterns 20 and 30, respectively. The scaffolds 20 and 30 each have a pattern of rings 12a, 12b, 12c, etc. Each pair of adjacent rings 12 are inter-connected by three link struts 34. Links 34 are separated by 120 degrees and extend parallel to a longitudinal or bore axis of the scaffold 10. A ring 12 has struts 17 arranged to form an undulating pattern of crests/troughs. Each link forms a Y-crown and a W-crown. There are 3 links, and 6 crests/troughs for each ring of scaffold 20 and 3 links, and 7 crests/troughs for each ring of scaffold 30. One difference between scaffolds 20 and 30 is the cell types formed. Scaffold 20 has everywhere W-shaped, symmetric closed-cells 36 as in the case of scaffold 10. Scaffold 30 however has an alternating pattern of W-shaped, symmetric closed-cells 36 and W-V-shaped asymmetric closed-cells 32 (where the asymmetry refers to the links that connect one W-V-shaped cell to adjacent cells). The wall thickness was between 88 and 100 microns, and 100 and 120 microns. The scaffolds 20 and 30 had a strut thickness of 0.007 to 0.0075 in (180 to 190 microns). The aspect ratio (AR) of strut to wall thickness for the scaffolds was 1 to 1.5, 1 to 2.2, and 1.4 to 2.2.

EXAMPLES

Various testing was completed to evaluate the effects of ageing on a scaffold crimping process and effectiveness of processes intended to crimp a scaffold while a polymer material is in a thermodynamically unstable state:

TEST A: Crimping of a scaffold with mechanical-strain method for rejuvenation

TEST B: Just-in-time—Crimping of a scaffold shortly after forming process

TEST C: Crimping of a scaffold with thermal method for rejuvenation

Crimping

Rejuvenation by mechanical strain (mechanical rejuvenation) and crimping before ageing tests on the constructed scaffold were the following:

Control (no radial expansion)—Group 1 scaffolds

Rejuvenation by radial expansion shortly before crimping—Group 2 scaffolds

Rejuvenation by radially expansion during crimping—Group 3 scaffolds

Crimping shortly after forming process—Group 4 scaffolds.

The forming processes for each of the scaffolds of took place more than one day prior to the mechanical rejuvenation. The crimping process for the control group of scaffolds is summarized in TABLE 2 (TABLE 2 also refers to the crimping process used for Group 4 scaffolds). The leftmost column indicates the programmed crimp-head diameter, which corresponds to about the outer diameter of the scaffold during crimping. The middle column shows the dwell periods where the crimp head diameter is held at a constant diameter, either to reach an equilibrium temperature or allow for stress relaxation within the material following a diameter reduction.

The scaffold was crimped in an iris crimper having metal blades with a polymer sheet disposed between the blades and scaffold surface when the scaffold was being crimped. The scaffold was pre-heated to about 48 Deg. C. before the scaffold diameter was reduced in size within the crimp head. The catheter balloon is inflated to a nominal inflation pressure for the balloon when the scaffold diameter is being reduced in size and during dwell periods. During the final stage where there is about 66% diameter reduction the balloon pressure is relieved or a vacuum drawn as the scaffold diameter gets near to the final programmed crimp diameter of about 0.041 in.

TABLE 2

Rejuvenation by Mechanical Strain (control/Group 1)

| Programmed Crimp head jaw diameter (in) | Dwell (sec) | Comments |
|---|---|---|
| .136 | 15 | Scaffold on 3.0 mm balloon catheter, 15 sec dwell within crimp head |
| .120 | 5 | about 12% diameter reduction, followed by 5 sec dwell. |
| Unit removed from crimp head, inspected, then returned to crimp head. | | |
| .120 | 15 | Scaffold on 3.0 mm balloon catheter, 15 sec dwell within crimp head |
| .041 | 165 | about 66% diameter reduction, followed by 165 sec dwell |

TABLE 3 and TABLE 4 show the crimping processes associated with the Rejuvenation by radial expansion shortly before crimping and Rejuvenation by radially expansion during crimping groups of scaffolds, respectively. The crimping process is the same for these two tests, except that, unlike the control group, the scaffolds were increased in diameter either just prior to, or during crimping.

Referring to TABLE 3, after the scaffold is heated to about 48 Deg. C. the scaffold diameter is increased by about 7%. The diameter increase is achieved using balloon pressure (while the scaffold is within the crimp head). The pressure was increased according to the balloon's compliance chart, which indicates the balloon outer diameter for different inflation pressures. After the 3.5 mm balloon was replaced by a 3.0 mm balloon catheter and the scaffold crimped in a manner similar to the process in TABLE 2, except that the scaffold was crimped from an about 7% larger diameter than the control group (0.146 in verses 0.136 in). Thus, according to the process of TABLE 3 in conjunction with the earlier forming process, in the example the scaffold diameter is increased over the expanded tube size at the time of the forming process.

TABLE 3

Rejuvenation by Mechanical Strain (radial expansion before crimp/Group 2)

| Crimp head jaw diameter (in) | Dwell (sec) | Comments |
|---|---|---|
| .136 | 15 | Scaffold on 3.5 mm balloon catheter, 15 sec dwell within crimp head |
| .146 | 5 | about 7% diameter increase, followed by 5 sec dwell. |
| Scaffold removed from crimp head, 3.5 mm balloon catheter replaced with 3.0 mm balloon catheter | | |
| .146 | 15 | Scaffold on 3.0 mm balloon catheter, 15 sec dwell within crimp head |
| .120 | 15 | about 18% diameter decrease, followed by 15 sec dwell |
| Scaffold removed from crimp head, inspected, then returned to crimp head. | | |
| .120 | 15 | Scaffold on 3.0 mm balloon catheter, 15 sec dwell within crimp head |
| .041 | 155 | about 66% diameter reduction, followed by 155 sec dwell |

Referring to TABLE 4, for these scaffolds the outer diameter was initially reduced in size by the same amount as with the Control Group, then the scaffold diameter was increased. In the test case the scaffold diameter was expanded to its starting diameter, as indicated in TABLE 4.

TABLE 4

Rejuvenation by Mechanical Strain (radial expansion during crimp/Group 3)

| Crimp head jaw diameter (in) | Dwell (sec) | Comments |
|---|---|---|
| .136 | 15 | Scaffold on 3.0 mm balloon catheter, 15 sec dwell within crimp head |
| .120 | 6 | about 12% diameter reduction, followed by 5 sec dwell |
| .136 | 0.5 | about 13% diameter increase, followed by 0.5 sec dwell |
| .120 | 5 | about 12% diameter reduction, followed by 5 sec dwell |
| Scaffold removed from crimp head, 3.5 mm balloon catheter replaced with 3.0 mm balloon catheter | | |
| .120 | 15 | Scaffold on 3.0 mm balloon catheter, 15 sec dwell within crimp head |
| .041 | 165 | about 66% diameter reduction, followed by 165 sec dwell |

After crimping each of the group Group 1, Group 2 and Group 3 scaffolds were placed within a sheath to limit recoil of the scaffold. The scaffolds (within the sheath) were then sterilized by e-beam radiation sterilization.

Strength & Strain Testing

Figure 2A:
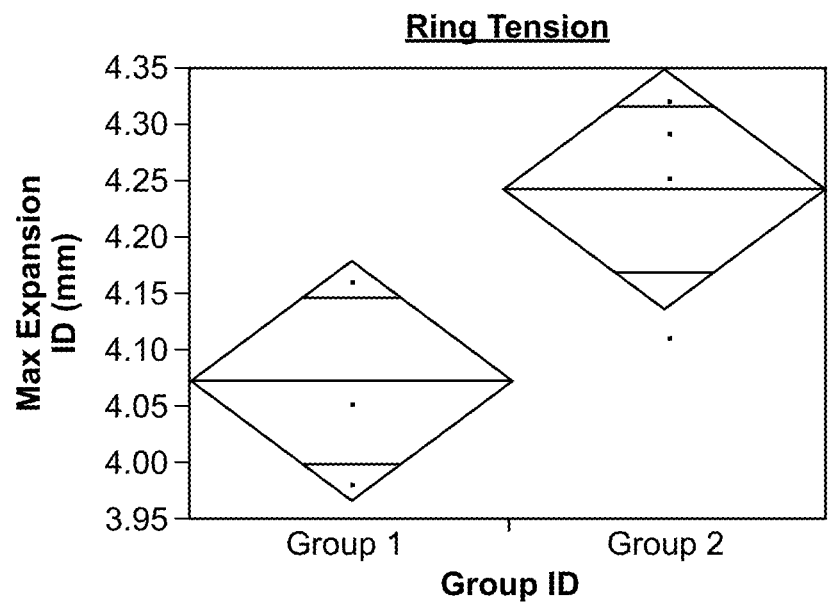
FIG. 2A shows results from a ring tension test for Group 2 Scaffolds having the pattern of FIG. 1.
Figure 2B:
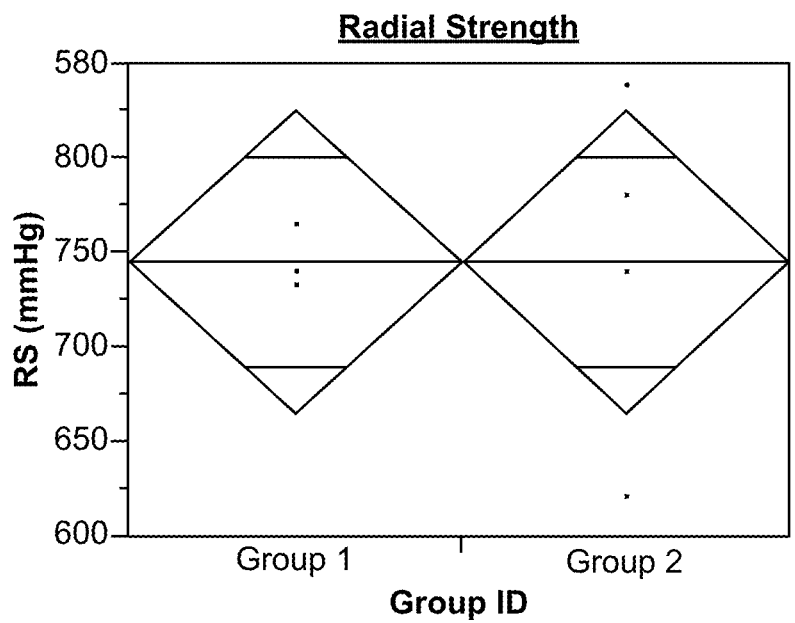
FIG. 2B shows results from a radial strength test for Group 2 Scaffolds having the pattern of FIG. 1.
Figure 3A:
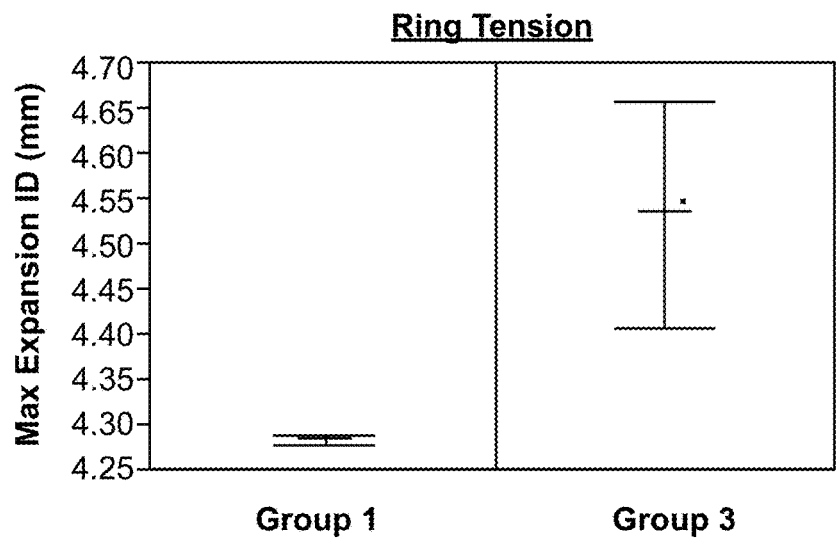
FIG. 3A shows results from a ring tension test for Group 3 Scaffolds having the pattern of FIG. 1.
Figure 3B:
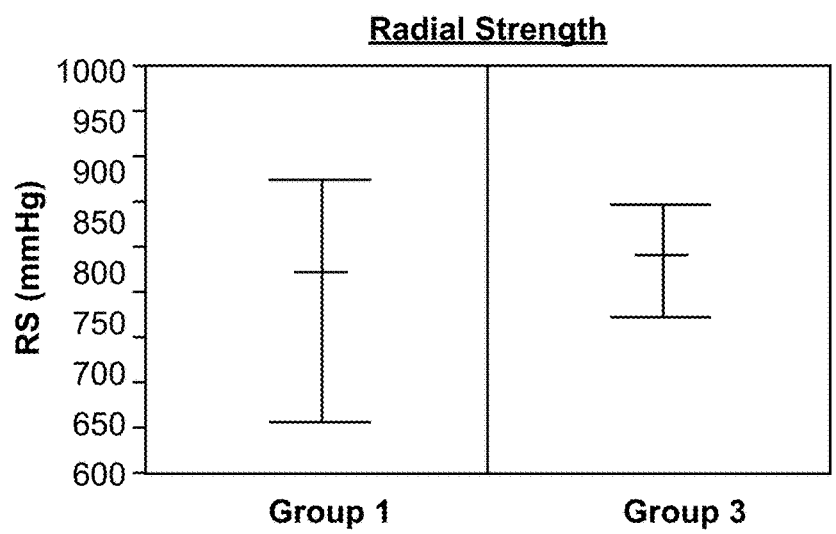
FIG. 3B shows results from a radial strength test for Group 3 Scaffolds having the pattern of FIG. 1.

Ring tension and radial strength tests were conducted for each of the Group 1, Group 2 and Group 3 scaffolds. Several trials were run for each of the two tests. A control group (Group 1) was tested at the same time as Group 2 and Group 3. The results from the tests were used to generate statistics for each group of scaffolds. FIGS. 2A and 3A compare the Max Expansion from the Ring or Ring Tension test for Group 2 and 3 scaffolds to each of their respective control groups. The values for "Max Expansion" are computed using EQ. 1. FIGS. 2B and 3B compare the Radial Strength "RS" Group 2 and 3 scaffolds to each of their respective control groups (a description of the test procedures for the radial strength and Ring tests are provided supra).

Results

Referring to FIGS. 2A and 2B, there is a mean Max Expansion of 4.25 mm for Group 2, as compared to a mean Max Expansion of 4.075 for Group 1. The radial strength between Group 1 and Group 2, however, essentially did not change. The mean Radial Strength measured was about 750 mm Hg for both Group 1 and Group 2. Thus, while the mean radial strength remained essentially unchanged between Group 1 and Group 2, there was a noticeable improvement of about 4.3% in the Max Expansion for Group 2. This indicates an increased toughness of the scaffold material in the radial direction when mechanical rejuvenation by radial expansion is performed shortly before crimping—the maximum expanded diameter (as inferred from the Ring test) increased without a change in the radial strength.

Referring to FIGS. 3A and 3B, there is a mean Max Expansion of 4.53 mm for Group 3, as compared to a mean Max Expansion of 4.28 for Group 1. The radial strength between Group 1 and Group 3, however, essentially did not change. The mean Radial Strength measured was about 800 mm Hg for both Group 1 and Group 3. Thus, while the mean radial strength remained essentially unchanged between Group 1 and Group 3, there was a noticeable improvement of about 5.8% in the Max Expansion for Group 3. This indicates an increased toughness of the scaffold material in the radial direction when mechanical rejuvenation by radial expansion is performed during crimping—the maximum expanded diameter (as inferred from the Ring test) increased without an appreciable change in the radial strength.

Figure 4A:
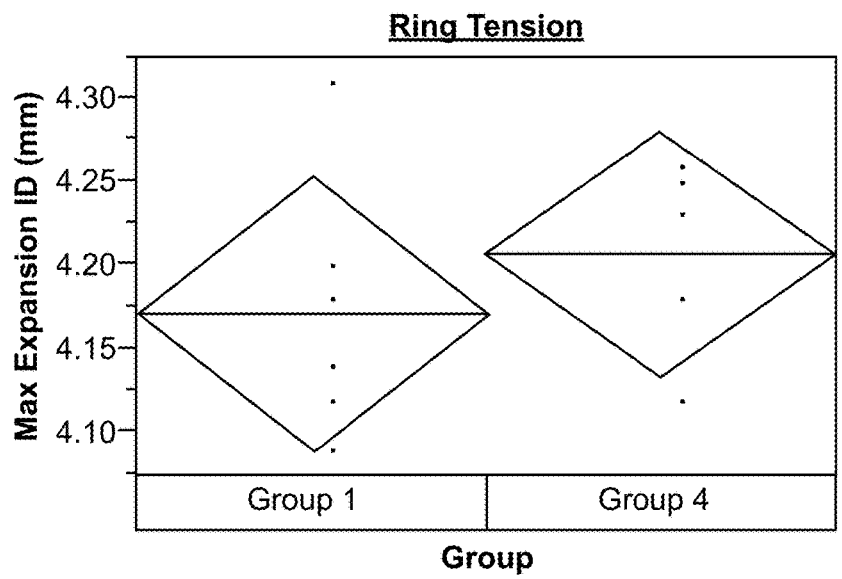
FIG. 4A shows results from a ring tension test for Group 4 Scaffolds having the pattern of FIG. 1.
Figure 4B:
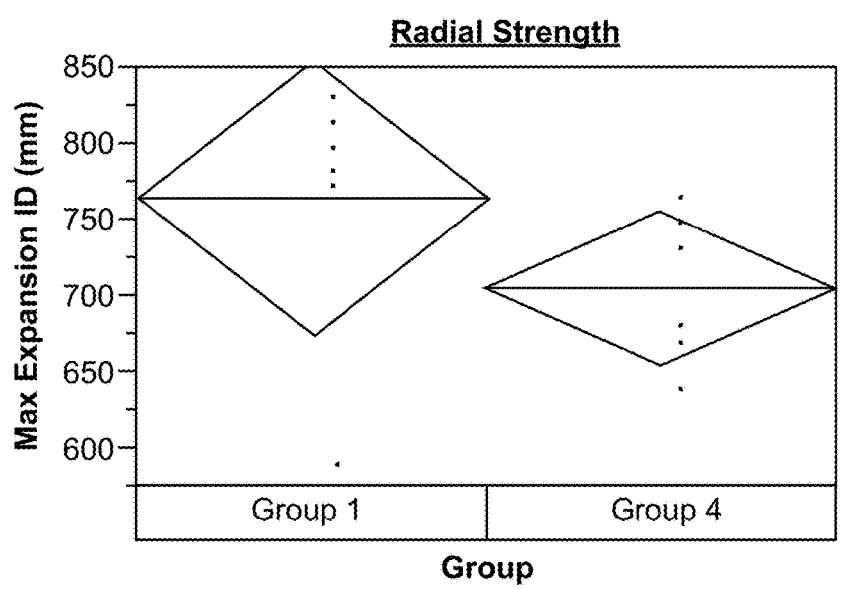
FIG. 4B shows results from a radial strength test for Group 4 Scaffolds having the pattern of FIG. 1.

Referring to FIGS. 4A and 4B there are results shown for the Group 4 scaffolds and their respective control groups. The Group 4 scaffolds were crimped shortly after the forming process (TABLE 1). As such the Group 4 scaffolds represent scaffolds that have reduced or no appreciable ageing effects before crimping. There is a mean Max Expansion of 4.2 mm for Group 4, as compared to a mean Max Expansion of 4.17 for Group 1. As in the case of TEST A, there was an increase in Max Expansion over the control group for Group 4. Unlike TEST A there is a decrease in the radial strength for Group 4 compared with its control group. The mean radial strength drops from about 760 mm Hg to about 700 mm Hg.

TABLE 5

| | Ring Tension Test—percent change in max expansion | Radial Strength Test—percent change in radial strength | Type of process used to avoid crimping of aged scaffold |
|---|---|---|---|
| Group 2 Comparison with control group | +4.3% | unchanged | 7% radial expansion at about 48 Deg. C. shortly before crimping and at least 24 hours after forming process |
| Group 3 Comparison with control group | +5.8% | unchanged | 13% radial expansion at about 48 Deg. C. during crimping and at least 24 hours after forming process |

TABLE 5-continued

| | Ring Tension Test—percent change in max expansion | Radial Strength Test—percent change in radial strength | Type of process used to avoid crimping of aged scaffold |
|---|---|---|---|
| Group 4 comparison with control group | +1% | −8% | Crimping shortly after forming process |

It is believed that the different outcome in radial strength change for Group 4 is attributed to an additional strain-relief aspect of the rejuvenation process applied to the Group 2 and Group 3 scaffolds. Without wishing to be tied to any particular theory, it is suspected that a benefit to the rejuvenation process is a relative polymer center-of-mass (COM) movement driven by strain relief during the radial expansion (or thermal processing discussed infra) and after the initial processing, which initial processing in the above tests was blow molding (the strain baked in during the biaxial expansion/molding drives relative COM motion when the tubing is returned to a temperature above Tg and/or radially expanded without the internal pressurization during blow molding). Group 4 shows enhancement in ring tension due to less total aging of the expanded tube, but it does not have the full strength gain from rejuvenation effects that come from COM polymer chain motion driven by relief of the residual expansion strain from the earlier blow molding process. With respect to the thermal rejuvenation, infra, tube wall thickness increased by about 8% during thermal processing while scaffold strut length and width decreased. The net COM motion conserves volume and relieves the trapped stresses. The relative COM movement of the chains is believed to be a contributor to the rejuvenation effect on at least some of the scaffolds tested.

Thermal Treatment Results

Thermal treatment was tested on different types of scaffolds. The scaffolds differed in pattern, material, strut width, and strut or wall thickness. The scaffolds were formed by methods similar to those disclosed herein which include radially expanded an extruded tube to induce biaxial orientation to increase radial strength of a formed scaffold. The as-fabricated diameter of all scaffolds tested is 3.5 mm.

In each case, after the scaffold is formed from a laser cut tube, the scaffold was thermally processed immediately by baking in air from 10 seconds to 1 week using a Fisher Scientific Isotemp Oven. The temperature was monitored by a glass thermometer. After thermal processing, the scaffold was crimped onto a delivery system within 10 seconds to 1 week. The crimped scaffold profile was about 0.055 in. The delivery system included a 3.0 or 3.5 mm outside diameter balloon. The finished products were e-beam sterilized with a dose of 31 kGy in a 1% O2 environment and then tested.

The testing included deploying the scaffold to selected deployment diameters in saline at 37° C. The radial strength was measured at a nominal deployment diameter of the balloon (3.0 or 3.5 mm). The expansion capability was characterized by computing the Max Expansion (EQ. 1) via the Ring or Ring tension test (in reference to FIGS. 6-13, "Max Expansion ID" or "Ext Before Fracture" all refer to values computed using EQ. 1. In most cases, the number of samples tested per data point was 5.

The materials include PLLA based on a resin with an intrinsic viscosity (IV) of 3.8 dL/g (PLLA IV 3.8); a blend of PLLA (IV 3.8) and poly(L-lactide-co-caprolactone) copolymer, referred to as PLLA/PCL; and a PLLA based on a resin with an IV of 8.25 dL/g (PLLA IV 8.25). The amount and composition of the copolymer in the blend is characterized by the weight percentage of caprolactone as compared to the entire blend composition. Thus, PLLA/PCL 97/3 has 3 wt % caprolactone.

Variations of two types of scaffold pattern designs were used, the first shown in FIG. 5A and the second shown in FIG. 5B. The pattern design shown in FIG. 5A was used with the PLLA IV 3.8 and PLLA/PCL blend scaffolds and the pattern design shown in FIG. 5B was used with the PLLA 8.25 IV scaffolds.

Scaffolds subjected to accelerated ageing were also thermally processed and tested. Extended water exposure was used to mimic physical changes that occur in a scaffold during shelf life. The ageing may correlate to 12 month real-time ageing at ambient temperature. The temperature and soak time of the ageing used varied for material. For PLLA, the ageing conditions are 30° C. for 6 hours. For other materials, conditions are chosen to provide the most stable data. It is expected that the temperature and soak time will lead to "saturated" values that are either representative of aged materials or worst-case behavior.

Example 1

Scaffolds composed of two different types of materials were thermally processed, crimped, and deployed. The scaffold materials were PLLA IV 3.8 and a PLLA/PCL 95-5 blend. The PLLA/PCL 95-5 blend has 95% PLLA and 5% caprolactone polymer by weight.

Oven temperatures were set at 60° C. and 80° C. For each scaffold material, there were four study arms composed of 60° C. for 1 minute and 10 minutes, 80° C. for 1 minute and 10 minutes. These thermal conditions are used to compare with non-thermal processed aged samples of PLLA and PLLA/PCL 95-5 controls.

Figure 6A:
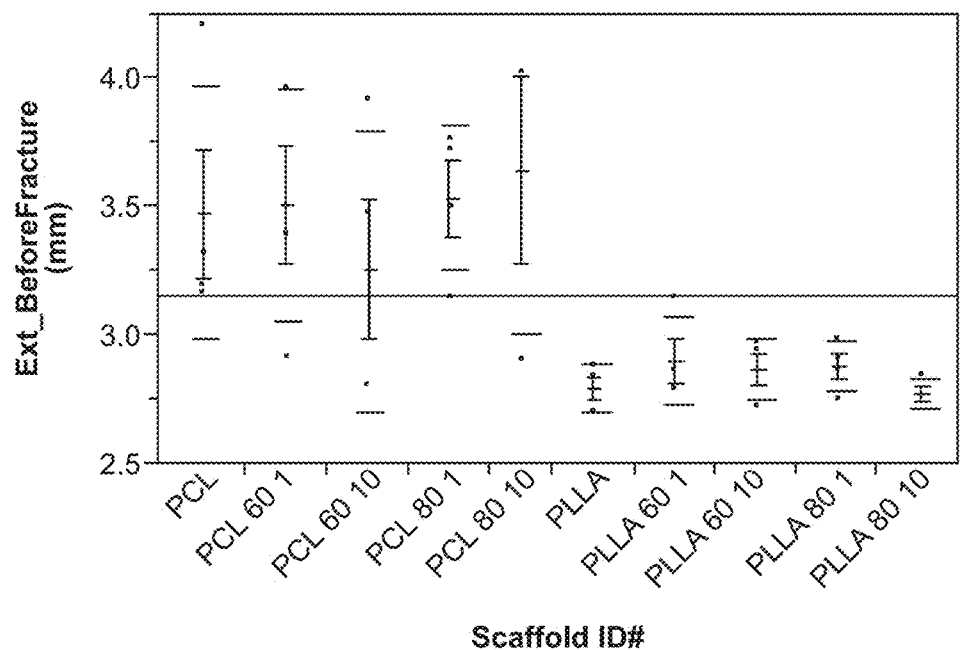
FIG. 6A depicts the effect of thermal treatment on expansion capability for scaffolds of two materials.
Figure 6B:
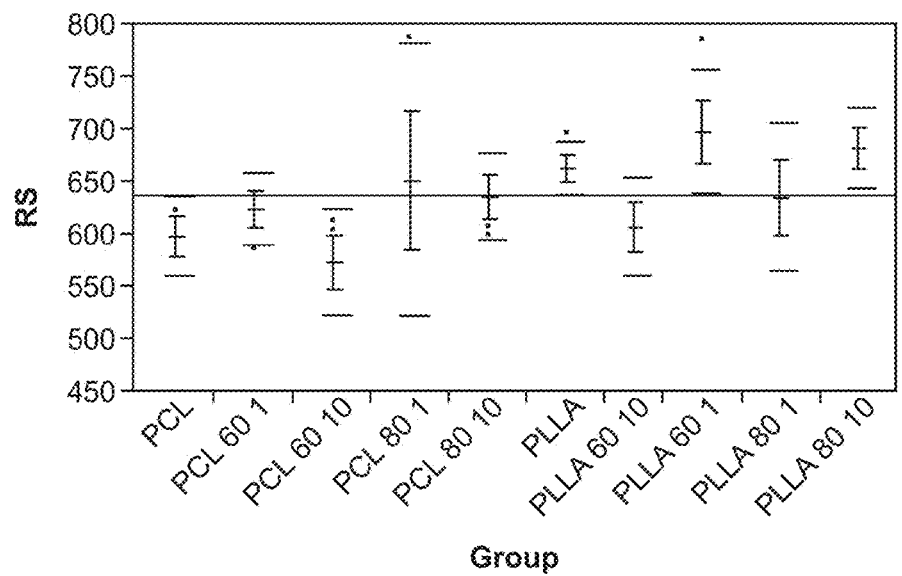
FIG. 6B depicts the effect of thermal treatment on radial strength for scaffolds of two different materials.

FIG. 6A depicts the effect of thermal treatment on expansion capability for scaffolds of two materials. FIG. 6B depicts the effect of thermal treatment on radial strength for scaffolds of two different materials. FIG. 6A shows the Max Expansion for the control and study arms for each scaffold material. FIG. 6B shows the radial strength for the control and study arms for each scaffold material. "PCL" refers to the PLLA/PCL 95-5 blend. Table 5 is a summary of control and study arms of thermal treatment.

TABLE 5

Summary of Control and Study Arms of thermal treatment.

| Arm | Scaffold ID | Material | Time (min) | Temperature (° C.) |
|---|---|---|---|---|
|  | PCL | PLLA/PCL 95-5 | — | — |
| 1 | PCL_60_1 | PLLA/PCL 95-5 | 1 | 60 |
| 2 | PCL_60_10 | PLLA/PCL 95-5 | 10 | 60 |
| 3 | PCL_80_1 | PLLA/PCL 95-5 | 1 | 80 |
| 4 | PCL_80_10 | PLLA/PCL 95-5 | 10 | 80 |
|  | PLLA | PLLA | — | — |
| 1 | PLLA_60_1 | PLLA | 1 | 60 |
| 2 | PLLA_60_10 | PLLA | 10 | 60 |
| 3 | PLLA_80_1 | PLLA | 1 | 80 |
| 4 | PLLA_80_10 | PLLA | 10 | 80 |

For the blend, the Max Expansion is increased by thermal processing at 80° C./10 min and the radial strength is increased at 60° C./1 min, 80° C./1 min, and 80° C./10 min.

Example 2

Scaffolds of two different materials were thermally processed: PLLA/PCL 97/3 blend and PLLA 8.25 IV. The blend has 3% by weight caprolactone. The scaffolds were thermally processed at 80° C. for 10 min. For the PLLA/PCL 97/3 blend, scaffolds with two different strut widths were processed.

Figure 7A:
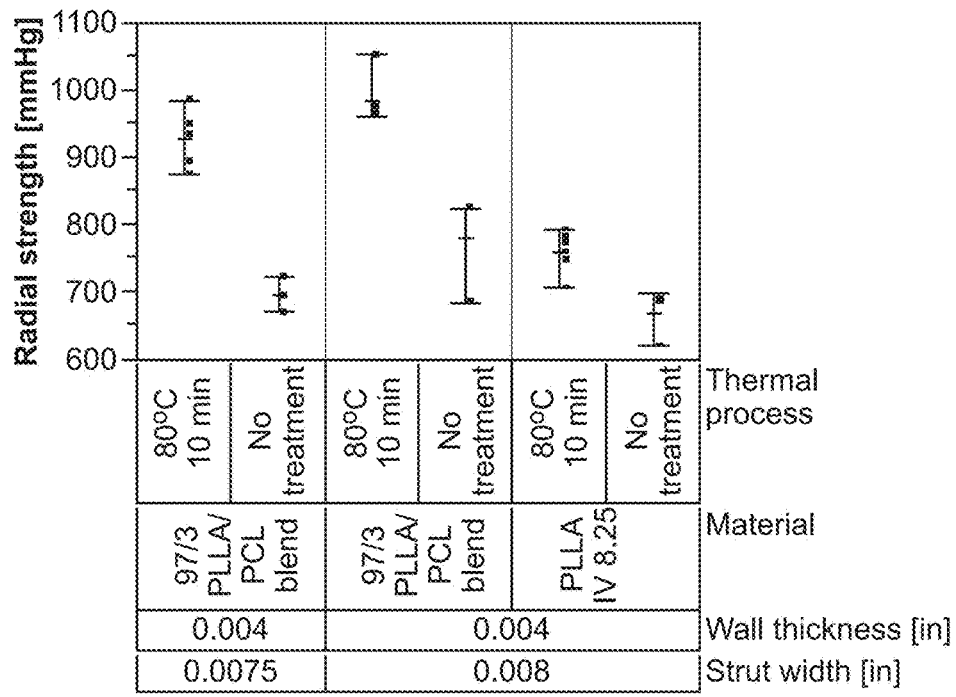
FIG. 7A shows the results for the effect on radial strength of the thermal processing for scaffolds of two different materials.
Figure 7B:
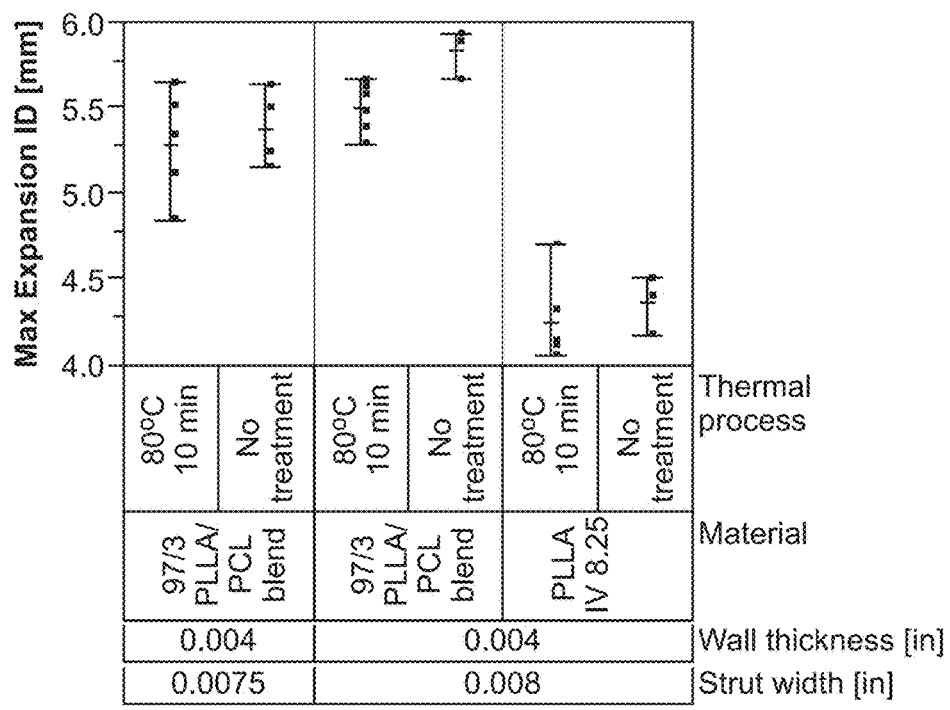
FIG. 7B shows the results for the effect on ring tension of thermal processing for scaffolds of two different materials.

FIG. 7A shows the results for the effect on radial strength of the thermal processing for scaffolds of two different materials. For the blend, radial strength is increased for both scaffolds: about 33% increase for smaller strut width and about 24% increase for the larger strut width. For the PLLA IV 8.25, the radial strength increased about 12% for the scaffold with the larger strut width. The magnitude of effect appears to be dependent on material, but insensitive to design. FIG. 7B shows the results for the effect on Max Expansion of thermal processing for scaffolds of two different materials. The Max Expansion was decreased slightly (less than 6%) for all scaffolds by the thermal treatment.

Example 3

Figure 8A:
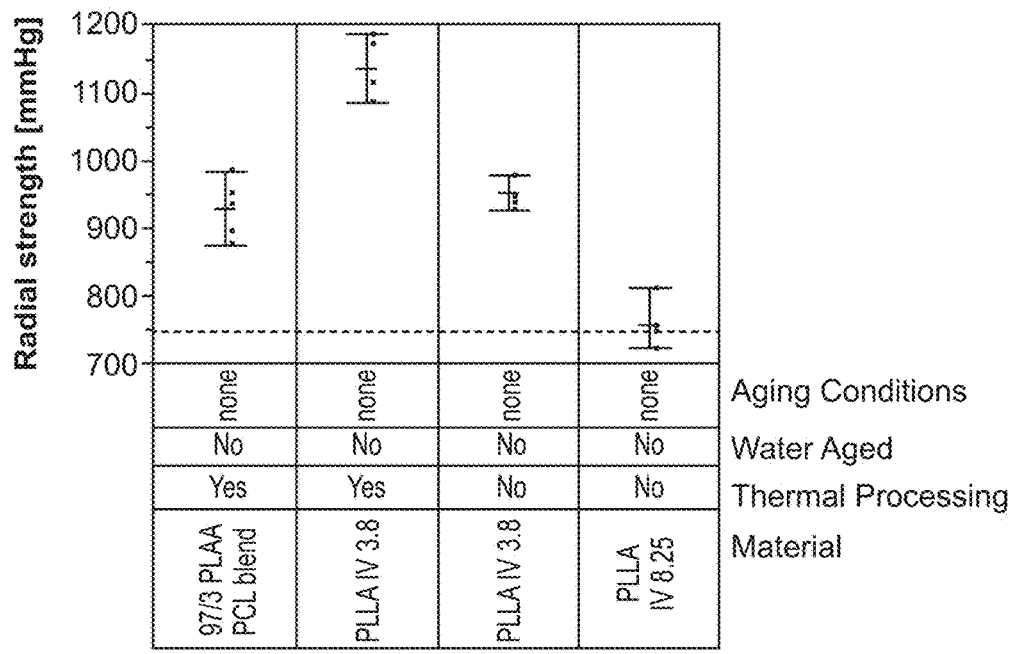
FIG. 8A shows the results for the effect on radial strength of the thermal processing for scaffold of PLLA IV 3.8.
Figure 8B:
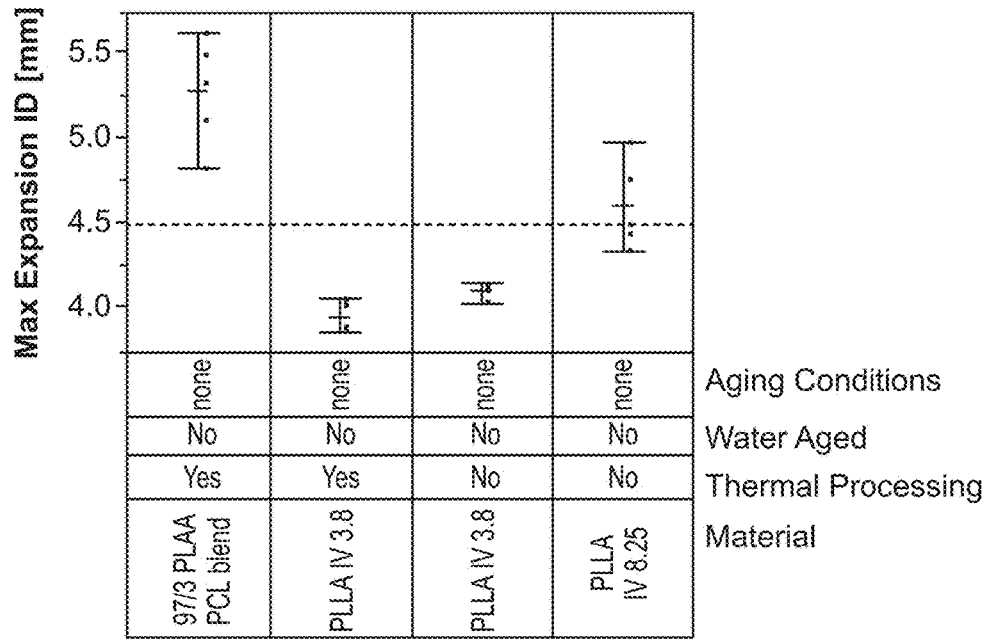
FIG. 8B shows the results for the effect on ring tension of the thermal processing for scaffold of PLLA IV 3.8.

Scaffolds of PLLA 3.8 IV material were thermally processed 80° C. for 10 min. The strut width is 0.0075 in and strut thickness is 0.0062 in. FIG. 8A shows the results for the effect on radial strength of the thermal processing for scaffold of PLLA IV 3.8. The radial strength increased about 20%. FIG. 8B shows the results for the effect on Max Expansion of the thermal processing for scaffold of PLLA IV 3.8. The Max Expansion was decreased slightly, about 4%.

Example 4

Figure 9A:
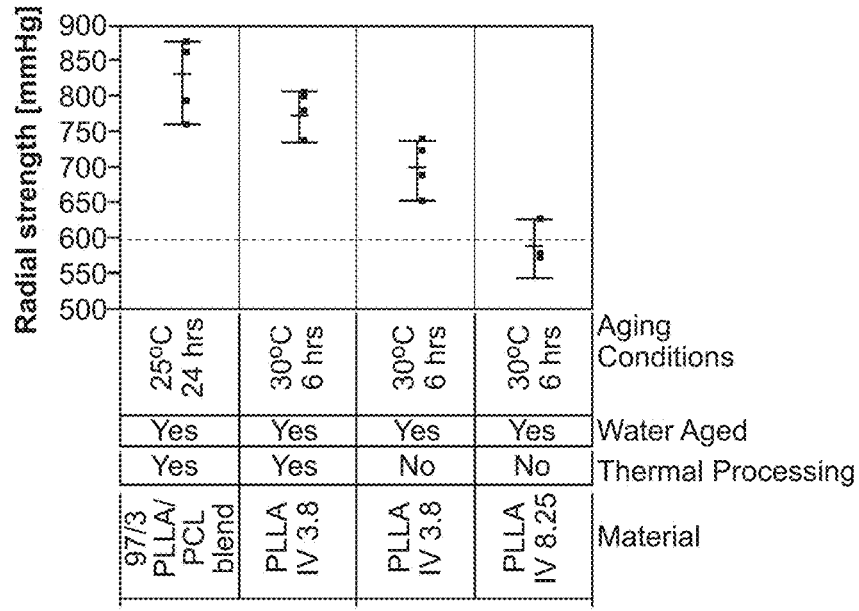
FIG. 9A shows the results for the effect on radial strength of the thermal processing for aged scaffold of PLLA IV 3.8.
Figure 9B:
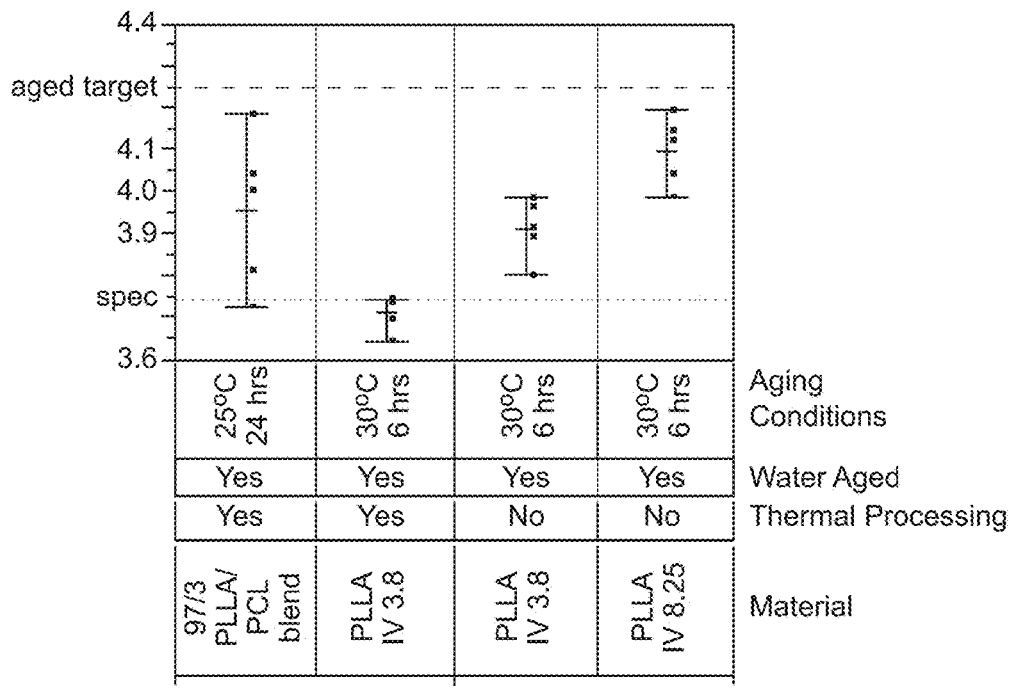
FIG. 9B shows the results for the effect on ring tension of the thermal processing for aged scaffold of PLLA IV 3.8.

Scaffolds of PLLA 3.8 IV material the same as those of example 3 subjected to accelerated ageing were thermally processed 80° C. for 10 min. FIG. 9A shows the results for the effect on radial strength of the thermal processing for aged scaffold of PLLA IV 3.8. The radial strength increased about 10%. FIG. 9B shows the results for the effect on Max Expansion of the thermal processing for aged scaffold of PLLA IV 3.8. The Max Expansion was decreased slightly, about 6%. The increase in radial strength even after ageing is evidence that the thermal processing reduced crimping damage.

Example 5

Figure 10A:
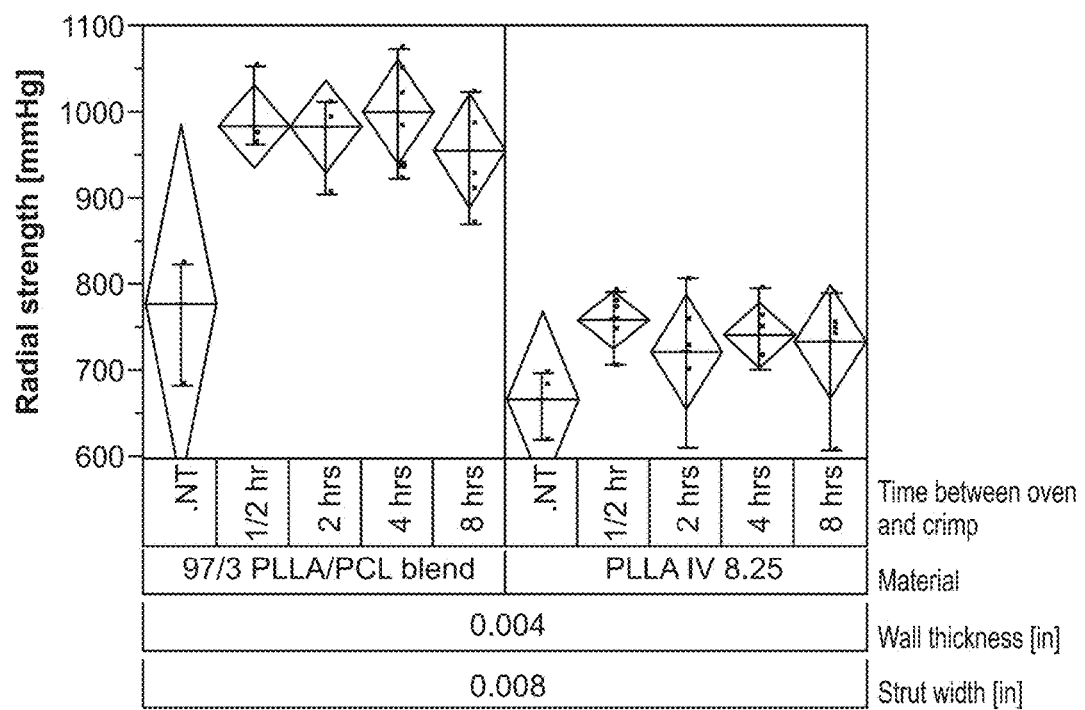
FIG. 10A shows the effect on the time between thermal treatment and crimping on radial strength for scaffolds of two scaffold materials.
Figure 10B:
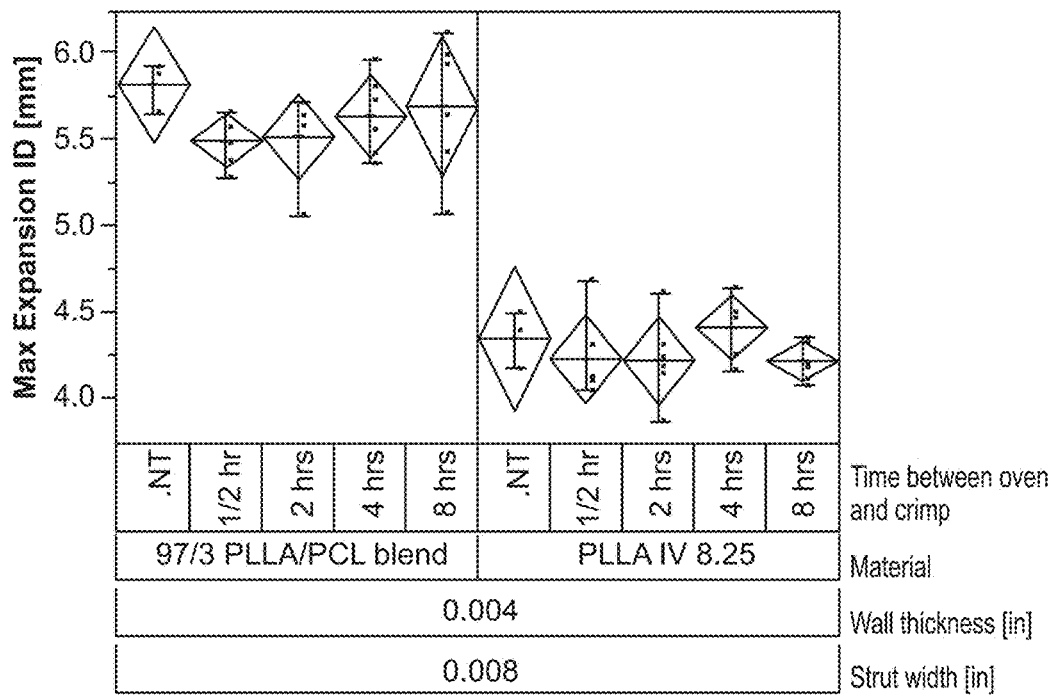
FIG. 10B shows the effect on the time between thermal treatment and crimping on ring tension for scaffolds of two scaffold materials.

The effect on the time between thermal treatment (80° C. for 10 min) and crimping was studied for scaffolds of PLLA/PCL 97/3 blend and PLLA IV 3.8. FIG. 10A shows the effect on the time between thermal treatment and crimping on radial strength for scaffolds of two scaffold materials. FIG. 10A shows a consistent increase in radial strength with thermal processing persisting through an 8 hour window after thermal exposure. FIG. 10B shows the effect on the time between thermal treatment and crimping on Max Expansion for scaffolds of two scaffold materials. The figure shows no noticeable effect on Max Expansion with thermal processing through 8 hour window after temperature exposure.

Example 6

The impact of the L-lactide/caprolactone (LA/CL) ratio in the PLLA/PCL blends on the radial strength and Max Expansion by thermal treatment modification was studied. The blends are summarized in Table 6 below.

TABLE 6

Blend composition of scaffolds.

| LA:CL | PL38 (wt %) | Copolymer (wt %) |
|---|---|---|
| 97:3 | 90 | 10 |
| 98.5:1.5 | 95 | 5 |
| 95.5:4.5 | 85 | 15 |

Scaffolds made of the blends with 3 different LA/CL ratios were thermally processed at 80° C. for 10 min. The test results for the radial strength and Max Expansion of the thermally processed blends were compared to blends with no thermal processing.

Figure 11:
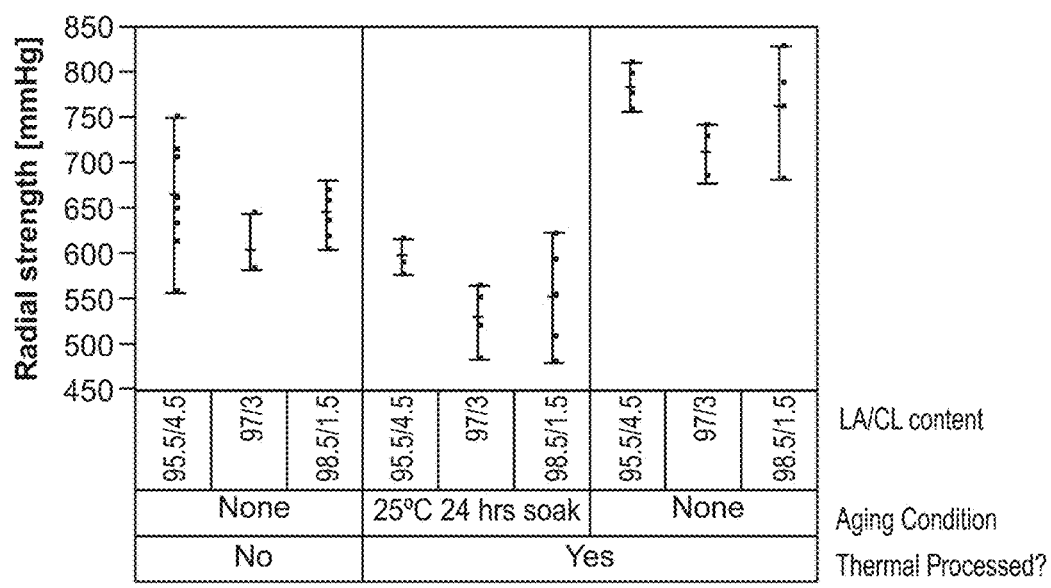
FIG. 11 shows the radial strength of non-thermally processed and thermally processed scaffolds made from PLLA/PCL blends with different L-lactide/caprolactone (LA/CL) ratios.

FIG. 11 shows the radial strength of non-thermally processed and thermally processed scaffolds made from PLLA/PCL blends with different L-lactide/caprolactone (LA/CL) ratios. Decreasing CL content did not appear to increase radial strength for both unaged and aged samples. The thermal processing increased radial strength of blends for each CL content.

Example 7

Figure 12A:
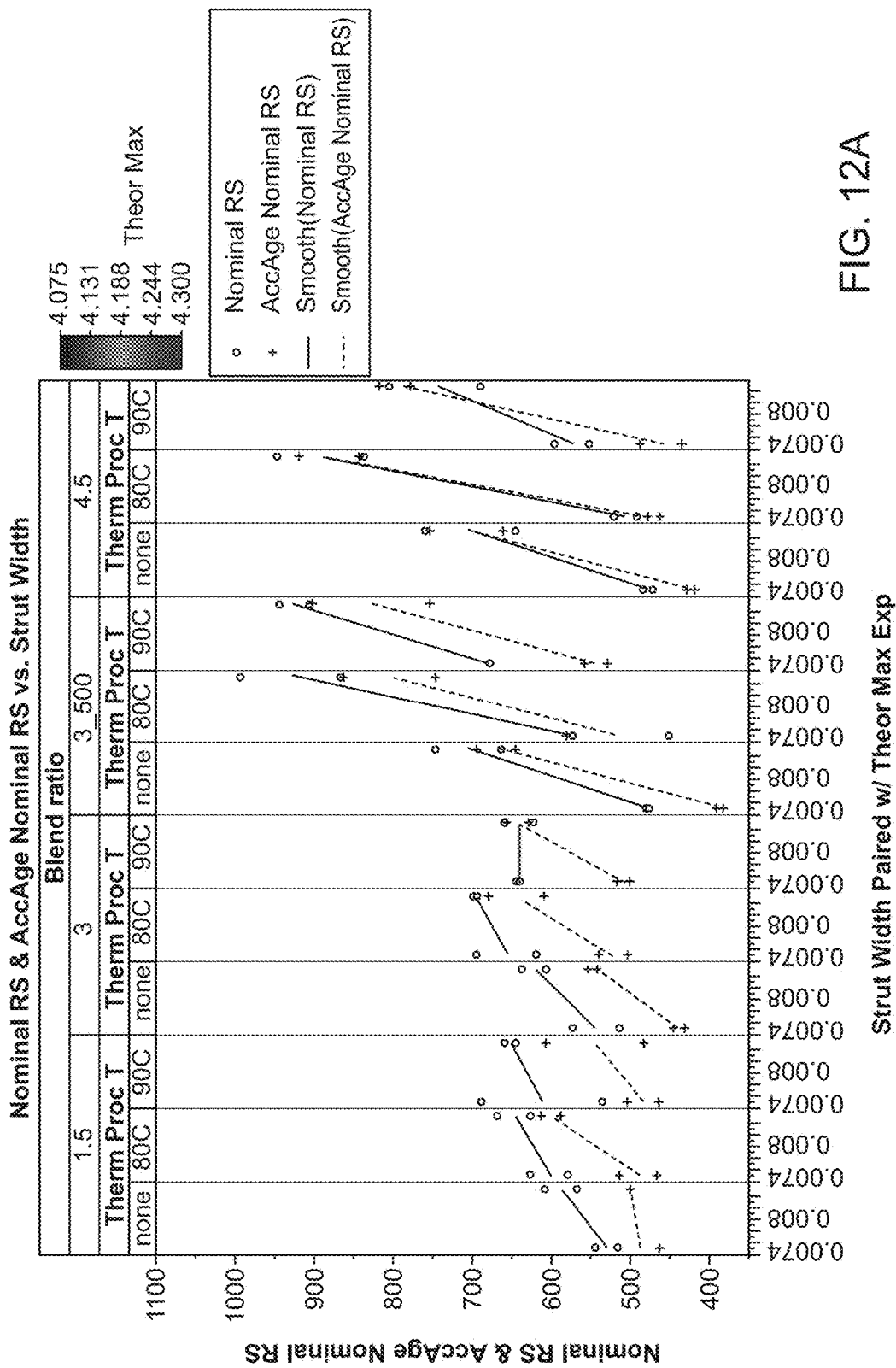
FIG. 12A depicts the radial strength versus strut width of scaffolds for four CL compositions non-thermally processed and thermally processes at 80° C. and 90° C. for 10 min.

FIG. 12A depicts the radial strength versus strut width of scaffolds for four CL compositions non-thermally processed and thermally processes at 80° C. and 90° C. for 10 min. The data shows that the thermal processing at 80° C. in most cases increases the radial strength of the scaffolds, however, the thermal processing at 90° C. in most cases either has no effect or decreases radial strength. This result is consistent with the hypothesis that at 80° C. for 10 min the processing is sufficient to reverse the effects of physical ageing that would otherwise results in increased damage to the scaffold while maintaining the biaxial orientation that increases strength of the scaffold. The thermal processing at the higher temperature of 90° C. and 10 min, however, appears to reduce or eliminates the biaxial orientation, resulting in a weaker scaffold.

Figure 12B:
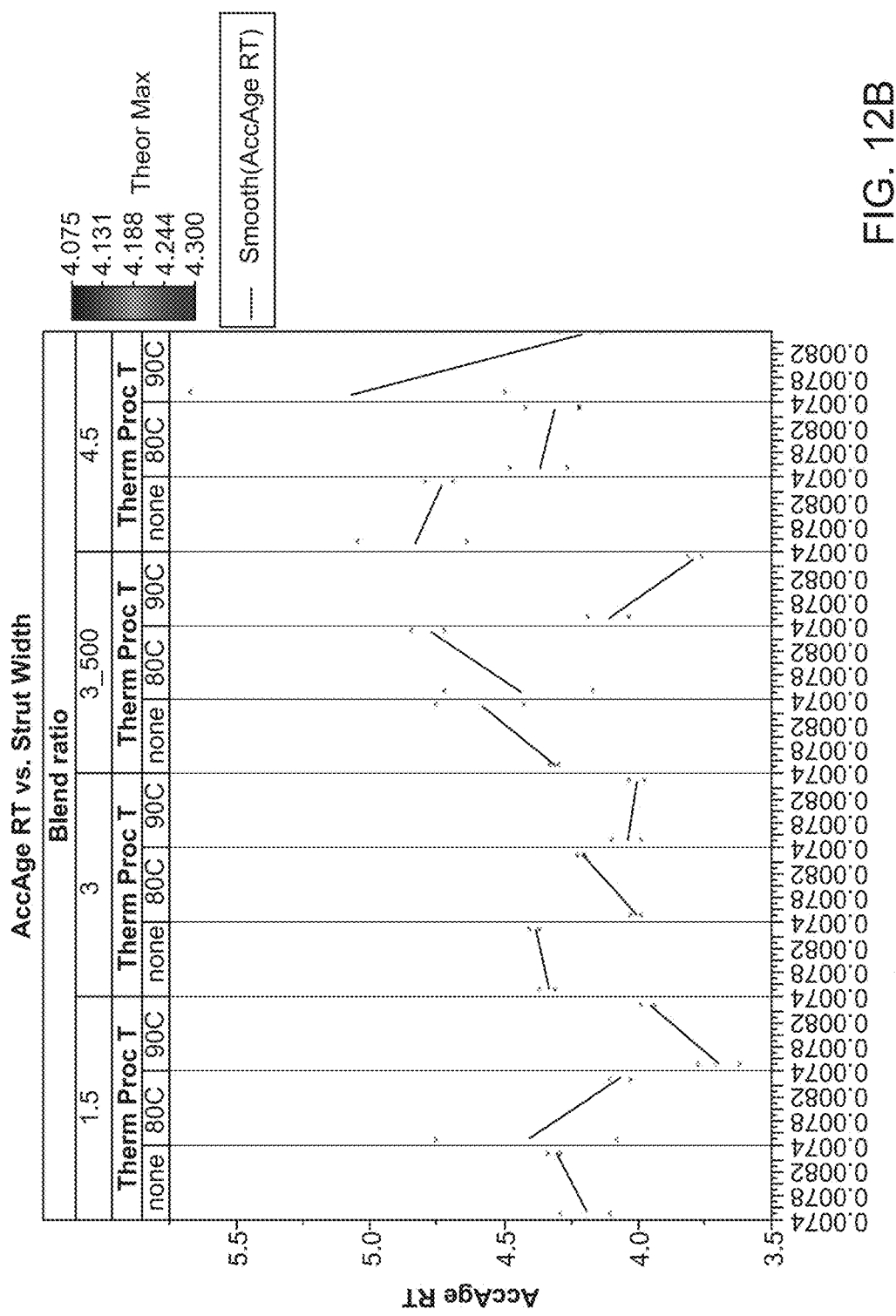
FIG. 12B depicts the ring tension versus strut width of scaffolds for four CL compositions non-thermally processed and thermally processes at 80° C. and 90° C. for 10 min.

FIG. 12B depicts the Max Expansion versus strut width of scaffolds for four CL compositions non-thermally processed and thermally processes at 80° C. and 90° C. for 10 min.

Example 8

Figure 13A:
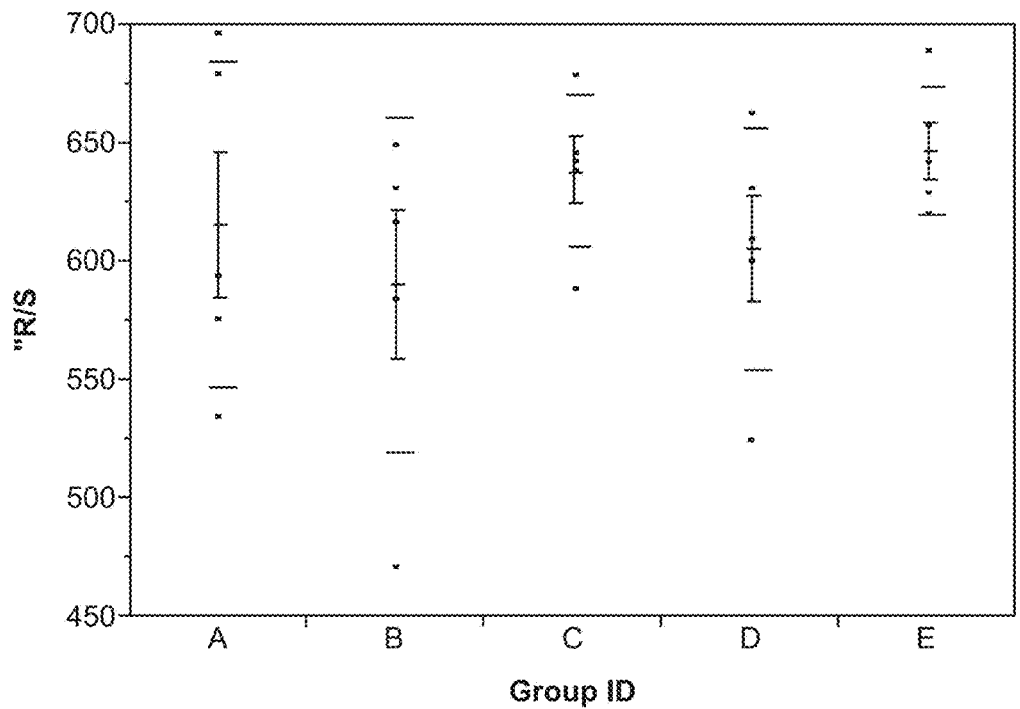
FIG. 13A is a plot depicting the radial strength for five different treatment conditions of PLLA/PCL blend scaffolds (the results for each of five different treatment conditions are distinguishable by the Group identifier A, B, C, D and E).
Figure 13B:
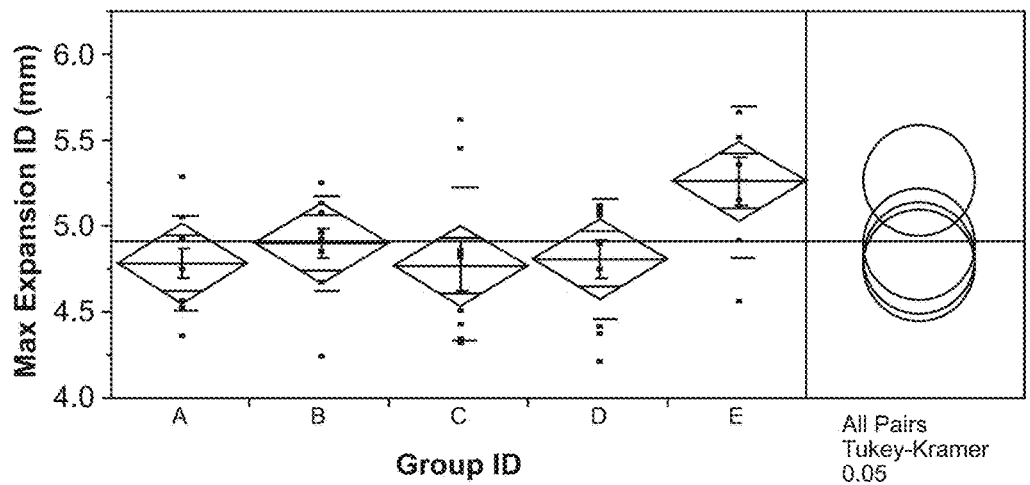
FIG. 13B depicts the maximum expansion inner diameter (ID) for the five treatment conditions A, B, C, D, E for the PLLA/PCL blend scaffolds.
Figure 14A:
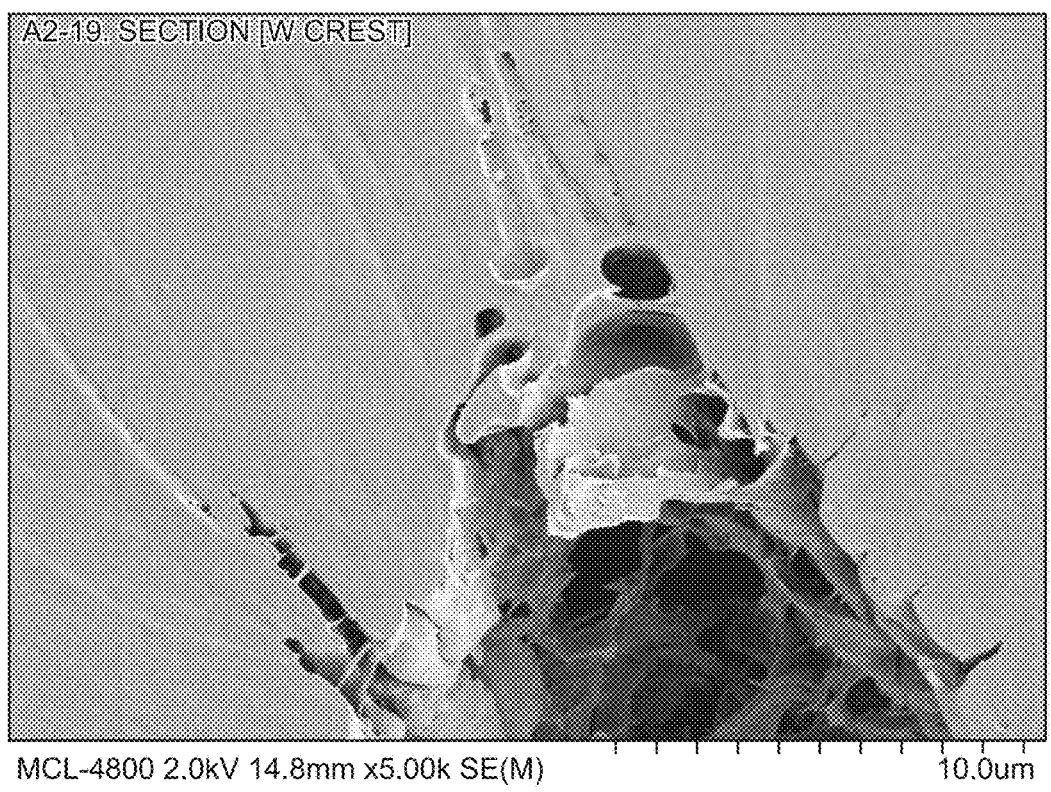
FIG. 14A depicts an SEM image of a crest, crown or bend region of a crimped scaffold with no thermal processing or erasure of ageing before crimping. The scaffold shown was crimped after it had aged.
Figure 14B:
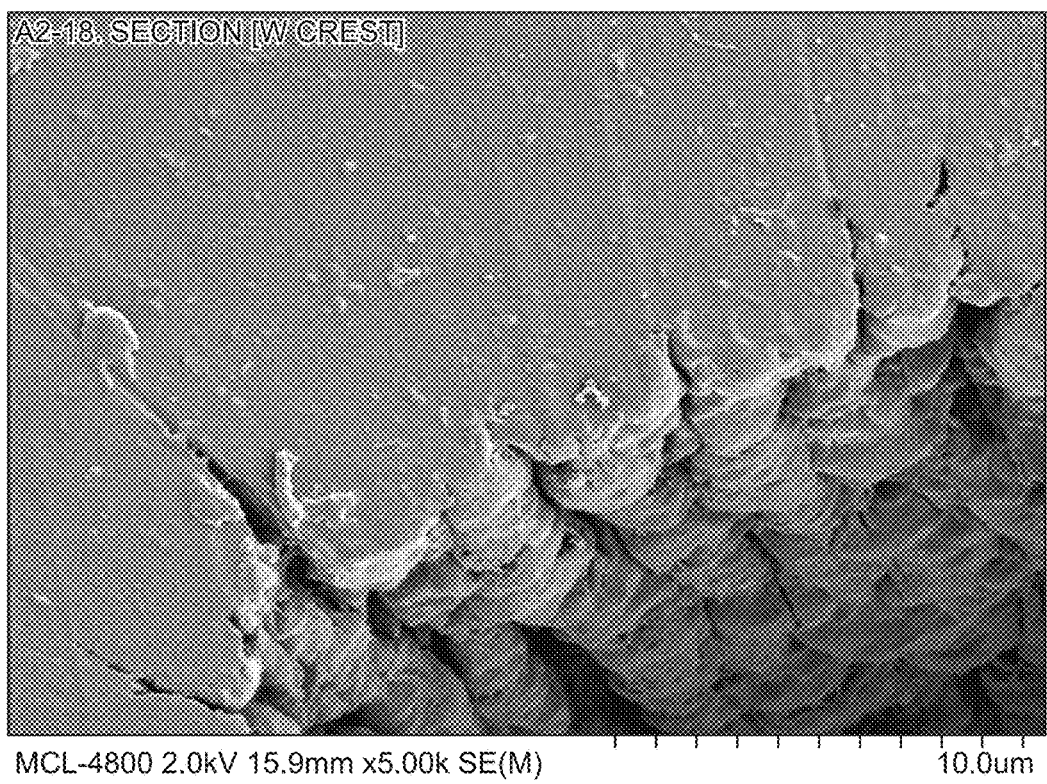
FIG. 14B depicts an SEM image of the crest, crown or bend region of a crimped scaffold that was thermal processing before crimping. The scaffold was processed shortly after erasure of ageing.
Figure 15:
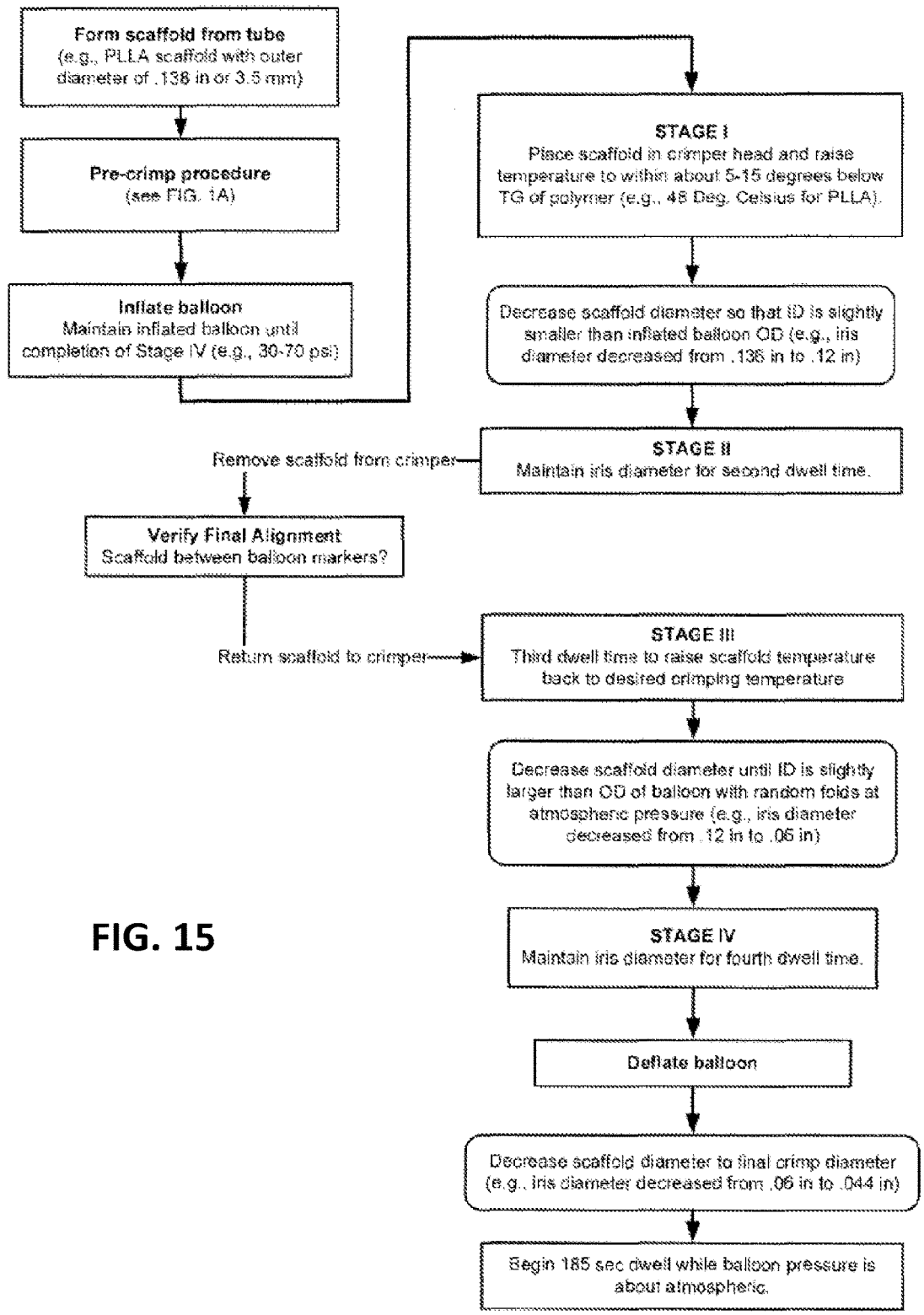
FIG. 15 is an example of a flow process for crimping a polymer scaffold to a balloon.
Figure 16:
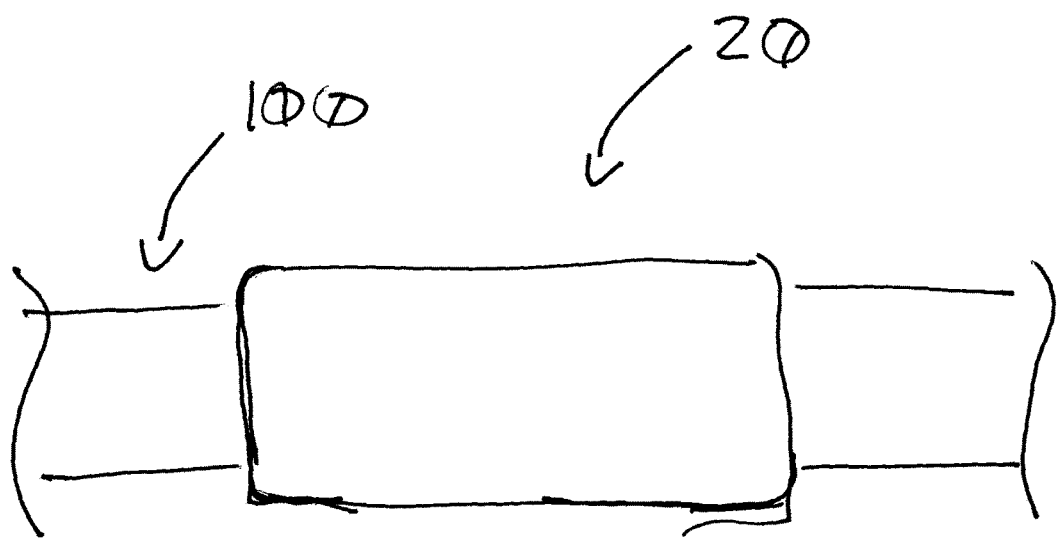
FIG. 16 shows a scaffold 20 on a rod 100.

Scaffolds with a strut width of about 0.008 in and made of PLLA PCL 95.5:4.5 blends were thermally treated at five different conditions: Group A) 80 C, 10 min Group B); 75° C., 5 min; Group C) 75° C., 15 min; Group D) 82 C, 5 min; and Group E) 82 C, 12 min. FIG. 13A is a plot depicting the radial strength measured (mm Hg) for these five treatment conditions. Several trials were run and statistics generated (as shown) for each treatment condition. The conditions of Group E result in the greatest increase in radial strength. The dependence of time and temperature is also demonstrated by the data. Groups B and C are both 75° C., however, Group C has a higher radial strength due to the longer treatment time. A similar trend is shown by comparison of Groups D and E which are both 82° C. FIG. 13B depicts the maximum expansion inner diameter (ID) measured for the five treatment conditions. Several trials were run and statistics generated (as shown) for each treatment condition. Group E, 82 C, 12 min, has the highest expansion capability as well as radial strength. Thus, the data suggests that both the treatment temperature and time may be adjusted to obtain desired radial strength and expansion capability.

Example 9

Scanning electron micrograph (SEM) images were obtained of a crimped scaffold that was not thermally processed before crimping and a crimped scaffold that was thermally processed at 80° C. for 10 min. The scaffold material for both was PLLA/PCL blend 97/3. The SEM images are of a crest or bend region of the scaffold. FIG. 13A depicts an SEM image of the crest or bend region of a crimped scaffold with no thermal processing before crimping. FIG. 13B depicts an SEM image of the crest or bend region of a crimped scaffold that was thermal processing before crimping. The difference in the degree of damage is significant. The non-thermally processed samples show significantly more damage. Specifically, the craze depth is reduced from 10 to 30 microns in the non-thermally processed samples to 0 to 5 microns in the thermally processed units.

Material

The scaffold may be made substantially or completely of a bioabsorbable polymer or polymer combination. "Substantially" in this context means greater than 90 wt %, greater than 95 wt %, or greater than 99 wt %. The scaffold may have a composition of 90 to 95% or 95 to 99% of the polymer combination.

Bioabsorbable polymers and coating may be made from or include poly(L-lactide), polyglycolide, poly(D-lactide), poly(D,L-lactide), polycaprolactone, polytrimethylene carbonate, and poly(4-hydroxybutyrate), and copolymer thereof in any combination and any proportion. Representative copolymers include poly(L-lactide-co-glycolide), poly(DL-lactide-co-glycolide), and poly(L-lactide-co-caprolactone).

The molecular weight of the polymer or polymer combination of polymer scaffold before or after radiation sterilization may be 70 to 100 kDa, 100 to 150 kDa, 150 to 200 kDa, 200 to 300 kDa, 500 to 800 kDa, 800 to 1000 kDa, or greater than 1000 kDa.

A polylactide (PLA) or PLA-based polymer may be made mostly of polylactide. The PLA polymer or PLA polymer of the combination may include poly(L-lactide) (PLLA), poly (D,L-lactide) having a constitutional unit weight-to-weight (wt/wt) ratio of about 96/4, poly(lactide-co-glycolide), poly (L-lactide-co-glycolide), poly(D,L-lactide-co-glycolide), poly(D,L-lactide) made from meso-lactide, and poly(D,L-lactide) made from polymerization of a racemic mixture of L- and D-lactides.

A PLA polymer can include a PLA with a D-lactide content greater than 0 mol % and less than 15 mol %, or more narrowly, 1 to 15 mol %, 1 to 5 mol %, 5 to 10%, or 10 to 15 mol %. The PLA polymer includes poly(D,L-lactide) having a constitutional unit weight-to-weight (wt/wt) ratio of about 93/7, about 94/6, about 95/5, about 96/4, about 97/3, about 98/2, or about 99/1. The term "unit" or "constitutional unit" refers to the composition of a monomer as it appears in a polymer.

The scaffold may include a PLA and PCL (PLA/PCL) random copolymer. The scaffold may be made substantially or completely of the copolymer or a blend of including the PLA/PCL copolymer. The copolymer may include poly(L-lactide-co-caprolactone), poly(D,L-lactide-co-caprolactone), poly(L-lactide-co-glycolide-co-caprolactone), and poly(DL-lactide-co-glycolide-co-caprolactone). The copolymer with D,L-lactide may be made from a racemic mixture of L- and D-lactide or may include 1 to 15% of D constitutional units. The scaffold may be made substantially or completely of the copolymer. In some embodiments, the scaffold may include no PLA homopolymer, PCL homopolymer, or less than 20%, 10%, 5%, or less than 1% of either homopolymer.

The copolymer may include 1 to 5% (wt % or mol %) of caprolactone units, or more narrowly, 1 to 2%, 2 to 5%, 3 to 5%, or about 3%. The tube may be made from a copolymer resin with an IV greater than 5 dL/g, greater than 7 dL/g greater than 8 dl/g, 4 to 8 dL/g, 4 to 6 dL/g, 6 to 8 dL/g, or 5 to 7 dL/g.

The crystallinity of the copolymer or tube made of the copolymer and following blow molding or die drawing may be 20 to 50%, 20 to 25%, 25 to 30%, 30 to 35%, 35 to 40%, 40 to 45%, and 45 to 50%.

A scaffold material may be characterized in terms of the resin from which it is formed. A polymer resin is the raw material used for the melt processing for forming the polymeric tube. In order to provide the high molecular weight of the finished sterilized product, the resin has a much higher molecular weight than the finished product. The molecular weight of the polymer decreases during processing, mostly during extrusion and radiation (e.g., sterilization). The molecular weight of the resin may be expressed in terms of the intrinsic viscosity (IV) in dL/g. The IV of a polymer resin may be higher than 5 dL/g, greater than 7 dL/g greater than 8 dl/g, 3 to 8.5 dL/g, 5 to 8.5 dL/g, 3 to 6 dL/g, 6 to 8 dL/g, or 5 to 7 dL/g. cterize in terms of IV. Exemplary resins are 3.8 and 8.25 dL/g.

Various polymer combinations are contemplated including a PLA polymer and PCL: Among the combinations: (1) PLA and PCL random copolymer; (2) block copolymer including PLA polymer blocks and PCL polymer blocks; (3) a blend of a PLA polymer with PCL homopolymer; (4) blend of a PLA homopolymer blended and a PLA and PCL copolymer; and (5) a blend of a PCL homopolymer and a PLA and PCL copolymer.

The scaffold may be a polymer combination that is a blend of polylactide (PLA) based polymer and a PLA and polycaprolactone (PCL) random copolymer (PLA/PCL blend). The PLA based polymer may be greater than 80%, 90%, 95%, 97%, or 98% of the blend. The CL composition of the copolymer may be 10-40%, or more narrowly 15 to 25%, or 20%. The PLA/PCL blend may have between about 1% to 5% by weight PCL.

The amount and composition of the copolymer in the PLA/PCL blend may be characterized by the weight percentage of caprolactone as compared to the entire blend composition. The caprolactone composition of the blend may be The scaffold number average molecular weight (Mn) of the PLA/PCL blend may be 70 to 100 kDa, 100 to 200 kDa, 200 to 500 kDa, or 300 to 500 kDa. The blend may be made from a PLA-based polymer resin in any of the ranges above, such as 3.8 dL/g.

Embodiments of a tube include tubes that are a block copolymer including PLA polymer blocks and PCL polymer blocks. The tube may be made substantially or completely of the block copolymer. The block copolymer may be a linear block copolymer or branched block copolymer such as a star block copolymer.

The tube may include no PLA homopolymer, PCL homopolymer, or less than 20%, 10%, 5%, or less than 1% of either homopolymer. The PLA blocks may include PLLA, poly(L-lactide-co-glycolide), poly(D,L-lactide-co-glycolide), and poly(D,L-lactide). Blocks with D,L-lactide may be made from a racemic mixture of L- and D-lactide or may include 1 to 15% of D constitutional units. The tube may be made substantially or completely of the block copolymer.

The block copolymer may include 1 to 5% (wt % or mol %) of polycaprolactone blocks, or more narrowly, 1 to 2%, 2 to 5%, 3 to 5%, or about 3%. The tube may be made from a copolymer resin with an IV greater than 5 dL/g, greater than 7 dL/g greater than 8 dl/g, 4 to 8 dL/g, 4 to 6 dL/g, 6 to 8 dL/g, or 5 to 7 dL/g.

The crystallinity of the copolymer or tube made of the copolymer after blow molding or die drawing may be 20 to 50%, 20 to 25%, 25 to 30%, 30 to 35%, 35 to 40%, 40 to 45%, and 45 to 50%.

Embodiments of a tube include tubes that are a blend of a PLA polymer with a PCL homopolymer. The tube may be made substantially or completely of the blend. The PLA polymer may include PLLA, poly(L-lactide-co-glycolide), poly(D,L-lactide-co-glycolide), and poly(D,L-lactide). PLA polymers with D,L-lactide may be made from a racemic mixture of L- and D-lactide or may include 1 to 15% of D constitutional units. The tube may be made substantially or completely of the block copolymer.

The blend may include 1 to 5% (wt % or mol %) of PCL homopolymer, or more narrowly, 1 to 2%, 2 to 5%, 3 to 5%, or about 3%. The tube may be made from a PLA resin or resin blend with an IV greater than 5 dL/g, greater than 7 dL/g greater than 8 dl/g, 4 to 8 dL/g, 4 to 6 dL/g, 6 to 8 dL/g, or 5 to 7 dL/g.

The crystallinity of the blend or tube made of the blend after blow molding or die drawing may be 20 to 50%, 20 to 25%, 25 to 30%, 30 to 35%, 35 to 40%, 40 to 45%, and 45 to 50%.

Embodiments of a tube include tubes that are a blend of a PLA polymer with a PLA and PCL copolymer. The tube may be made substantially or completely of the blend. The PLA polymer may include PLLA, poly(L-lactide-co-glycolide), poly(D,L-lactide-co-glycolide), and poly(D,L-lactide). PLA polymers with D,L-lactide may be made from a racemic mixture of L- and D-lactide or may include 1 to 15% of D constitutional units.

The copolymer may be PLA and PCL random copolymer or a block copolymer of PLA polymer blocks and PCL homopolymer blocks. The random copolymer may include any from the list of PLA and PCL random copolymers provided above. The block copolymer may be linear block copolymer or branched block copolymer such as a star block copolymer. The tube may be made substantially or completely of the blend.

The tube may be made from a PLA resin or the resin blend with an IV greater than 5 dL/g, greater than 7 dL/g greater than 8 dl/g, 4 to 8 dL/g, 4 to 6 dL/g, 6 to 8 dL/g, or 5 to 7 dL/g.

The caprolactone units in either the random or block copolymer may be 1 to 5% (wt % or mol %) of the blend, or more narrowly, 1 to 2%, 2 to 5%, 3 to 5%, or about 3% of the blend.

The crystallinity of the blend or tube made of the blend after blow molding or die drawing may be 20 to 50%, 20 to 25%, 25 to 30%, 30 to 35%, 35 to 40%, 40 to 45%, and 45 to 50%.

Embodiments of a tube include tubes that are a blend of a PCL homopolymer with a PLA and PCL copolymer. The tube may be made substantially or completely of the blend. The copolymer may be PLA and PCL random copolymer or a block copolymer of PLA polymer blocks and PCL homopolymer blocks. The random copolymer may include any from the list of PLA and PCL random copolymers provided above. The block copolymer may include any from the list of PLA and PCL block copolymers provided above. The block copolymer may be linear block copolymer or branched block copolymer such as a star block copolymer. The tube may be made substantially or completely of the blend.

The tube may be made from a copolymer resin or the resin blend with an IV greater than 5 dL/g, greater than 7 dL/g, greater than 8 dl/g, 4 to 8 dL/g, 4 to 6 dL/g, 6 to 8 dL/g, or 5 to 7 dL/g.

The total caprolactone units in both the copolymer and the PCL may be 1 to 5% (wt % or mol %) of the blend, or more narrowly, 1 to 2%, 2 to 5%, 3 to 5%, or about 3% of the blend. The PCL homopolymer may be 0.5% to 4% of the blend. The caprolactone content of the copolymer may be 05% to 4%.

The crystallinity of the blend or tube made of the blend after biaxial processing may be 20 to 50%, 20 to 25%, 25 to 30%, 30 to 35%, 35 to 40%, 40 to 45%, and 45 to 50%.

Therapeutic Agents

The device body may include or may be coated with one or more therapeutic agents, including an antiproliferative, anti-inflammatory or immune modulating, anti-migratory, anti-thrombotic or other pro-healing agent or a combination thereof. The anti-proliferative agent can be a natural proteineous agent such as a cytotoxin or a synthetic molecule or other substances such as actinomycin D, or derivatives and analogs thereof (manufactured by Sigma-Aldrich 1001 West Saint Paul Avenue, Milwaukee, Wis. 53233; or COSMEGEN available from Merck) (synonyms of actinomycin D include dactinomycin, actinomycin IV, actinomycin I1, actinomycin X1, and actinomycin C1), all taxoids such as taxols, docetaxel, and paclitaxel, paclitaxel derivatives, all olimus drugs such as macrolide antibiotics, rapamycin, everolimus, novolimus, myolimus, deforolimus, umirolimus, biolimus, merilimus, temsirolimus structural derivatives and functional analogues of rapamycin, structural derivatives and functional analogues of everolimus, FKBP-12 mediated mTOR inhibitors, biolimus, perfenidone, prodrugs thereof, co-drugs thereof, and combinations thereof. Representative rapamycin derivatives include 40-O-(3-hydroxy)propyl-rapamycin, 40-O-[2-(2-hydroxy)ethoxy]ethyl-rapamycin, or 40-O-tetrazole-rapamycin, 40-epi-(N1-tetrazolyl)-rapamycin (ABT-578 manufactured by Abbott Laboratories, Abbott Park, Ill.), prodrugs thereof, co-drugs thereof, and combinations thereof.

The anti-inflammatory agent can be a steroidal anti-inflammatory agent, a nonsteroidal anti-inflammatory agent, or a combination thereof. In some embodiments, anti-inflammatory drugs include, but are not limited to, novolimus, myolimus, alclofenac, alclometasone dipropionate, algestone acetonide, alpha amylase, amcinafal, amcinafide, amfenac sodium, am iprilose hydrochloride, anakinra, anirolac, anitrazafen, apazone, balsalazide disodium, bendazac, benoxaprofen, benzydamine hydrochloride, bromelains, broperamole, budesonide, carprofen, cicloprofen, cintazone, cliprofen, clobetasol propionate, clobetasone butyrate, clopirac, cloticasone propionate, cormethasone acetate, cortodoxone, deflazacort, desonide, desoximetasone, dexamethasone dipropionate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lomoxicam, loteprednol etabonate, meclofenamate sodium, meclofenamic acid, meclorisone dibutyrate, mefenamic acid, mesalamine, meseclazone, methylprednisolone suleptanate, momiflumate, nabumetone, naproxen, naproxen sodium, naproxol, nimazone, olsalazine sodium, orgotein, orpanoxin, oxaprozin, oxyphenbutazone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, sudoxicam, sulindac, suprofen, talmetacin, talniflumate, talosalate, tebufelone, tenidap, tenidap sodium, tenoxicam, tesicam, tesimide, tetrydamine, tiopinac, tixocortol pivalate, tolmetin, tolmetin sodium, triclonide, triflumidate, zidometacin, zomepirac sodium, aspirin (acetylsalicylic acid), salicylic acid, corticosteroids, glucocorticoids, tacrolimus, pimecorlimus, prodrugs thereof, co-drugs thereof, and combinations thereof.

These agents can also have anti-proliferative and/or anti-inflammatory properties or can have other properties such as antineoplastic, antiplatelet, anti-coagulant, anti-fibrin, anti-thrombonic, antimitotic, antibiotic, antiallergic, antioxidant as well as cystostatic agents. Examples of suitable therapeutic and prophylactic agents include synthetic inorganic and organic compounds, proteins and peptides, polysaccharides and other sugars, lipids, and DNA and RNA nucleic acid sequences having therapeutic, prophylactic or diagnostic activities. Nucleic acid sequences include genes, antisense molecules which bind to complementary DNA to inhibit transcription, and ribozymes. Some other examples of other bioactive agents include antibodies, receptor ligands, enzymes, adhesion peptides, blood clotting factors, inhibitors or clot dissolving agents such as streptokinase and tissue plasminogen activator, antigens for immunization, hormones and growth factors, oligonucleotides such as antisense oligonucleotides and ribozymes and retroviral vectors for use in gene therapy. Examples of antineoplastics and/or antimitotics include methotrexate, azathioprine, vincristine, vinblastine, fluorouracil, doxorubicin hydrochloride (e.g. Adriamycin® from Pharmacia & Upjohn, Peapack N.J.), and mitomycin (e.g. Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, thrombin inhibitors such as Angiomax a (Biogen, Inc., Cambridge, Mass.), calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), nitric oxide or nitric oxide donors, super oxide dismutases, super oxide dismutase mimetic, 4-amino-2,2,6,6-tetramethylpiperidine-1-oxyl (4-amino-TEMPO), estradiol, anticancer agents, dietary supplements such as various vitamins, and a combination thereof. Examples of such cytostatic substance include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.). An example of an antiallergic agent is permirolast potassium. Other therapeutic substances or agents which may be appropriate include alpha-interferon, and genetically engineered epithelial cells. The foregoing substances are listed by way of example and are not meant to be limiting. Other active agents which are currently available or that may be developed in the future are equally applicable.

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in claims should not be construed to limit the invention to the specific embodiments disclosed in the specification.

In the following set of claims there are multiple dependent claims designed in shorthand by a hyphen. For example, "Claim 1a-1e" means "Claim 1a, Claim 1b, Claim 1c, Claim 1d, or Claim 1e."

According to other aspects of invention there is the following concepts 1, 1a-1o, 2, 3, 3a-3c, 4, 4a-4d, 5, 5a-5f, 6, 6a-6dd, 7, 7a-7d, 8, 8a-8d, 9, 9a-9e, 10, 10a-10d, 11, 11a-11e, 12, and 12a-12f:

1. A method for making a medical device, comprising:
providing a tube made from a material comprising a polymer composition having a glass transition temperature (Tg), the tube being formed by, or modified by a forming process, wherein the forming process includes the step of at least one of raising the temperature of the tube to about, or greater than about Tg or radially straining the material beyond a yield strain for the material;
making a scaffold from the tube formed by, or modified by the forming process; and
crimping the scaffold to a balloon shortly after the tube is formed by, or modified by the forming process.

1a. The method of Concept(s) 1, further comprising:
reducing the temperature of the tube and/or scaffold to about 50, 60, 80, 100, 50 to 150, or about 50 to 80 degrees below Tg; and
crimping the thawed scaffold to a balloon.

1b. The method of Concept(s) 1 or 1a, further comprising:
rejuvenating the scaffold before crimping.

1c. The method of Concept(s) 1b, wherein the rejuvenating the scaffold includes at least one of raising the scaffold temperature to above about Tg or radially expanding the scaffold to induce a strain in the material beyond the yield strain of the material.

1d. The method of Concept(s) 1c, wherein the rejuvenating the scaffold includes radially expanding the scaffold diameter by about 5 to 7%, about 5 to 10%, or about 10 to 15% relative to a pre-crimp scaffold diameter or a partially crimped scaffold diameter.

1e. The method of Concept(s) 1d, wherein the scaffold diameter is reduced in diameter, followed by the radially expanding the scaffold diameter and the scaffold diameter.

1f. The method of Concept(s) 1b, wherein the rejuvenation takes place within a crimp head of a crimping mechanism.

1g. The method of Concept(s) 1d-1f, wherein the crimping step comprises rejuvenating the scaffold, wherein the scaffold diameter is increased after being partially crimped.

1h. The method of Concept(s) 1b, wherein the rejuvenation includes inducing a strain beyond a yield, wherein a crest of a scaffold ring has a highest yield strain of about 5 to 20% beyond the strain where yield occurs for the scaffold crest when the scaffold is radially expanded.

1i. The method of Concept(s) 1c-1g, wherein the scaffold temperature is about Tg, or about 30, 20, 15 or 5 Deg. C. less than Tg when the scaffold diameter is increased.

1j. The method of Concept(s) 1-1i, wherein the crimping includes one or more of, or any combination of:
apply a radially outward pressure to a scaffold resulting in an about 5 to 7%, 5 to 10% or about 10 to 15% increase in the scaffold diameter;
during rejuvenation the scaffold has a temperature below Tg for the scaffold material, or between about Tg and 5, 10, 15, 20 or 25 degrees below Tg for the scaffold material;
after radial expansion the scaffold diameter is held at the expanded diameter for an about 1 to 5 second dwell, or 10 to 30 second dwell before a radial constraint is withdrawn;
the rejuvenation is done within a crimp head or shortly before placing the scaffold within a crimp head;
rejuvenation occurs prior to any diameter reduction within the crimp head, or after a first or second diameter reduction within a crimp head; and/or rejuvenation is performed using a balloon catheter that is the same as the balloon catheter to which the scaffold is crimped, and/or there is a first catheter for rejuvenation and a second catheter to which the scaffold is crimped and the balloon of the first catheter has a higher nominal diameter than the balloon of the second catheter.

1k. The method of Concept(s) 1-1j, 2, 3-3c, or 4-4d, or 5-5f, wherein the wall thickness of the tube or scaffold at crimping is less than about 150 microns, about 100 microns, about 120 microns, less than about 100 microns, between about 88 and 100 microns, between about 100 and 120 microns, or between about 80 and 100 microns.

1l. The method of Concept(s) 1-1k, 2, 3-3c, or 4-4d, or 5-5f, wherein an aspect ratio (AR) of strut width to wall thickness of a strut of the scaffold is between about 1.5 and 1.9, 1.5 to 1.8, 1 to 1.5, 1 to 2.2 or 1.4 to 2.2.

1m. The method of Concept(s) 1-1l, 2, 3-3c, or 4-4d, or 5-5f, wherein the tube is substantially or completely a blend of polylactide (PLA) and a PLA and polycaprolactone (PCL) random copolymer (20% PCL) and the blended PLA-PCL combination has between about 1% to 5% by weight PCL; or the tube comprises substantially high molecular weight PLLA.

1n. The method of Concept(s) 1-1 m, 2, 3-3c, 4-4d, or 5-5f, wherein the scaffold has rings interconnected by struts, and the scaffold pattern is one of rings with 6 or 7 crests and 3 links connecting adjacent rings, and the scaffold pattern has one of symmetric W-cells or a combination of symmetric W-calls and asymmetric W-V cells.

1o. The method of Concept(s) 1-1l, 2, 3-3c, or 4-4d wherein the forming process induces a biaxial orientation of polymer chains to increase a radial strength in the tube.

2. A method for making a medical device, comprising:
providing a tube made from a material comprising a polymer composition having a glass transition temperature (Tg), the tube being formed by, or modified by a forming process, wherein the forming process includes the step of at least one of raising the temperature of the tube to about, or greater than about Tg or radially straining the material beyond a yield strain for the material;

making a scaffold from the tube formed by, or modified by the forming process;

shortly after making the scaffold, reducing the temperature of the scaffold to about 50, 60, 80, 100, 50 to 150, or about 50 to 80 degrees below Tg;

thawing the scaffold; and crimping the scaffold to a balloon shortly after thawing the scaffold.

3. A method for crimping, comprising providing a scaffolding comprising a polymer having a glass transition temperature (Tg); and placing the scaffold within a crimping device and while the scaffold is within the crimping device performing the steps of:

raising the temperature of the scaffold to between about 10 to 20 degrees above Tg, followed by lowering the scaffold temperature to between about Tg and 15 degrees below Tg; and while the scaffold has the lowered temperature crimping the scaffold from a first diameter to a second diameter.

3a. The method of Concept(s) 3, wherein the scaffold has biaxially orientated polymer chains during crimping and after raising the temperature of the scaffold to between about 10 to 20 degrees above Tg.

3b. The method of Concept(s) 3-3a, further including the step of erasing ageing in the scaffold comprising the step of raising the temperature of the scaffold to between about 10 to 20 degrees above Tg and maintaining the temperature for between about less than 10 or 20 minutes or between about 5 and 10 minutes.

3c. The method of Concept(s) 3-3b, wherein the crimping includes inflating the balloon when the scaffold diameter is being reduced in size.

4. A method for coating, comprising the steps of:

applying a coating comprising a solvent to a scaffold made from a polymer tube, wherein the tube polymer has a glass transition temperature (Tg); and removing the solvent, including the step of raising the temperature of the scaffold to above Tg.

4a. The method of Concept(s) 4, wherein the removing a solvent includes the step of applying forced air drying to remove the solvent, wherein the forced air has a temperature above Tg.

4b. The method of Concept(s) 4, wherein the removing a solvent includes the step of placing the scaffold within a closed space having a temperature above Tg.

4c. The method of Concept(s) 4-4b, wherein the temperature is between about 10 to 20 degrees above Tg.

4d. The method of Concept(s) 4-4c, further including the step of erasing ageing in the scaffold comprising the step of raising the temperature of the scaffold to between about 10 to 20 degrees above Tg and maintaining the temperature for between about less than 10 or 20 minutes or between about 5 and 10 minutes.

5. A method for making a medical device, comprising:

providing a tube made from a material comprising a polymer composition;

radially strengthening the tube by inducing a biaxial orientation of polymer chains in the tube;

cutting a scaffold from the tube while the tube has the biaxial orientation of polymer chains;

erasing ageing in the scaffold; and after erasing ageing, crimping the scaffold to a balloon.

5a. The method of Concept(s) 5, wherein the polymer composition has a glass transition temperature (Tg) and the erasing ageing includes the step of raising the scaffold temperature to between about 10 and 20 degrees above Tg.

5b. The method of Concept(s) 5-5a, wherein the erasing ageing includes the step of raising the scaffold temperature above Tg for a duration of not more than 5, 10 or 20 minutes.

5c. The method of Concept(s) 5-5b, wherein the scaffold is crimped to the balloon between about 30 minutes, 1 hour, 5 hours, not more than 8 hours or not more than 24 hours after the erasing ageing.

5d. The method of Concept(s) 5-5c, further including the step of coating the scaffold with a drug-polymer composition after erasing ageing and before crimping the scaffold to the balloon.

5e. The method of Concept(s) 5-5d, wherein the erasing ageing takes place within a crimp head.

5f. The method of Concept(s) 5-5e, wherein the radially strengthening the tube includes one or more of blow-molding above Tg, die drawing above Tg.

6. A method of fabricating a polymer stent comprising:

providing a biodegradable polymer scaffold comprising a polymer, the scaffold having an expanded configuration and a crimped configuration for delivery in a vascular lumen;

thermally treating the scaffold to reverse physical aging of the scaffold; and crimping the scaffold to the crimped configuration having reversed physical aging or shortly after thermally treating.

6a. The method of Concept(s) 6, wherein the provided scaffold comprises induced biaxial orientation of the polymer chains and the thermally treated scaffold includes at least some of the induced biaxial orientation.

6b. The method of Concept(s) 6, wherein the thermal treatment reduces damage due to crimping at the crest regions of the scaffold.

6c. The method of Concept(s) 6, wherein reversed physical aging comprises a modification selected from the group consisting of decreased density of the scaffold polymer, increased elongation at break of the scaffold polymer, decreased modulus of the scaffold polymer, increased radial strength of the scaffold, increase expansion capability of the scaffold, reduced damage to the scaffold at crimping, and any combination thereof.

6d. The method of Concept(s) 6, wherein the thermal treatment is above a glass transition temperature (Tg) and below a melting temperature (Tm) of the polymer in the expanded configuration.

6e. The method of Concept(s) 6, wherein the provided scaffold comprises a crystallinity of at least 20%.

6f. The method of Concept(s) 6, wherein the thermal treatment is performed after forming the scaffold from a tube and before coating the scaffold.

6g. The method of Concept(s) 6, wherein the thermal treatment is performed during a coating step of the scaffold.

6h. The method of Concept(s) 6, wherein the thermal treatment is performed after coating the scaffold.

6i. The method of Concept(s) 6, further comprising freezing the scaffold after the thermal treatment to prevent the physical aging.

6j. The method of Concept(s) 6, wherein the scaffold is crimped from 60 sec to 60 min after the thermal treatment.

6k. The method of Concept(s) 6, wherein the scaffold is crimped from 60 sec to 60 min after the thermal treatment.

6l. The method of Concept(s) 6, wherein the thermal treatment is at a temperature from Tg to (Tg+Tm)/2.

6m. The method of Concept(s) 6, wherein the thermal treatment does not increase a crystallinity of the scaffold.

6n. The method of Concept(s) 6, wherein the thermal treatment increases a crystallinity of the scaffold by 0.6 to 2%.

6o. The method of Concept(s) 6, wherein the scaffold has a crystallinity between 20 and 50%.

6p. The method of Concept(s) 6, wherein a time of the thermal treatment is 60 sec to 60 min.

6o. The method of Concept(s) 6, wherein the time of the thermal treatment is 8 to 60 min.

6q. The method of Concept(s) 6 wherein the thermal treatment is performed in an inert atmosphere.

6r. The method of Concept(s) 6, wherein the thermal treatment is performed in a vacuum oven.

6s. The method of Concept(s) 6, wherein the scaffold is disposed on a rod during the treatment and the scaffold is heated electrically or by passage of a heat transfer fluid through the scaffold.

6t. The method of Concept(s) 6, wherein the treatment comprises heating steps to dry coating composition applied to the scaffold between repeated coating composition application steps, wherein a temperature of the heating steps is 80° C. to 620° C.

6u. The method of Concept(s) 6, wherein the scaffold is crimped less than 60 min after coating the scaffold.

6v. The method of Concept(s) 6, wherein the thermal treatment is performed with the scaffold disposed within a crimper prior to crimping to the crimped configuration, wherein the crimper is configured to heat the scaffold.

6w. The method of Concept(s) 6, wherein the thermal treatment is performed with the scaffold disposed within a crimper prior to crimping and the scaffold is heated by heated air passing through a crimper bore in which the scaffold is disposed.

6x. The method of Concept(s) 6, wherein the thermal treatment is performed with the scaffold disposed within a crimper prior to crimping and the scaffold is heated by a crimper having jaws.

6y. The method of Concept(s) 6, wherein the thermal treatment is performed with the scaffold disposed within a crimper prior to crimping, the crimper having jaws that are hollow that contain a recirculating heat transfer fluid.

6z. The method of Concept(s) 6, wherein the thermal treatment comprises moving the scaffold through a tunnel or conveyor oven.

6aa. The method of Concept(s) 6, wherein the thermal treatment comprises heating the scaffold in a microwave oven containing air or an inert gas.

6bb. The method of Concept(s) 6, wherein the thermal treatment comprises heating the scaffold using RF induction heating.

6cc. The method of Concept(s) 6, wherein the thermal treatment comprises heating the scaffold with an infrared lamp.

6dd. The method of Concept(s) 6, wherein shortly after the thermal treatment, storing the scaffold at a temperature of 4° C. or less, further comprising removing the scaffold from the container, allowing the scaffold to equilibrate to ambient temperature, and crimping the equilibrated scaffold to the crimped configuration.

7. A method of fabricating a polymer stent comprising:
providing a biodegradable polymer scaffold comprising a polymer, wherein the scaffold comprises induced biaxial orientation of the polymer chains, the scaffold having an expanded configuration and a crimped configuration for delivery in a vascular lumen;
thermally treating the scaffold to reverse physical aging of the scaffold,
and
crimping the scaffold to the crimped configuration having reversed physical aging or shortly after thermally treating.

7a. The method of Concept(s) 6, wherein the thermally treated scaffold includes at least some of the induced biaxial orientation.

7b. The method of Concept(s) 7, wherein the thermal treatment reduces damage due to crimping at the crest regions of the scaffold.

7c. The method of Concept(s) 7, wherein the thermal treatment is above a glass transition temperature (Tg) and below a melting temperature (Tm) of the polymer in the expanded configuration.

7d. The method of Concept(s) 7, wherein reversal of physical aging comprises a modification of the scaffold selected from the group consisting of decrease density of the scaffold polymer, increase elongation at break of the scaffold polymer, decrease modulus of the scaffold polymer, increase radial strength of the scaffold, increase expansion capability of the scaffold, reduced damage to the scaffold at crimping, and any combination thereof.

8. A method of fabricating a polymer stent comprising:
providing a biodegradable polymer scaffold comprising a polymer, the scaffold having an expanded configuration and a crimped configuration for delivery in a vascular lumen;
thermally treating the scaffold above a glass transition temperature (Tg) and below a melting temperature (Tm) of the polymer to reverse physical aging of the scaffold;
optionally freezing the scaffold shortly after thermally treating; and
crimping the scaffold to the crimped configuration shortly after the thermal treatment or shortly after thawing the frozen scaffold.

8a. The method of Concept(s) 8, wherein the provided scaffold comprises induced biaxial orientation of the polymer chains and the thermally treated scaffold includes at least some of the induced biaxial orientation 8b. The method of Concept(s) 8, wherein the thermal treatment time is 6 to 65 min.

8c. The method of Concept(s) 8, wherein the thermal treatment modifies the scaffold, the modification selected from the group consisting of decrease density of the scaffold polymer, increase elongation at break of the scaffold polymer, decrease modulus of the scaffold polymer, increase radial strength of the scaffold, increase expandability of the scaffold, reduced damage to the scaffold at crimping, and any combination thereof.

8d. The method of Concept(s) 8, wherein the thermal processing reduces damage due to crimping at the crest regions of the scaffold.

9. A method of fabricating a polymer stent comprising:
processing a bioresorbable polymer to form a radially expandable scaffold, the processing comprising increasing a temperature of the polymer above a glass transition temperature (Tg) and below a melting temperature (Tm) followed by reducing the temperature below the Tg, the scaffold having an expanded configuration and a crimped configuration for delivery in a vascular lumen;
thermally treating the scaffold to reverse physical aging of the scaffold, and
crimping the scaffold to the crimped configuration having reversed physical aging or shortly after thermally treating.

9a. The method of Concept(s) 9, wherein the thermal treatment does not erase memory of the processing.

9b. The method of Concept(s) 9, wherein the processing comprises inducing biaxial orientation of the polymer chains and the thermally treated scaffold includes at least some of the induced biaxial orientation.

9c. The method of Concept(s) 9, wherein the thermal treatment reduces damage due to crimping at the crest regions of the scaffold.

9d. The method of Concept(s) 9, wherein following forming of the scaffold, physical aging of the scaffold causes modification selected from the group consisting of increased density of the scaffold polymer, decreased elongation at break of the scaffold polymer, increased modulus of the scaffold polymer, decrease in expandability of the scaffold, decrease in radial strength of the scaffold, and any combination thereof.

9e. The method of Concept(s) 9, wherein the thermal treatment modifies the scaffold, the modification selected from the group consisting of decrease density of the scaffold polymer, increase elongation at break of the scaffold polymer, decrease modulus of the scaffold polymer, increase radial strength of the scaffold, increase expandability of the scaffold, reduced damage to the scaffold at crimping, and any combination thereof.

10. A method of fabricating a polymer stent comprising:
processing a bioresorbable polymer to form a radially expandable scaffold, the scaffold having an expanded configuration and a crimped configuration for delivery in a vascular lumen, the processing comprising increasing a temperature of the polymer above a glass transition temperature (Tg) and below a melting temperature (Tm) followed by reducing the temperature below the Tg,
thermally treating the scaffold to reverse physical aging, the thermal treatment being above a glass transition temperature (Tg) and below a melting temperature (Tm) of the polymer; and
optionally freezing the scaffold shortly after thermally treating; and
crimping the scaffold to the crimped configuration shortly after the thermal treatment or shortly after thawing the frozen scaffold.

10a. The method of Concept(s) 10, wherein the thermal treatment does not erase memory of the processing.

10b. The method of Concept(s) 10, wherein the processing comprises inducing a biaxial orientation of the polymer chains and the thermally treated scaffold includes at least some of the induced biaxial orientation.

10c. The method of Concept(s) 10, wherein the thermal treatment reduces damage due to crimping at the crest regions of the scaffold.

10d. The method of Concept(s) 10, wherein the thermal treatment modifies the scaffold, the modification selected from the group consisting of decreased density of scaffold polymer, increased elongation at break of the scaffold polymer, decreased modulus of the scaffold polymer, increased radial strength of the scaffold, increased expansion capability of the scaffold, reduced damage to the scaffold at crimping, and any combination thereof.

11. A method of fabricating a polymer stent comprising:
providing a biodegradable polymer scaffold comprising a polymer, the scaffold having an expanded configuration and a crimped configuration for delivery in a vascular lumen;
treating the scaffold with a solvent to reverse physical aging of the scaffold; and
crimping the scaffold to the crimped configuration having reversed physical aging or shortly after solvent treating.

11a. The method of Concept(s) 11, wherein the provided scaffold comprises induced biaxial orientation of the polymer chains and the solvent treated scaffold includes at least some of the induced biaxial orientation.

11a. The method of Concept(s) 11, wherein the treatment comprises placing the scaffold disposed on a mandrel in a chamber filled with solvent vapor.

11b. The method of Concept(s) 11, wherein the treatment is performed at ambient temperature.

11c. The method of Concept(s) 11, wherein the solvent is selected from the group consisting of acetonitrile, dimethylsulfoxide (DMSO), chloroform, acetone, water (buffered saline), xylene, methanol, ethanol, 6-propanol, tetrahydrofuran, 6-butanone, dimethylformamide, dimethylacetamide, cyclohexanone, ethyl acetate, methylethylketone, propylene glycol monomethylether, isopropanol, isopropanol admixed with water, N-methylpyrrolidinone, toluene, and any combinations thereof.

11d. The method of Concept(s) 11, wherein the treatment comprises removing solvent from the scaffold prior to crimping.

11e. The method of Concept(s) 11, wherein the solvent treatment modifies the scaffold, the modification selected from the group consisting of decreased density of scaffold polymer, increased elongation at break of the scaffold polymer, decreased modulus of the scaffold polymer, increased radial strength of the scaffold, increased expansion capability of the scaffold, reduced damage to the scaffold at crimping, and any combination thereof.

12. A method of fabricating a polymer stent comprising:
processing a bioresorbable polymer to form a radially expandable scaffold, the processing comprising increasing a temperature of the polymer above a glass transition temperature (Tg) and below a melting temperature (Tm) followed by reducing the temperature below the Tg, the scaffold having an expanded configuration and a crimped configuration for delivery in a vascular lumen;
solvent treating the scaffold to reverse physical aging of the scaffold, and
crimping the scaffold to the crimped configuration having reversed physical aging or shortly after thermally treating.

12a. The method of Concept(s) 12, wherein the solvent treatment does not erase memory of the processing.

12b. The method of Concept(s) 12, wherein the processing comprises inducing a biaxial orientation of the polymer chains and the thermally treated scaffold includes at least some of the induced biaxial orientation.

12c. The method of Concept(s) 12, wherein the solvent treatment reduces damage due to crimping at the crest regions of the scaffold.

12d. The method of Concept(s) 12, wherein following forming of the scaffold, physical aging of the scaffold causes modification selected from the group consisting of increased density of the scaffold polymer, decreased elongation at break of the scaffold polymer, increased modulus of the scaffold polymer, decrease in expandability of the scaffold, decrease in radial strength of the scaffold, and any combination thereof.

12e. The method of Concept(s) 12, wherein the solvent treatment modifies the scaffold, the modification selected from the group consisting of decrease density of the scaffold polymer, increase elongation at break of the scaffold polymer, decrease modulus of the scaffold polymer, increase radial strength of the scaffold, increase expansion capability of the scaffold, reduced damage to the scaffold at crimping, and any combination thereof.

12f. The method of Concept(s) 12, wherein the treatment comprises removing solvent from the scaffold prior to crimping.

What is claimed is:

1. A method for making a medical device, comprising:
providing a tube made from a material comprising a polymer composition having a glass transition temperature (Tg), the tube being formed by, or modified by a forming process, wherein the forming process includes the step of at least one of raising the temperature of the tube to about, or greater than about Tg or radially straining the material beyond a yield strain for the material;
making a scaffold from the tube formed or modified by the forming process; and
crimping the scaffold to a balloon such that a significant plastic deformation is imposed on the scaffold when crimped to the balloon, including the steps of
reducing a scaffold diameter from a pre-crimp diameter to a first diameter,
rejuvenating the scaffold including radially expanding the scaffold diameter from the first diameter to a second diameter, and
reducing the scaffold diameter from the second diameter to a third diameter that is less than the first diameter.

2. The method of claim 1, wherein the rejuvenating the scaffold includes radially expanding the scaffold diameter by about 5 to 15% relative to the pre-crimp diameter or the first diameter.

3. The method of claim 1, wherein the rejuvenating includes inducing a strain beyond the yield strain for the material, wherein a crest of a scaffold ring has a highest yield strain of about 5 to 20% beyond the strain where yield begins to occur for the scaffold crest when the scaffold is radially expanded.

4. The method of claim 1, wherein a scaffold temperature is about Tg or about 15 Deg. C less than Tg when the scaffold diameter is increased from the first diameter to the second diameter.

5. The method of claim 1, wherein the scaffold diameter is increased from the first diameter to the second diameter by inflating the balloon.

6. The method of claim 1, wherein a wall thickness of the scaffold during crimping is less than about 120 microns.

7. The method of claim 1, wherein an aspect ratio (AR) of strut width to wall thickness of a strut of the scaffold is between about 1 to 2.2.

8. The method of claim 1, wherein the tube is substantially or completely a blend of polylactide (PLA) and a PLA and polycaprolactone (PCL) random copolymer (20% PCL) and the blended PLA-PCL combination has between about 1% to 5% by weight PCL; or the tube comprises substantially high molecular Weight poly(L-lactide).

9. The method of claim 1, wherein the forming process induces a biaxial orientation of polymer chains to increase a radial strength in the tube and the rejuvenation does not remove the biaxial orientation.

10. The method of claim 1,
wherein the rejuvenating the scaffold is performed using a balloon catheter comprising the balloon to which the scaffold is crimped, or
wherein the balloon is a second balloon, and wherein the rejuvenating the scaffold is performed using a first balloon catheter comprising a first balloon and the crimping the scaffold is performed using a second balloon catheter comprising the balloon to which the scaffold is crimped, and the first balloon has a higher nominal diameter of the second balloon.

11. A method for crimping, comprising
providing a scaffold comprising a polymer having a glass transition temperature (Tg); and
placing the scaffold within a crimping device and while the scaffold is within the crimping device performing the steps of:
raising a temperature of the scaffold to between about 10 to 20 degrees above Tg, followed by lowering the scaffold temperature to a lower temperature between about Tg and 15 degrees below Tg; and
while the scaffold has the lower temperature crimping the scaffold including reducing a scaffold diameter from a first diameter to a second diameter.

12. The method of claim 11, wherein the scaffold has biaxially orientated polymer chains before and after raising the temperature of the scaffold to between about 10 to 20 degrees above Tg.

13. The method of claim 11, wherein the scaffold temperature is raised and then maintained at a raised temperature to rejuvenate the scaffold, including raising the temperature of the scaffold to between about 10 to 20 degrees above Tg and maintaining the temperature for less than 10 minutes.

14. The method of claim 11, wherein the scaffold is disposed on an inflated balloon while the scaffold diameter is reduced from the first diameter to the second diameter.

15. A method of crimping, comprising:
providing a scaffold comprising a biodegradable polymer,
rejuvenating the scaffold, wherein the rejuvenation puts the polymer into a thermodynamic non-equilibrium state, thereby reversing a physical ageing of the scaffold; and
using an iris-type crimping mechanism,
crimping the scaffold including reducing a diameter of the scaffold from a pre-crimp diameter to a first diameter within one day of rejuvenating the scaffold, wherein the crimping produces a crimped scaffold,
removing the crimped scaffold from the crimping mechanism, and
placing the crimped scaffold in a sheath to reduce recoil of the crimped scaffold.

16. The method of claim 15, wherein the crimping the scaffold occurs within 60 sec to 60 min after the rejuvenating the scaffold.

17. The method of claim 15, wherein the scaffold is rejuvenated while the scaffold is disposed within a crimp head of the crimping mechanism.

18. The method of claim 15, wherein the scaffold is rejuvenated shortly before placing the scaffold within a crimp head of the crimping mechanism.

19. The method of claim 15, wherein the polymer comprises biaxially orientated polymer chains before and after rejuvenation.

20. The method of claim 15, wherein the rejuvenating the scaffold increases a crystallinity of the polymer by 0.6% to 2%.

21. The method of claim 15, wherein the polymer has a glass transition temperature (Tg) and the rejuvenating the scaffold step includes a thermal treatment, including
applying heat to the scaffold to raise a temperature of the scaffold to between about 10 to 20 degrees above Tg and maintaining the temperature for between about 5 to 20 minutes.

22. The method of claim 21, wherein the scaffold is disposed on a rod during the thermal treatment, wherein the rod is thermally insulated such that about no heat is lost by thermal conductivity from the scaffold to the rod during the thermal treatment.

23. The method of claim 22, wherein the outer diameter of the rod is about the same as an inner diameter of the scaffold prior to the thermal treatment.

24. The method of claim 22, wherein the scaffold is made from a radially expanded precursor tube, such that the thermal treatment causes an inner diameter of the scaffold to decrease during the thermal treatment.

25. The method of claim 24, wherein the rod imposes a radial constraint on the scaffold during the thermal treatment to cause a crown angle of the scaffold to increase during the thermal treatment.

26. The method of claim 15, wherein the polymer is a first polymer and has a glass transition temperature (Tg) and the rejuvenating the scaffold step comprises coating the scaffold with a second polymer followed by drying a coating comprising the second polymer within one day of the reducing the scaffold diameter, wherein the drying the coating comprises raising a scaffold temperature to a temperature of between about 10 to 20 degrees above Tg.

27. The method of claim 15, wherein the rejuvenating the scaffold step comprises applying a solvent to the scaffold.

\* \* \* \* \*